(12) United States Patent
Schymkowitz et al.

(10) Patent No.: US 9,389,219 B2
(45) Date of Patent: Jul. 12, 2016

(54) METHODS FOR SCREENING INHIBITORS OF TUMOR ASSOCIATED PROTEIN AGGREGATION

(75) Inventors: Joost Schymkowitz, Meensel-Kiezegem (BE); Frederic Rousseau, Groot-Bijgaarden (BE); Jie Xu, Shanghai (CN); Frederik De Smet, Winksele (BE)

(73) Assignees: Vrije Universiteit Brussel, Brussel (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 14/007,602

(22) PCT Filed: Mar. 26, 2012

(86) PCT No.: PCT/EP2012/055291
§ 371 (c)(1),
(2), (4) Date: Feb. 13, 2014

(87) PCT Pub. No.: WO2012/130785
PCT Pub. Date: Oct. 4, 2012

(65) Prior Publication Data
US 2014/0170239 A1     Jun. 19, 2014

Related U.S. Application Data

(60) Provisional application No. 61/465,892, filed on Mar. 25, 2011.

(51) Int. Cl.
| | |
|---|---|
| G01N 31/00 | (2006.01) |
| A61K 38/04 | (2006.01) |
| G01N 33/50 | (2006.01) |
| C12Q 1/68 | (2006.01) |

(52) U.S. Cl.
CPC ............ *G01N 33/5008* (2013.01); *C12Q 1/68* (2013.01); *G01N 33/5011* (2013.01); *G01N 2333/4748* (2013.01); *G01N 2500/10* (2013.01)

(58) Field of Classification Search
None
See application file for complete search history.

(56) References Cited

U.S. PATENT DOCUMENTS

2005/0112607 A1* 5/2005 Bamdad et al. .............. 435/6

FOREIGN PATENT DOCUMENTS

| EP | 1 699 085 A | 6/2006 |
|---|---|---|
| WO | WO 2007/071789 A1 | 6/2007 |
| WO | WO 2012/130785 A1 | 10/2012 |

OTHER PUBLICATIONS

Wang and Sun, Translational Oncology vol. 3, No. 1, 2010.*
Apostol et al., A Cell-Based Assay for Aggregation Inhibitors as Therapeutics of Polyglutamine-Repeat Disease and Validation in *Drosophila*, Proceedings of the National Academy of Sciences, National Academy of Sciences, May 13, 2003, pp. 5950-5955, vol. 100, No. 10.
Linding et al., A Comparative Study of the Relationship Between Protein Structure and Beta-Aggregation in Globular and Intrinsically Disordered Proteins, Journal of Molecular Biology, Sep. 3, 2004, pp. 345-353, vol. 342, No. 1. Academic Press, United Kingdom.
Xu et al., Gain of Function of Mutant p53 by Coaggregation with Multiple Tumor Suppressors, Nature Chemical Biology. May 2011, pp. 285-295, vol. 7, No. 5.
PCT International Search Report, PCT/EP2012/055291 dated Jun. 5, 2012.

* cited by examiner

*Primary Examiner* — Jeanette Lieb
(74) *Attorney, Agent, or Firm* — TraskBritt, P.C.

(57) ABSTRACT

The disclosure relates to the fields of protein aggregation diseases including cancer. More specifically, it concerns a screening method for identifying compounds that inhibit or disrupt co-aggregation of one or more member proteins of a disease-related protein aggregome, in particular, a tumor-associated protein aggregome. Further, disclosed are agents and compounds identified by the screening method that can be applied to prevent or to treat protein aggregation diseases, such as cancer.

15 Claims, 32 Drawing Sheets
(22 of 32 Drawing Sheet(s) Filed in Color)

b c a b continued . . .

c

| | | | | | | |
|---|---|---|---|---|---|---|
| wild type | + | - | - | - | - | - |
| R175H | - | + | + | + | + | + |
| L344P | - | - | + | + | + | + |
| T256R | - | - | - | + | - | + |
| MG132 | - | - | - | - | + | + | a b

| Patient Number | Gender | Age | p53 genotype | p53 in nucleus | p53 in cytoplasm |
|---|---|---|---|---|---|
| B07/7524/6 | Female | 79 | wild type | - | - |
| B08/559/19 | Female | 59 | wild type | + | - |
| B08/919/3 | Female | 72 | R282W | - | + |
| B08/1794/4 | Male | 74 | wild type | - | - |
| B08/1961/5 | Male | 77 | E285Stop | - | - |
| B08/2734/3 | Female | 75 | wild type | - | - |
| B08/2880/4 | Male | 78 | wild type | + | - |
| B08/2311/7 | Male | 47 | wild type | - | - |
| B08/2288/9 | Male | 72 | wild type | + | - |
| B08/3268/3 | Male | 69 | wild type | - | - | continued . . .

b continued . . .

continued . . .

d continued . . .

a b c Peptide position p53 amino acid sequence a b continued . . .

continued . . .

SEQUENCE LISTING

```
<160> NUMBER OF SEQ ID NOS: 84

<210> SEQ ID NO 1
<211> LENGTH: 7
<212> TYPE: PRT
<213> ORGANISM: Homo sapiens

<400> SEQUENCE: 1

Ile Leu Leu Ile Ile Thr Asp
1               5

<210> SEQ ID NO 2
<211> LENGTH: 7
<212> TYPE: PRT
<213> ORGANISM: Homo sapiens

<400> SEQUENCE: 2

Ile Leu Thr Ile Ile Thr Leu
1               5
```

```
<210> SEQ ID NO 3
<211> LENGTH: 7
<212> TYPE: PRT
<213> ORGANISM: Homo sapiens

<400> SEQUENCE: 3

Ile Leu Ile Ile Ile Thr Leu
1               5

<210> SEQ ID NO 4
<211> LENGTH: 7
<212> TYPE: PRT
<213> ORGANISM: Homo sapiens

<400> SEQUENCE: 4

Ile Leu Ile Ile Val Thr Leu
1               5

<210> SEQ ID NO 5
<211> LENGTH: 7
<212> TYPE: PRT
<213> ORGANISM: Homo sapiens

<400> SEQUENCE: 5

Ile Leu Ser Ile Asp Thr Leu
1               5

<210> SEQ ID NO 6
<211> LENGTH: 7
<212> TYPE: PRT
<213> ORGANISM: Homo sapiens

<400> SEQUENCE: 6

Ile Leu Asp Ile Ile Thr Ser
1               5

<210> SEQ ID NO 7
<211> LENGTH: 7
<212> TYPE: PRT
<213> ORGANISM: Homo sapiens

<400> SEQUENCE: 7

Ile Leu Thr Asn Thr Thr Leu
1               5

<210> SEQ ID NO 8
<211> LENGTH: 7
<212> TYPE: PRT
<213> ORGANISM: Homo sapiens

<400> SEQUENCE: 8

Ile Leu Thr Ile Gly Thr Gly
1               5

<210> SEQ ID NO 9
<211> LENGTH: 7
<212> TYPE: PRT
<213> ORGANISM: Homo sapiens

<400> SEQUENCE: 9

Ala Leu Val Ile Ile Thr Leu
1               5

<210> SEQ ID NO 10
<211> LENGTH: 7
```

```
<212> TYPE: PRT
<213> ORGANISM: Homo sapiens

<400> SEQUENCE: 10

Asp Leu Thr Ile Ile Asp Leu
1               5

<210> SEQ ID NO 11
<211> LENGTH: 7
<212> TYPE: PRT
<213> ORGANISM: Homo sapiens

<400> SEQUENCE: 11

Ile Thr Thr Gly Ile Thr Leu
1               5

<210> SEQ ID NO 12
<211> LENGTH: 7
<212> TYPE: PRT
<213> ORGANISM: Homo sapiens

<400> SEQUENCE: 12

Ile Leu Thr Lys Tyr Thr Leu
1               5

<210> SEQ ID NO 13
<211> LENGTH: 7
<212> TYPE: PRT
<213> ORGANISM: Homo sapiens

<400> SEQUENCE: 13

Ile Tyr Thr Gly Ile Thr Leu
1               5

<210> SEQ ID NO 14
<211> LENGTH: 14
<212> TYPE: PRT
<213> ORGANISM: Homo sapiens

<400> SEQUENCE: 14

Arg Arg Pro Ile Leu Thr Ile Ile Thr Leu Glu Asp Gly Ser
1               5                   10

<210> SEQ ID NO 15
<211> LENGTH: 7
<212> TYPE: PRT
<213> ORGANISM: Homo sapiens

<400> SEQUENCE: 15

Leu Leu Thr Ile Glu Thr Leu
1               5

<210> SEQ ID NO 16
<211> LENGTH: 7
<212> TYPE: PRT
<213> ORGANISM: Homo sapiens

<400> SEQUENCE: 16

Phe Leu Thr Ile Phe Thr Leu
1               5

<210> SEQ ID NO 17
<211> LENGTH: 7
<212> TYPE: PRT
<213> ORGANISM: Homo sapiens
```

```
<400> SEQUENCE: 17

Ile Leu Gln Ile Ile Ser Leu
1               5

<210> SEQ ID NO 18
<211> LENGTH: 7
<212> TYPE: PRT
<213> ORGANISM: Homo sapiens

<400> SEQUENCE: 18

Ile Leu Thr Ile Ser Ser Leu
1               5

<210> SEQ ID NO 19
<211> LENGTH: 7
<212> TYPE: PRT
<213> ORGANISM: Homo sapiens

<400> SEQUENCE: 19

Ile Leu Lys Gln Ile Thr Leu
1               5

<210> SEQ ID NO 20
<211> LENGTH: 7
<212> TYPE: PRT
<213> ORGANISM: Homo sapiens

<400> SEQUENCE: 20

Ile Leu Thr Ile Thr Thr Pro
1               5

<210> SEQ ID NO 21
<211> LENGTH: 7
<212> TYPE: PRT
<213> ORGANISM: Homo sapiens

<400> SEQUENCE: 21

Lys Leu Thr Ile Ile Thr Ser
1               5

<210> SEQ ID NO 22
<211> LENGTH: 7
<212> TYPE: PRT
<213> ORGANISM: Homo sapiens

<400> SEQUENCE: 22

Ile Leu Thr Lys Ser Thr Leu
1               5

<210> SEQ ID NO 23
<211> LENGTH: 7
<212> TYPE: PRT
<213> ORGANISM: Homo sapiens

<400> SEQUENCE: 23

Ile Leu Thr Ser Gly Thr Leu
1               5

<210> SEQ ID NO 24
<211> LENGTH: 7
<212> TYPE: PRT
<213> ORGANISM: Homo sapiens

<400> SEQUENCE: 24
```

```
Ile Val Thr Ile Ile Thr Ala
1               5

<210> SEQ ID NO 25
<211> LENGTH: 7
<212> TYPE: PRT
<213> ORGANISM: Homo sapiens

<400> SEQUENCE: 25

Ile Leu Gly Lys Ile Thr Leu
1               5

<210> SEQ ID NO 26
<211> LENGTH: 7
<212> TYPE: PRT
<213> ORGANISM: Homo sapiens

<400> SEQUENCE: 26

Ile Leu Thr Lys Pro Thr Leu
1               5

<210> SEQ ID NO 27
<211> LENGTH: 7
<212> TYPE: PRT
<213> ORGANISM: Homo sapiens

<400> SEQUENCE: 27

Ile Leu Gln Ile Ile Thr Glu
1               5

<210> SEQ ID NO 28
<211> LENGTH: 7
<212> TYPE: PRT
<213> ORGANISM: Homo sapiens

<400> SEQUENCE: 28

Ile Leu Arg Gln Ile Thr Leu
1               5

<210> SEQ ID NO 29
<211> LENGTH: 7
<212> TYPE: PRT
<213> ORGANISM: Homo sapiens

<400> SEQUENCE: 29

Ile Leu Thr Ile Lys Glu Leu
1               5

<210> SEQ ID NO 30
<211> LENGTH: 7
<212> TYPE: PRT
<213> ORGANISM: Homo sapiens

<400> SEQUENCE: 30

Ile Leu Thr Glu Ile His Leu
1               5

<210> SEQ ID NO 31
<211> LENGTH: 7
<212> TYPE: PRT
<213> ORGANISM: Homo sapiens

<400> SEQUENCE: 31

Ile Leu Lys Asn Ile Thr Leu
```

<210> SEQ ID NO 32
<211> LENGTH: 7
<212> TYPE: PRT
<213> ORGANISM: Homo sapiens

<400> SEQUENCE: 32

Ile Leu Thr Ile Leu Thr Glu
1               5

<210> SEQ ID NO 33
<211> LENGTH: 7
<212> TYPE: PRT
<213> ORGANISM: Homo sapiens

<400> SEQUENCE: 33

Gly Leu Thr Ile Pro Thr Leu
1               5

<210> SEQ ID NO 34
<211> LENGTH: 7
<212> TYPE: PRT
<213> ORGANISM: Homo sapiens

<400> SEQUENCE: 34

Ile Leu Thr Ile Val Ser Leu
1               5

<210> SEQ ID NO 35
<211> LENGTH: 7
<212> TYPE: PRT
<213> ORGANISM: Homo sapiens

<400> SEQUENCE: 35

Thr Leu Thr Ile Ser Thr Leu
1               5

<210> SEQ ID NO 36
<211> LENGTH: 7
<212> TYPE: PRT
<213> ORGANISM: Homo sapiens

<400> SEQUENCE: 36

Ile Leu Thr Leu Ile Glu Leu
1               5

<210> SEQ ID NO 37
<211> LENGTH: 7
<212> TYPE: PRT
<213> ORGANISM: Homo sapiens

<400> SEQUENCE: 37

Ile Lys Thr Ile Ile Asn Leu
1               5

<210> SEQ ID NO 38
<211> LENGTH: 7
<212> TYPE: PRT
<213> ORGANISM: Homo sapiens

<400> SEQUENCE: 38

Ile Leu Thr Lys Ile Ser Leu
1               5

```
<210> SEQ ID NO 39
<211> LENGTH: 7
<212> TYPE: PRT
<213> ORGANISM: Homo sapiens

<400> SEQUENCE: 39

Ile Glu Val Ile Ile Thr Leu
1               5

<210> SEQ ID NO 40
<211> LENGTH: 7
<212> TYPE: PRT
<213> ORGANISM: Homo sapiens

<400> SEQUENCE: 40

Ile His Ala Ile Ile Thr Leu
1               5

<210> SEQ ID NO 41
<211> LENGTH: 7
<212> TYPE: PRT
<213> ORGANISM: Homo sapiens

<400> SEQUENCE: 41

Ile Leu Cys Asp Ile Thr Leu
1               5

<210> SEQ ID NO 42
<211> LENGTH: 7
<212> TYPE: PRT
<213> ORGANISM: Homo sapiens

<400> SEQUENCE: 42

Ile Gln Thr Ile Ser Thr Leu
1               5

<210> SEQ ID NO 43
<211> LENGTH: 7
<212> TYPE: PRT
<213> ORGANISM: Homo sapiens

<400> SEQUENCE: 43

Ile Leu Val Ile Ile Thr Arg
1               5

<210> SEQ ID NO 44
<211> LENGTH: 7
<212> TYPE: PRT
<213> ORGANISM: Homo sapiens

<400> SEQUENCE: 44

Val Leu Thr Ile Ser Thr Leu
1               5

<210> SEQ ID NO 45
<211> LENGTH: 7
<212> TYPE: PRT
<213> ORGANISM: Homo sapiens

<400> SEQUENCE: 45

Ile Leu Thr Ile Cys Thr Lys
1               5

<210> SEQ ID NO 46
```

```
<211> LENGTH: 7
<212> TYPE: PRT
<213> ORGANISM: Homo sapiens

<400> SEQUENCE: 46

Ala Leu Thr Phe Ile Thr Leu
1               5

<210> SEQ ID NO 47
<211> LENGTH: 7
<212> TYPE: PRT
<213> ORGANISM: Homo sapiens

<400> SEQUENCE: 47

Ile Leu Thr Phe Lys Thr Leu
1               5

<210> SEQ ID NO 48
<211> LENGTH: 7
<212> TYPE: PRT
<213> ORGANISM: Homo sapiens

<400> SEQUENCE: 48

Ile Leu Thr Asp Val Thr Leu
1               5

<210> SEQ ID NO 49
<211> LENGTH: 7
<212> TYPE: PRT
<213> ORGANISM: Homo sapiens

<400> SEQUENCE: 49

Ile Thr Thr Val Ile Thr Leu
1               5

<210> SEQ ID NO 50
<211> LENGTH: 7
<212> TYPE: PRT
<213> ORGANISM: Homo sapiens

<400> SEQUENCE: 50

Ile Leu Thr Ile Leu Cys Leu
1               5

<210> SEQ ID NO 51
<211> LENGTH: 7
<212> TYPE: PRT
<213> ORGANISM: Homo sapiens

<400> SEQUENCE: 51

Ile Lys Ser Ile Ile Thr Leu
1               5

<210> SEQ ID NO 52
<211> LENGTH: 7
<212> TYPE: PRT
<213> ORGANISM: Homo sapiens

<400> SEQUENCE: 52

Leu Leu Thr Ile Ile Leu Leu
1               5

<210> SEQ ID NO 53
<211> LENGTH: 7
<212> TYPE: PRT
```

```
<213> ORGANISM: Homo sapiens

<400> SEQUENCE: 53

Cys Leu Thr Ile Ile Thr Gly
1               5

<210> SEQ ID NO 54
<211> LENGTH: 7
<212> TYPE: PRT
<213> ORGANISM: Homo sapiens

<400> SEQUENCE: 54

Met Leu Thr Glu Ile Thr Leu
1               5

<210> SEQ ID NO 55
<211> LENGTH: 7
<212> TYPE: PRT
<213> ORGANISM: Homo sapiens

<400> SEQUENCE: 55

Ile Leu Thr Ser Gln Thr Leu
1               5

<210> SEQ ID NO 56
<211> LENGTH: 7
<212> TYPE: PRT
<213> ORGANISM: Homo sapiens

<400> SEQUENCE: 56

Leu Leu Thr Ile Ile Asn Leu
1               5

<210> SEQ ID NO 57
<211> LENGTH: 7
<212> TYPE: PRT
<213> ORGANISM: Homo sapiens

<400> SEQUENCE: 57

Ala Leu Pro Asn Asn Thr Ser
1               5

<210> SEQ ID NO 58
<211> LENGTH: 9
<212> TYPE: PRT
<213> ORGANISM: Homo sapiens

<400> SEQUENCE: 58

Val Met Ile Cys Ala Tyr Leu Leu His
1               5

<210> SEQ ID NO 59
<211> LENGTH: 9
<212> TYPE: PRT
<213> ORGANISM: Homo sapiens

<400> SEQUENCE: 59

Tyr Val Tyr Tyr Tyr Ser Tyr Leu Leu
1               5

<210> SEQ ID NO 60
<211> LENGTH: 5
<212> TYPE: PRT
<213> ORGANISM: Homo sapiens
```

```
<400> SEQUENCE: 60

Val Ala Leu Leu Phe
1               5

<210> SEQ ID NO 61
<211> LENGTH: 10
<212> TYPE: PRT
<213> ORGANISM: Homo sapiens

<400> SEQUENCE: 61

Met Phe His Phe Trp Val Asn Thr Phe Phe
1               5                   10

<210> SEQ ID NO 62
<211> LENGTH: 7
<212> TYPE: PRT
<213> ORGANISM: Homo sapiens

<400> SEQUENCE: 62

Tyr Leu Val Leu Thr Leu Thr
1               5

<210> SEQ ID NO 63
<211> LENGTH: 7
<212> TYPE: PRT
<213> ORGANISM: Homo sapiens

<400> SEQUENCE: 63

Tyr Leu Val Leu Asn Leu Ser
1               5

<210> SEQ ID NO 64
<211> LENGTH: 9
<212> TYPE: PRT
<213> ORGANISM: Artificial
<220> FEATURE:
<223> OTHER INFORMATION: Mammalian expression plasmid pCMV-HA-p53
      encoding HA-tag

<400> SEQUENCE: 64

Tyr Pro Tyr Asp Val Pro Asp Tyr Ala
1               5

<210> SEQ ID NO 65
<211> LENGTH: 8
<212> TYPE: PRT
<213> ORGANISM: Artificial
<220> FEATURE:
<223> OTHER INFORMATION: pcDNA3-Flag-p53 encoding Flag-tag

<400> SEQUENCE: 65

Asp Tyr Lys Asp Asp Asp Asp Lys
1               5

<210> SEQ ID NO 66
<211> LENGTH: 19
<212> TYPE: DNA
<213> ORGANISM: Artificial
<220> FEATURE:
<223> OTHER INFORMATION: Primer

<400> SEQUENCE: 66
aacgctgccc caaccacga                                              19

<210> SEQ ID NO 67
```

```
<211> LENGTH: 20
<212> TYPE: DNA
<213> ORGANISM: Artificial
<220> FEATURE:
<223> OTHER INFORMATION: Primer

<400> SEQUENCE: 67
gccggttcat gcccctaca                                              20

<210> SEQ ID NO 68
<211> LENGTH: 20
<212> TYPE: DNA
<213> ORGANISM: Artificial
<220> FEATURE:
<223> OTHER INFORMATION: Primer

<400> SEQUENCE: 68
gaagatggtg cgacaaacaa                                             20

<210> SEQ ID NO 69
<211> LENGTH: 20
<212> TYPE: DNA
<213> ORGANISM: Artificial
<220> FEATURE:
<223> OTHER INFORMATION: Primer

<400> SEQUENCE: 69
atgatgaaca gcccaacctc                                             20

<210> SEQ ID NO 70
<211> LENGTH: 20
<212> TYPE: DNA
<213> ORGANISM: Artificial
<220> FEATURE:
<223> OTHER INFORMATION: Primer

<400> SEQUENCE: 70
tgcttcaggg tttcatccag                                             20

<210> SEQ ID NO 71
<211> LENGTH: 18
<212> TYPE: DNA
<213> ORGANISM: Artificial
<220> FEATURE:
<223> OTHER INFORMATION: Primer

<400> SEQUENCE: 71
ggcggcaatc atcctctg                                               18

<210> SEQ ID NO 72
<211> LENGTH: 25
<212> TYPE: DNA
<213> ORGANISM: Artificial
<220> FEATURE:
<223> OTHER INFORMATION: Primer

<400> SEQUENCE: 72
tggaagtcga gtgtgctact caact                                       25

<210> SEQ ID NO 73
<211> LENGTH: 23
<212> TYPE: DNA
<213> ORGANISM: Artificial
<220> FEATURE:
<223> OTHER INFORMATION: Primer

<400> SEQUENCE: 73
```

-continued

```
agattcagaa gtttctgccg gaa                                            23

<210> SEQ ID NO 74
<211> LENGTH: 16
<212> TYPE: DNA
<213> ORGANISM: Artificial
<220> FEATURE:
<223> OTHER INFORMATION: Primer

<400> SEQUENCE: 74
cgctaatggc gggctg                                                    16

<210> SEQ ID NO 75
<211> LENGTH: 21
<212> TYPE: DNA
<213> ORGANISM: Artificial
<220> FEATURE:
<223> OTHER INFORMATION: Primer

<400> SEQUENCE: 75
cggtgacaaa gtcgaagttc c                                              21

<210> SEQ ID NO 76
<211> LENGTH: 21
<212> TYPE: DNA
<213> ORGANISM: Artificial
<220> FEATURE:
<223> OTHER INFORMATION: Primer

<400> SEQUENCE: 76
acctcacaga ttccagcttc g                                              21

<210> SEQ ID NO 77
<211> LENGTH: 23
<212> TYPE: DNA
<213> ORGANISM: Artificial
<220> FEATURE:
<223> OTHER INFORMATION: Primer

<400> SEQUENCE: 77
tttcatagta taagtgtctt ttt                                            23

<210> SEQ ID NO 78
<211> LENGTH: 20
<212> TYPE: DNA
<213> ORGANISM: Artificial
<220> FEATURE:
<223> OTHER INFORMATION: Primer

<400> SEQUENCE: 78
tggaacagcc cttctaccac                                                20

<210> SEQ ID NO 79
<211> LENGTH: 20
<212> TYPE: DNA
<213> ORGANISM: Artificial
<220> FEATURE:
<223> OTHER INFORMATION: Primer

<400> SEQUENCE: 79
ctcaggagca tgggdataaa                                                20

<210> SEQ ID NO 80
<211> LENGTH: 20
<212> TYPE: DNA
```

```
<213> ORGANISM: Artificial
<220> FEATURE:
<223> OTHER INFORMATION: Primer

<400> SEQUENCE: 80
cgttccacag gccaagtgcg                                                      20

<210> SEQ ID NO 81
<211> LENGTH: 20
<212> TYPE: DNA
<213> ORGANISM: Artificial
<220> FEATURE:
<223> OTHER INFORMATION: Primer

<400> SEQUENCE: 81
gctggtgcgc actagtactg                                                      20

<210> SEQ ID NO 82
<211> LENGTH: 21
<212> TYPE: DNA
<213> ORGANISM: Artificial
<220> FEATURE:
<223> OTHER INFORMATION: Primer

<400> SEQUENCE: 82
tgatggtaca tgacaaggtg c                                                    21

<210> SEQ ID NO 83
<211> LENGTH: 20
<212> TYPE: DNA
<213> ORGANISM: Artificial
<220> FEATURE:
<223> OTHER INFORMATION: Primer

<400> SEQUENCE: 83
acagtccatg ccatcactgc                                                      20

<210> SEQ ID NO 84
<211> LENGTH: 6
<212> TYPE: PRT
<213> ORGANISM: Homo sapiens

<400> SEQUENCE: 84

Thr Leu Val Val Leu His
1               5
```

METHODS FOR SCREENING INHIBITORS OF TUMOR ASSOCIATED PROTEIN AGGREGATION

CROSS-REFERENCE TO RELATED APPLICATIONS

This application is a national phase entry under 35 U.S.C. §371 of International Patent Application PCT/EP2012/055291, filed Mar. 26, 2012, designating the United States of America and published in English as International Patent Publication WO 2012/130785 A1 on Oct. 4, 20121, which claims the benefit under Article 8 of the Patent Cooperation Treaty and under 35 U.S.C. §119(e) to U.S. Provisional Patent Application Ser. No. 61/465,892, filed Mar. 25, 2011.

STATEMENT ACCORDING TO 37 C.F.R. §1.821(c) or (e)—SEQUENCE LISTING SUBMITTED AS A TXT AND PDF FILES

Pursuant to 37 C.F.R. §1.821(c) or (e), a file containing a TXT version and a PDF version of the Sequence Listing has been submitted concomitant with this application, the contents of which are hereby incorporated by reference.

TECHNICAL FIELD

The disclosure relates to the fields of biotechnology, medicine, and protein aggregation diseases including cancer. More specifically, it concerns a screening method for identifying compounds that inhibit or disrupt co-aggregation of one or more member proteins of a disease-related protein aggregome, in particular, a tumor-associated protein aggregome. Further, it encompasses agents and compounds identified by the screening method that can be applied to prevent or to treat protein aggregation diseases, such as cancer.

BACKGROUND

A growing number of diseases are associated with inappropriate depositions of protein aggregates, typically including neurological disorders and systemic amyloidoses.[1] During malignancy, proteins are usually uncontrollably overexpressed or structurally affected due to genetic mutations, resulting in changes in activity and protein-protein interactions in cancer cells.[2] A subset of neuroblastomas, carcinomas and myelomas show an abnolinal accumulation of tumor-suppressor p53 protein aggregates.[51, 19]

The tumor-suppressor p53 is a key regulator of the cell cycle and is mutated in approximately 50% of reported human tumor cases, making it a major target for anticancer therapy.[3] p53 is a transcription factor that acts as a homotetramer, with each monomer consisting of an N-terminal transactivation domain, a proline-rich domain, a central DNA-binding domain, a tetramerization domain and a C-terminal regulatory domain (FIG. 1). According to IARC TP53 Mutation Database,[4] over 95% of the malignant mutations occur in the DNA-binding domain where they cluster in so-called hot-spots of mutation.

Previously, it has been shown that the DNA-binding domain of p53 is conformationally unstable and that the majority of hot-spot disease mutants such as R175H, R282W, R248Q and R249S further destabilize the DNA-binding domain[5] (FIG. 1). Consequently, a proportion of these mutants are at least partially unfolded[6] and, therefore, inactive. Hence, these mutants, present in about 30% of reported clinical cases,[7] are usually referred to as "structural" mutants. A second class of disease mutants, such as R273H and R248W, which are present at the p53 DNA-binding interface, affect DNA binding without affecting the conformational stability of the domain, and are, therefore, referred to as "contact" mutants, representing about 20% of cases.

As native p53 functions as a tetrameric protein, it is generally accepted that the dominant-negative effect arises from the incorporation of both inactive mutant and wild-type p53 molecules into mixed tetramers, resulting in a reduced cellular concentration of functional p53.[8]

Several biological mechanisms leading to gain of tumorigenic function of p53 mutants have been proposed,[9] and one pivotal mechanism seems to be the ability of mutant p53 to interact with and attenuate the function of its paralogues p63 and p73, whose transactivating isoforms have been demonstrated to inhibit tumor metastasis and increase the sensitivity for radiochemotherapies.[10, 11]

Since structural p53 mutants display a dominant gain-of-function phenotype, major effort has been invested in the development of therapeutic treatments that stabilize and, thus, reactivate mutant p53.[52, 18] For instance, it has been shown that the introduction of N239Y as a secondary mutation in the p53C DNA-binding domain augments the stability of several, but not all, p53 cancer mutants. Although favorable, this would only functionally restore a limited number of mutants. Several screens have been performed in order to identify drugs that stabilize structural p53 mutants and reactivate its transcriptional activity; two such promising and structurally unrelated compounds are PRIMA-1 (p53 reactivation and induction of massive apoptosis) and MIRA-1 (mutant p53 reactivation and induction of rapid apoptosis). Another notorious drug is the CP-31398 molecule that was claimed to rescue mutant p53. Despite the therapeutic potency of strategies stabilizing structural p53 mutants, it is noted that, in murine models, prolonged treatment might favor the development of p53-resistant tumors or result in premature aging in some murine models.

Other therapeutic strategies do not focus on stabilizing mutant p53, but on increasing the level of active wild-type p53 in heterozygous p53 mutant cancer cells. This is achieved by manipulating cellular regulators of p53, mostly Mdm2. Mdm2 is a negative regulator of p53, inhibiting p53 through at least two mechanisms: binding to the transcriptional activation domain of p53, thereby preventing transcription, and by promoting p53 ubiquitination and ultimate degradation. The MDM2 gene itself is a transcriptional target of p53, generating a negative feedback loop when p53 activity increases. Several compounds have been identified that target the physical interaction between p53 and Mdm2; examples include the 3G5 antibody that competes for the p53 binding site of Mdm2,[55] the microbial extract chlorofusin that binds Mdm2[56] and RITA (reactivation of p53 and induction of tumor cell apoptosis) that binds the N-terminus of p53 preventing its interaction with Mdm2.[57] Probably the most prominent inhibitors of the p53-Mdm2 interaction are the nutlins (Roche).[53, 54] The nutlins are small permeable compounds that bind to the p53 binding pocket of Mdm2 with $IC_{50}$ values in the nanomolar range. Currently, they are being evaluated in early clinical trials.

A different approach to augment the level of active wild-type p53 in heterozygous p53 mutant cancer cell is the introduction of wild-type p53 by means of adenoviral vectors. This already resulted in the development of several commercial medicines, like ADVEXIN™ (Introgen) and GENDICINE™ (Sibiono), the first anticancer gene therapy drug. Onyx-15 (Onyx Pharmaceuticals) is also based on an adenoviral vector, but instead of supplementing the cells with wild-type p53, it will specifically kill mutant cancer cells. However, it should be remarked that adenovirus-based gene therapy has several draw-backs: it is not expressed for long-term, has a limited packaging capacity to express other genes, and it spreads slowly and works poorly when injected intravenously. But, more importantly, adenoviruses, even inactivated, can prompt an immune response, which already resulted in the death of a patient treated with adenovirus gene therapy.

An alternative strategy in p53 cancer therapy focuses on the p53 homologues p63 and p73. p53, p63 and p73 share strong structural similarity; nonetheless, there seems to be functional diversity. For instance, aberrancies in p63 and p73 cause severe developmental abnormalities but no increased cancer susceptibility like p53 mutants.[58] Nevertheless, p63 and p73 regulate cell cycle and apoptosis just like p53 and their inactivation is thought to contribute to metastasis. Consequently, current data has shown that an isoform of p73 functions as a tumor suppressor.[59] Mutant p53 interacts with p63 and p73 through the DNA-binding core domain.[60] A drug that breaks this oncogenic complex liberating p63 and p73 constitutes a favorable scenario for cancer treatment. Accordingly, it has recently been shown that disruption of the mutant p53 and p73 complex by small peptides consequently restores p73 activity.[61] Notwithstanding this potential, such a strategy is severely complicated by the occurrence of many isoforms of p63 and p73 and the residing unclearness about the exact role of p63 and p73 in tumor progression.

There is thus a need for alternative strategies to combat cancer, without any of the aforementioned problems.

DISCLOSURE

It remains largely unexplored whether aggregation of tumor suppressors and/or oncogenes could contribute to the induction or progression of malignancy. However, it might open up new avenues for individualized therapeutic intervention.

It has been surprisingly found that the dominant-negative activity and gain-of-function effects of structurally destabilized p53 mutants result from the increased aggregation propensity of these mutants. It was found that misfolded mutant p53 exposes a short aggregation-prone peptide sequence (termed p53β), also referred to as "beta-aggregating region," that interacts with various proteins whose only common denominator is the fact that they contain a similar sequence fragment. These aggregation-specific protein-protein interactions lead to a functional inactivation through co-aggregation with mutant p53. As such, mutant p53 not only induces co-aggregation of its homologs p63 and p73, but also of several unrelated proteins including copine-2 and caspase-8, the inactivation of which is pro-proliferative and anti-apoptotic, respectively. Thus, misfolded mutant p53 forms a specific interactome of aggregation-specific interactions, or tumor-associated aggregome, thereby exhibiting pro-proliferative gain-of-function activities by the superposed inactivation of multiple proteins in both antiproliferative and pro-apoptotic pathways.

The data reveal that p53-missense-associated cancer development is an aggregation disease and evoke the exploration of innovative therapeutic strategies that abrogate or inhibit mutant p53-mediated aggregation. This is believed to be a novel concept and new approach in the combat against mutant p53-provoked tumor progression.

Interestingly, evidence is provided that this concept of aggregation-specific protein-protein interactions is more widely applicable, since it was demonstrated that other tumor-suppressor proteins (e.g., PTEN, p16) exposing an aggregation-prone peptide sequence (PTENβ or p16β, respectively) may also form co-aggregates with various proteins harboring a homologous aggregation-prone peptide sequence.

Moreover, evidence is provided that the above mutant p53-based concept of aggregation can be extrapolated to aggregation propensity of non-aggregation-prone p53 contact mutants or wild-type p53 in certain tumor contexts. It was surprisingly found that upon its induction by genotoxic stimuli, increased expression of p53 in tumor cell lines harboring wild-type p53 also resulted in the generation of cytoplasmic aggregates, comparable to a proteostatic collapse. This also resulted in co-aggregation with the other p53 family members and some pro-apoptotic and antiproliferative proteins. Overall, even wild-type p53 can become an oncogene by co-aggregation when its expression levels are deregulated.

The applicants' work has led them to produce screening methods in order to detect molecules that interfere with the aggregation behavior of member proteins of tumor-associated protein aggregomes. As an illustration, a screening method was developed to detect molecules that, for example, inhibit the aggregation of mutant p53 or disrupt the aggregation between a dominant-negative mutant p53 and wild-type p53 (or another wild-type member protein of the p53 aggregome). A compound that can maintain functional p53 wild-type (or another wild-type member protein of the p53 aggregome) in the presence of an aggregating mutant would, in principle, constitute an attractive therapeutic drug for the treatment of p53 tumors.

Accordingly, in a first aspect, the disclosure relates to a method for screening for a compound that inhibits or disrupts co-aggregation of one or more member proteins of a tumor-associated protein aggregome, wherein the method comprises the following steps:

a. Providing a cell expressing both an aggregation-prone engineered member protein and one or more wild-type member proteins of the protein aggregome; or b. Alternatively, providing a cell expressing one or more wild-type member proteins of the protein aggregome in the presence of a chemical agent, such as a chemotherapeutic agent;

c. Contacting the cell with a candidate compound; and d. Measuring the amount of co-aggregation of one or more member proteins of the protein aggregome and/or the activity of one or more wild-type member proteins of the protein aggregome;

wherein the co-aggregation is mediated by the exposure of a beta-aggregating region that is present in the member proteins, the beta-aggregating region comprising an amino acid sequence as follows:

a stretch of 4 to 16 contiguous amino acids, at least 50% of which are hydrophobic amino acids, and in which at least one aliphatic residue or F is present, and if only one aliphatic residue or F is present, at least one, and preferably at least two, other residues are selected from Y, W, A, M and T; and in which no more than 1, and preferably no P, R, K, D or E residue is present.

According to specific embodiments, the above-described method further comprises one or more of the following steps:

a. measuring the degree of degradation of one or more wild-type member proteins and aggregation-prone engineered member protein of the protein aggregome; or b. measuring cell survival; or c. measuring sensitivity to chemotherapeutic agents.

Preferably, the tumor-associated protein aggregome as referred to in any of the above-described methods is a tumor-suppressor protein aggregome. In particular, the tumor-suppressor aggregome is chosen from the group comprising a p53 aggregome, a PTEN aggregome, a p16 aggregome and a pRb aggregome, and wherein a. member proteins of a p53 aggregome are chosen from the group comprising p53, p63, p73, copine-2, caspase-8;
b. member proteins of a first PTEN aggregome are chosen from the group comprising PTEN, tensin-3;
c. member proteins of a second PTEN aggregome are chosen from the group comprising PTEN, oxidative stress-induced growth inhibitor 1; and
d. member proteins of a p16 aggregome are chosen from the group comprising p16, p15.

Preferably, the aggregation-prone engineered member protein as referred to in any of the above-described screening methods is a mutated tumor-suppressor protein such as a mutated p53 carrying a mutation chosen from the group comprising R110P, R110L, R175H, Y220C, G245S, R248Q R249S, P250L, E258V, R282W, or a mutated p16 carrying a mutation such as S56I, or a mutated PTEN carrying a mutation such as PTEN 800 delA, R173C, R173P. In an alternative preferred embodiment, the aggregation-prone engineered member protein is a fusion protein of a wild-type member protein fused to a protein, in particular, a detectable protein, such as a fluorescent protein.

A second aspect of the disclosure relates to an agent or compound identified by any of the above-described methods for use in the prevention and/or treatment of cancer. According to specific embodiments, the agent or compound can be particularly useful in the prevention and/or treatment of cancer in a subpopulation of subjects having a structural destabilizing mutation in a tumor-suppressor protein, and/or in a subpopulation of subjects under treatment with chemotherapeutic agents, and/or in a subpopulation of subjects suffering from a reduction in proteostatic capacity.

Further, also disclosed is a pharmaceutical composition comprising an agent or compound as described above, together with a pharmaceutically acceptable carrier, diluent, and/or excipient.

Finally, the disclosure also envisages a method for screening for a new member protein of a tumor-associated protein aggregome indicative for a disease, in particular, cancer, comprising the following steps:

a. Identifying in at least one protein at least one region of 4 to 16 contiguous amino acids, at least 50% of which are hydrophobic amino acids, and in which at least one aliphatic residue or F is present, and if only one aliphatic residue or F is present, at least one, and preferably at least two, other residues are selected from Y, W, A, M and T; and in which no more than 1, and preferably no P, R, K, D or E residue is present;
b. Contacting the protein identified in step a with an aggregation-prone engineered member protein of a tumor-associated protein aggregome; and
c. Assessing the aggregation and/or function of the protein of step a.

According to a preferred embodiment, the new member protein identified by the above-described method is a novel target for the treatment of cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Only the T256R mutation (indicated) reduced the TANGO score by 70%, while leaving the free energy unaffected. Panel b: Co-IP of mutant and wild-type p53 suggested that T265R did not suppress the interaction between aggegated mutant and the wild-type. Panel c: BN-PAGE revealed that the T256R mutation did not prevent the aggregation of R175H mutant, explaining the choice for I254R as mutation used throughout the manuscript.

Figure 7:
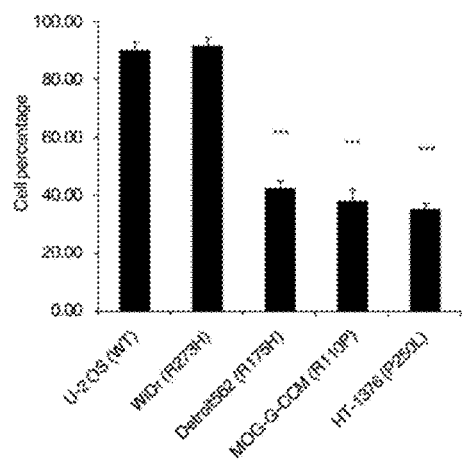

FIG. 7: Immunostain of p53 aggregates in tumor cell lines and tissues. Statistical analysis of p53 localization in cell lines, showing the percentage of cells with predominantly nuclear staining. Data represent mean values±s.d. (n=3). ***P<0.001 (student t-test).

Figure 8:
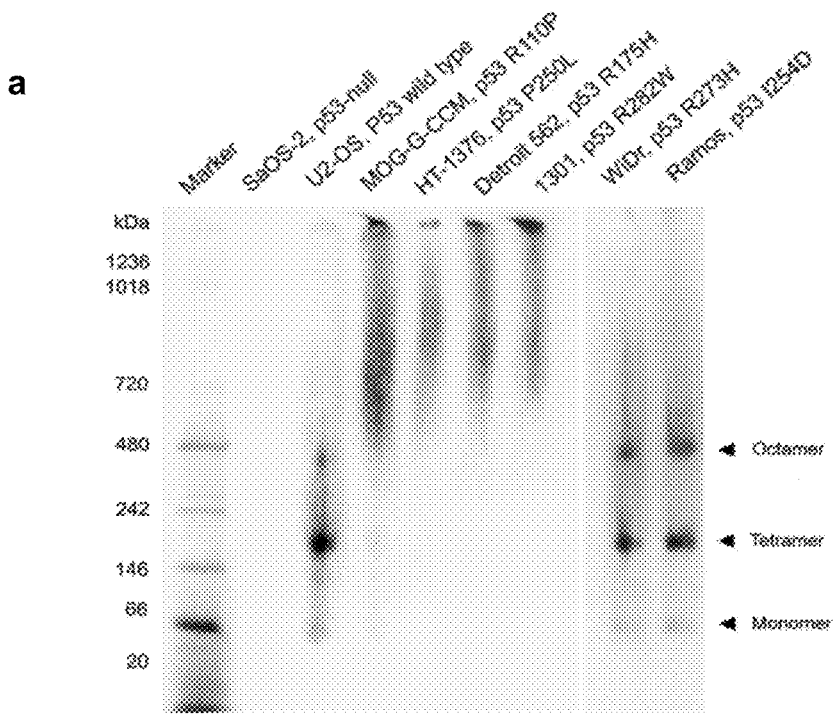
Figure 8:
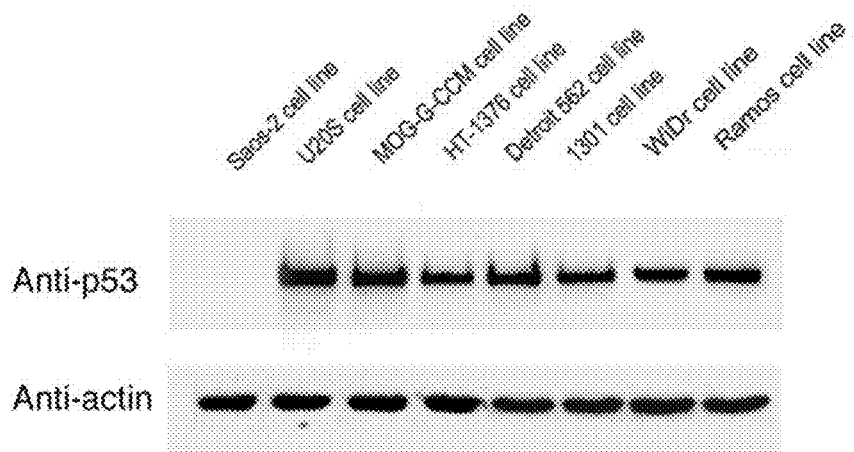

FIG. 8: Aggregation of endogenously expressed p53 in tumor cell lines and tissues. Panel a: Native-PAGE of wild-type and mutant p53 endogenously expressed in human tumor cell lines. Being consistent with the over-expression experiment, the endogenously expressed wild-type p53 and mutants R273H and I254D formed monomer, tetramer and octamer, whereas the mutants R110P, P250L, R175H and R282W formed high molecular-weight aggregates. Panel b: In SDS-PAGE, p53 showed comparable expression level in the tumor cell lines (upper panel). Actin was detected as loading control (lower panel).

Figures 9, 10:
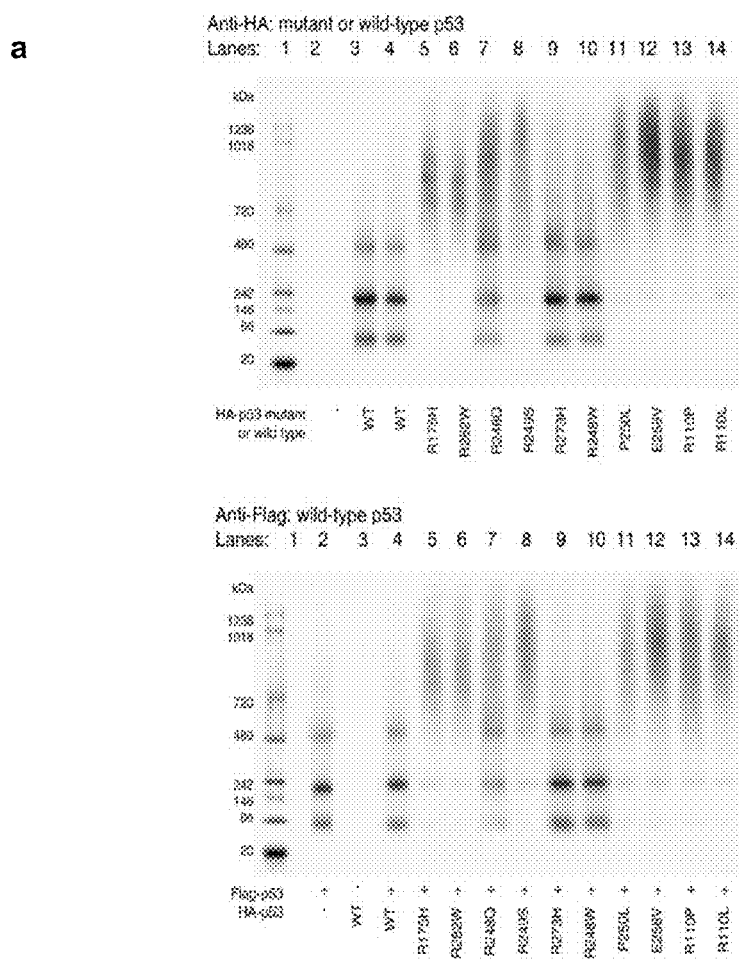
Figure 10:
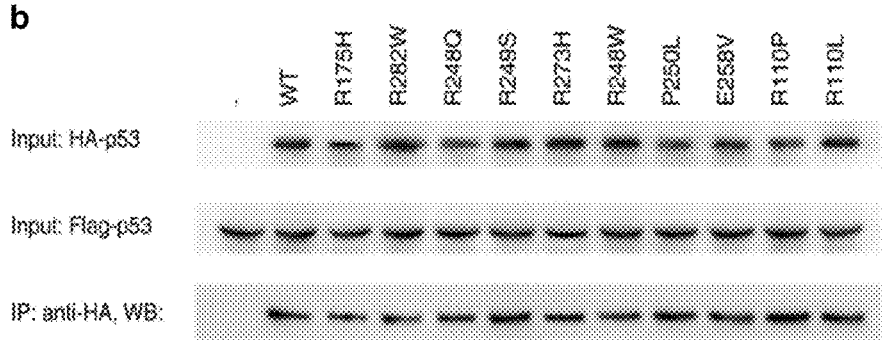
Figure 10:
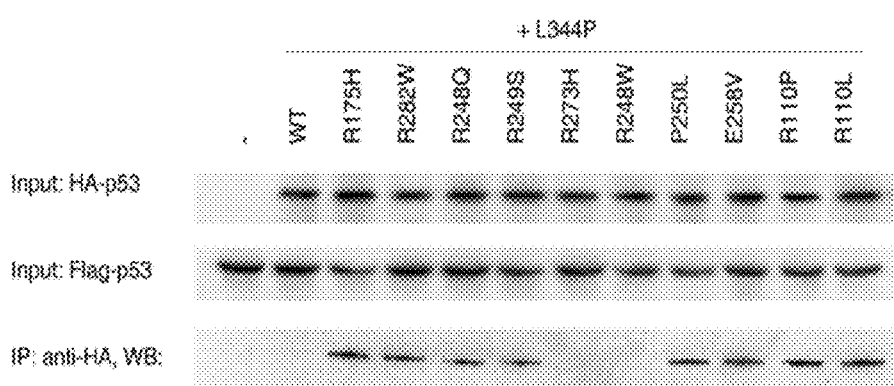

FIG. 9: Genotype and subcellular localization of p53 in human colon adenocarcinomas.

FIG. 10: Mutant p53 induced co-aggregation of wild-type p53 and caused dominant-negative activity. Panel a: Blue Native-PAGE of mutant p53 (upper panel) and wild-type (lower panel) co-expressed in SaOS-2 cells. In the presence of aggregating mutants, the WT protein shifted to higher molecular weight and co-migrated with the mutant. Panel b: Co-immunoprecipitation of HA-tagged mutant p53 and the FLAG-tagged wild-type p53. Physical interaction between wild-type p53 and all mutants with intact tetramerization domain (upper panel), but only the aggregating mutants were still able to bind the WT when hetero-tetramerization was inhibited by the L344P mutation (lower panel).

Figure 11:
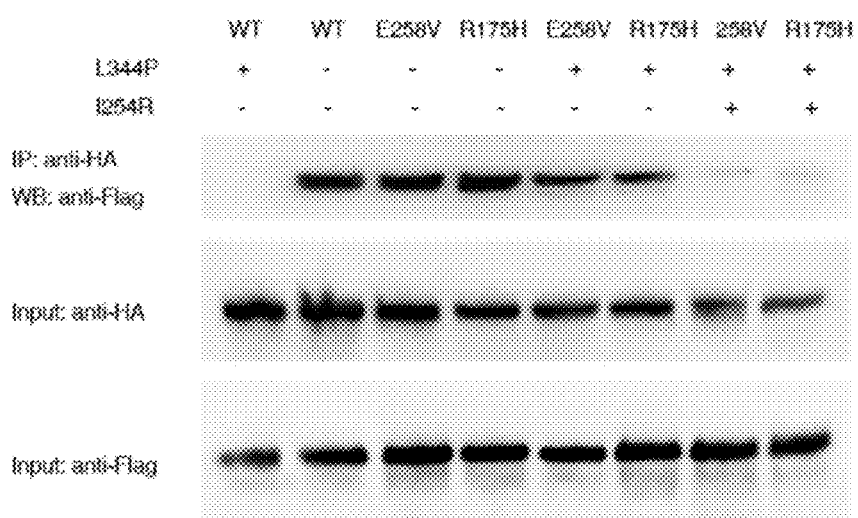

FIG. 11: Suppression of p53 mutant aggregation by designed charged residues. Co-immunoprecipitation of mutant (HA-tagged) and wild-type (FLAG-tagged) p53. In the presence of L344P mutation, the aggregating mutants E258V and R175H still physically interacted with WT, but the aggregation-suppressing mutation I254R abolished the interaction between aggregating mutants (E258V and R175H) and wild-type.

Figure 12:
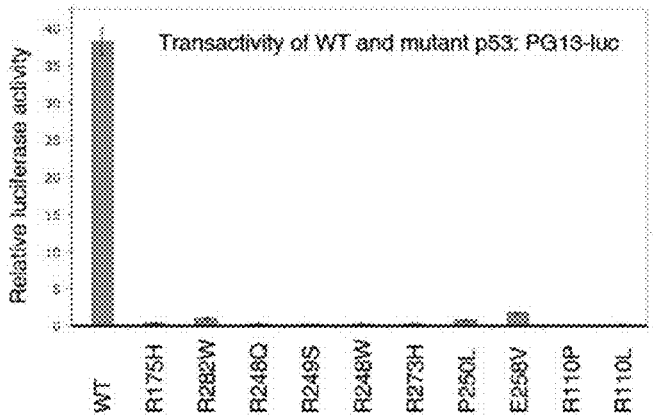
Figure 12:
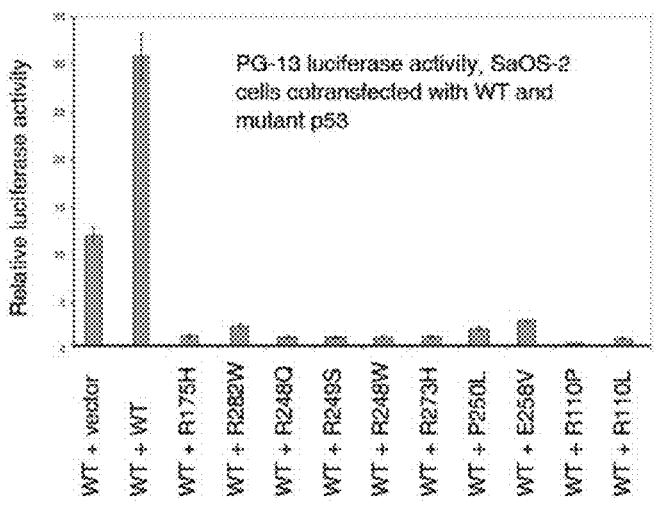
Figure 12:
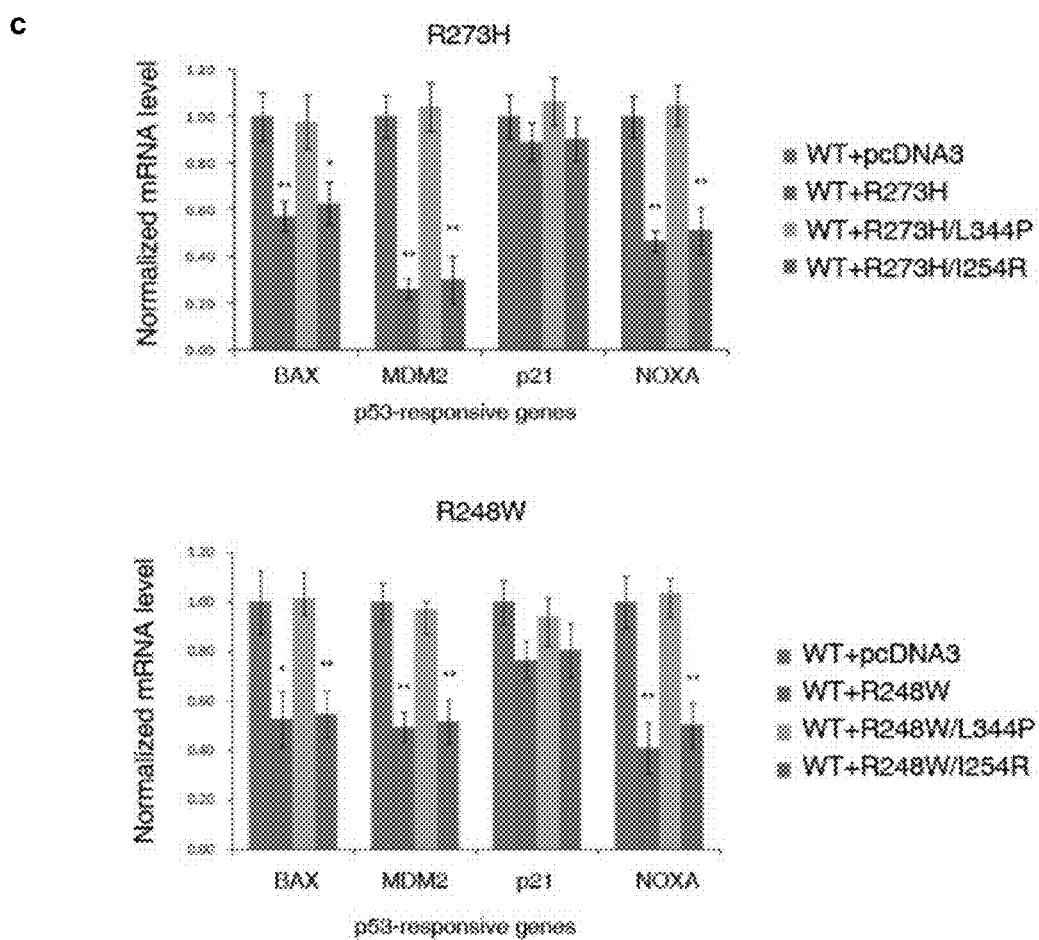
Figure 12:
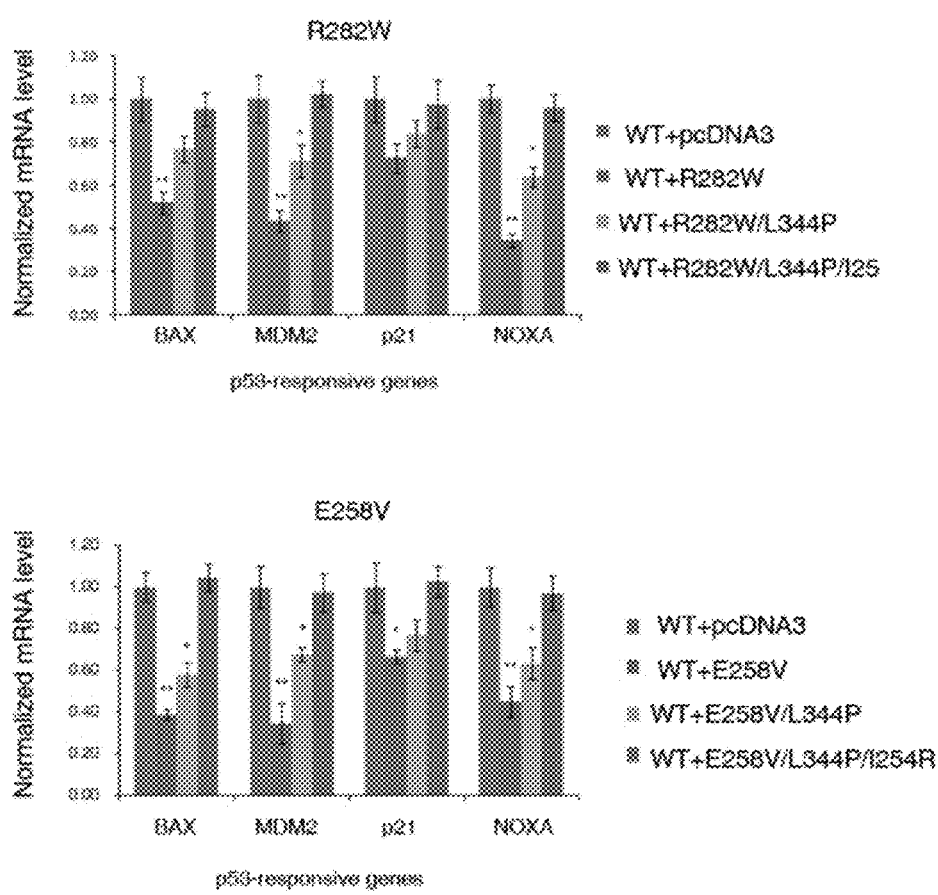
Figure 12:
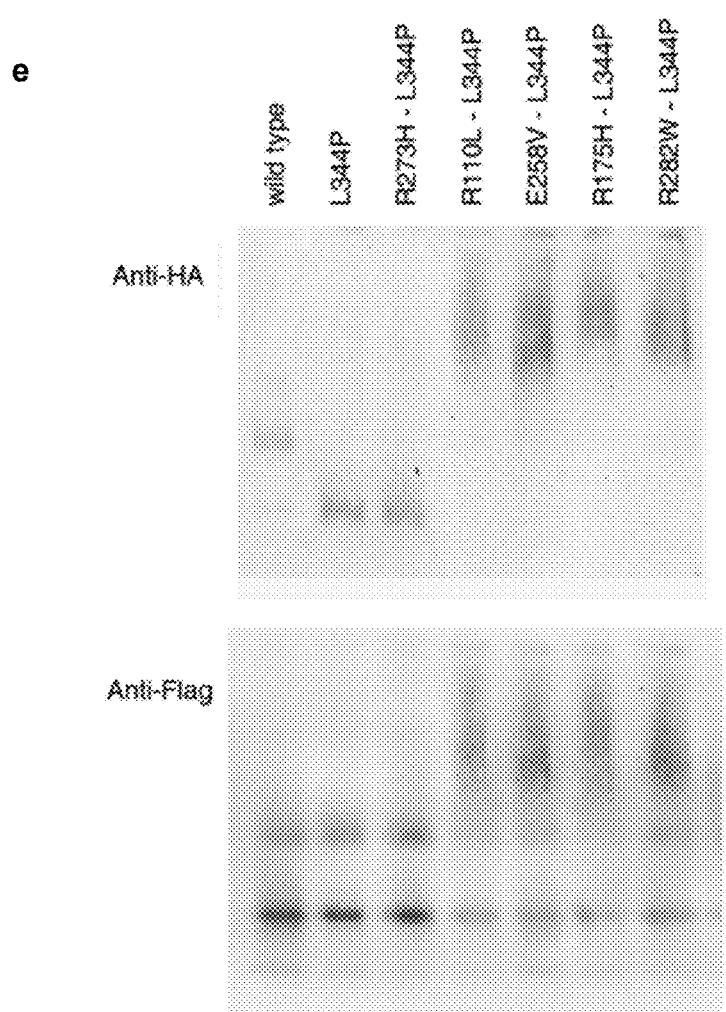

FIG. 12: Dominant-negative effects caused by tetramerization and aggregation. Panel a: Transcriptional function of wild-type and mutant p53 as determined by the PG-13 luciferase reporter assay. Panel b: SaOS-2 cells were co-transfected with wild-type, mutant p53 and PG-13 luciferase reporter. All mutants showed interference on wild-type function in the presence of intact tetramerization domain. Panel c: SaOS-2 cells co-expressing wild-type p53 and contact mutant (R273H or R248W) were analyzed for the RNA levels of MDM2, BAX, p21 and NOXA by qPCR. All conditions were compared to WT+pcDNA3. All qPCR data represent mean values±s.d. (n=4). *P<0.05; **P<0.01 (student t-test). Panel d: qPCR assay showing the dominant-negative effects of p53 structural mutants (R282W and E258V) affected by monomeric mutation L344P and aggregation-suppressing mutation I254R. Panel e: In BN-PAGE, the presence of L344P mutation abolished the tetramerization of wild-type p53 and R273H mutant but did not affect the aggregation of mutants R110L, E258V, R175H and R282W (upper panel), which induced the co-aggregation of wild-type p53 (lower panel).

Figure 13:
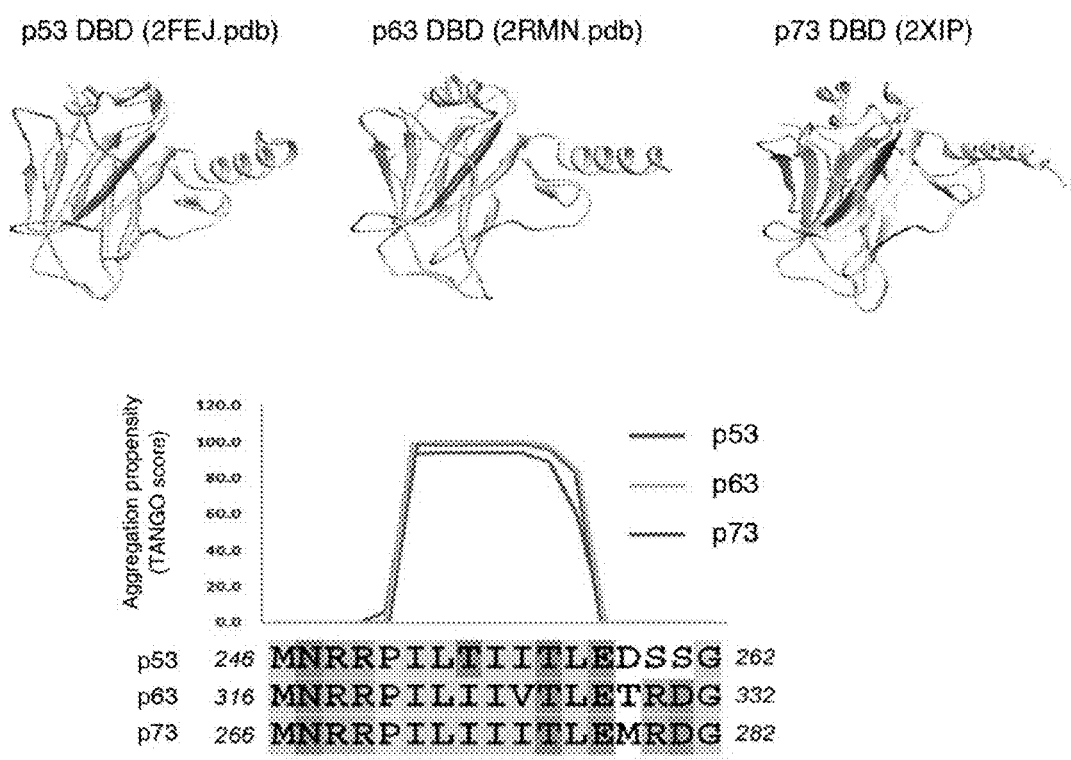

FIG. 13: Structural basis for the co-aggregation of p53 with p63 and p73. The experimentally determined structures of the DNA-binding domains of p53, p63 and p73 show high homology, with aggregating sequences in the same structural motif (marked in red). The TANGO analysis combining sequence alignment revealed that the aggregating sequences of p53 (251-257), p63 (321-327) and p73 (271-277) sit in a highly conserved region of DNA-binding domain.

Figure 14:
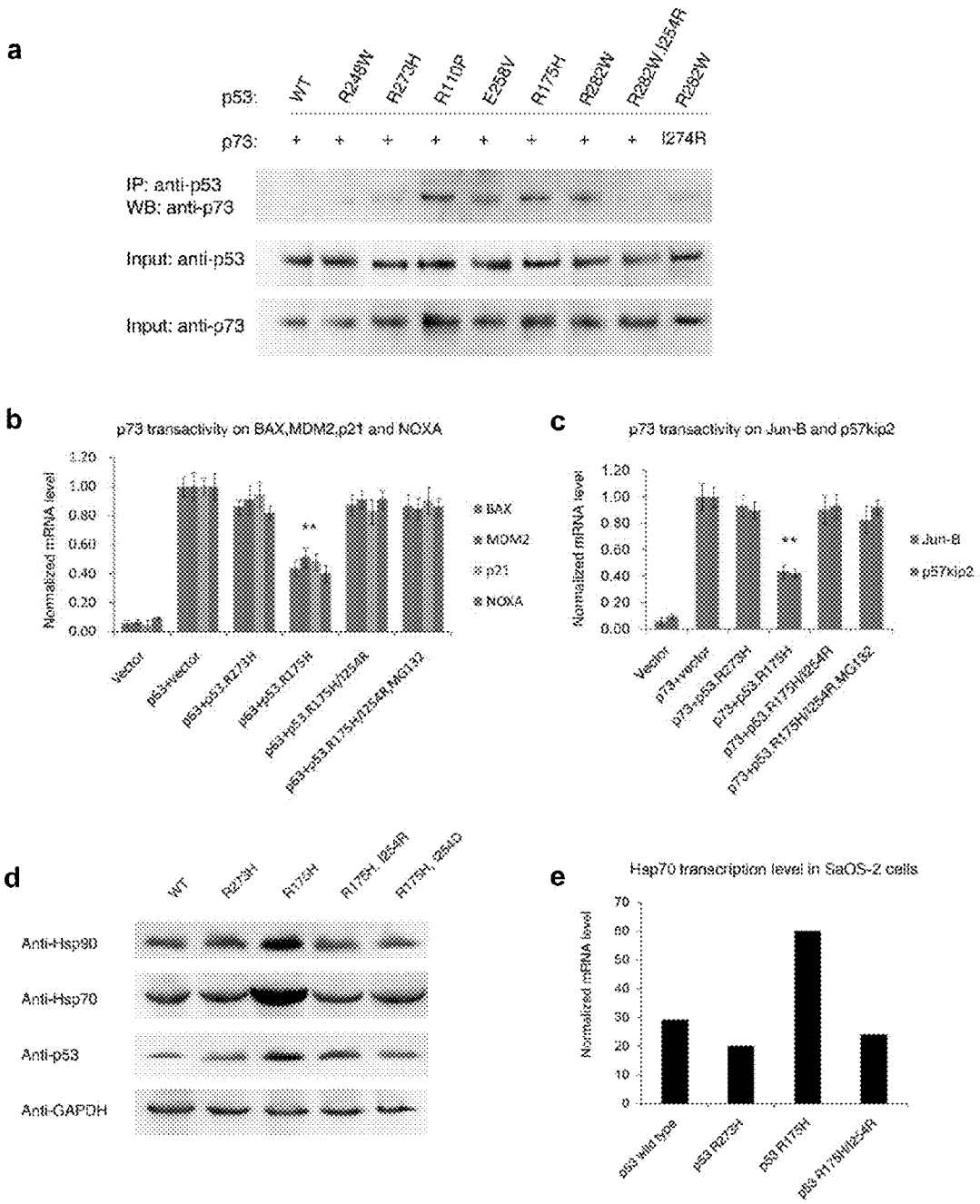

FIG. 14: Mutant p53 interacted and interfered with p73 through co-aggregation. Panel a: Co-immunoprecipitation of mutant p53 and p73 over-expressed in SaOS-2 cells. The structurally destabilizing mutants R110P, R175H and R282W showed strong interaction with p73, which was not observed for wild-type p53 and contact mutant R273H. The aggregation-suppressive mutations of p53 (I254R) and p73 (I274R) disrupted the interaction between mutant p53 and p73. Panels b and c: The co-expression of p53-aggregating mutant R175H significantly inhibited the transactivity of p73 on p53-responsive genes (panel b) and Jun-B and $p57^{kip2}$ (panel c), whereas the introduction of I254R mutation into p53 R175H, in both absence and presence of MG-132, successfully abolished its interference on p73 functions. Data represent mean values±s.d. (n=4). **P<0.01 (student t-test). Panel d: Over-expression of the aggregating mutant R175H induced substantial responses of Hsp90 and Hsp70. The introduction of I254R and I254D mutations reduced heat-shock response caused by R175H mutant. Panel e: The mRNA encoding Hsp70 was up-regulated upon the expression of aggregating mutant R175H, while the I254R mutation abolished this effect.

Figure 15:
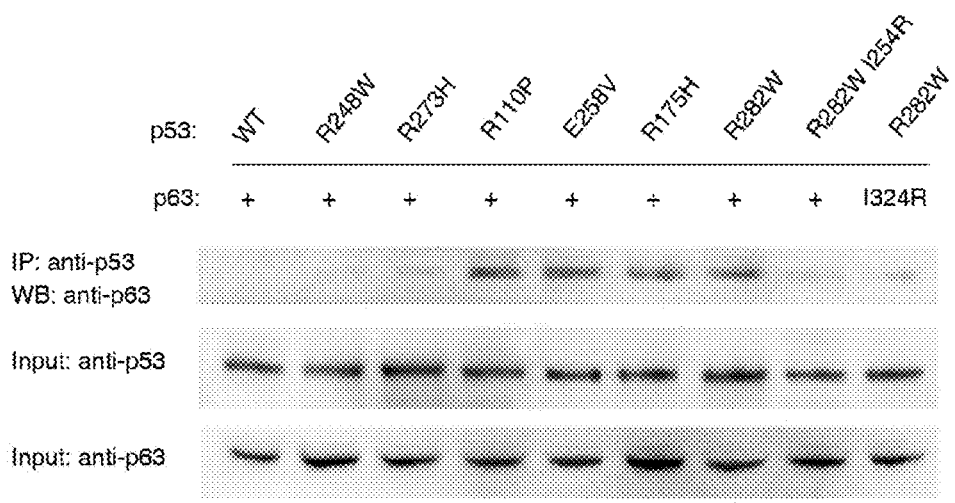
Figure 15:
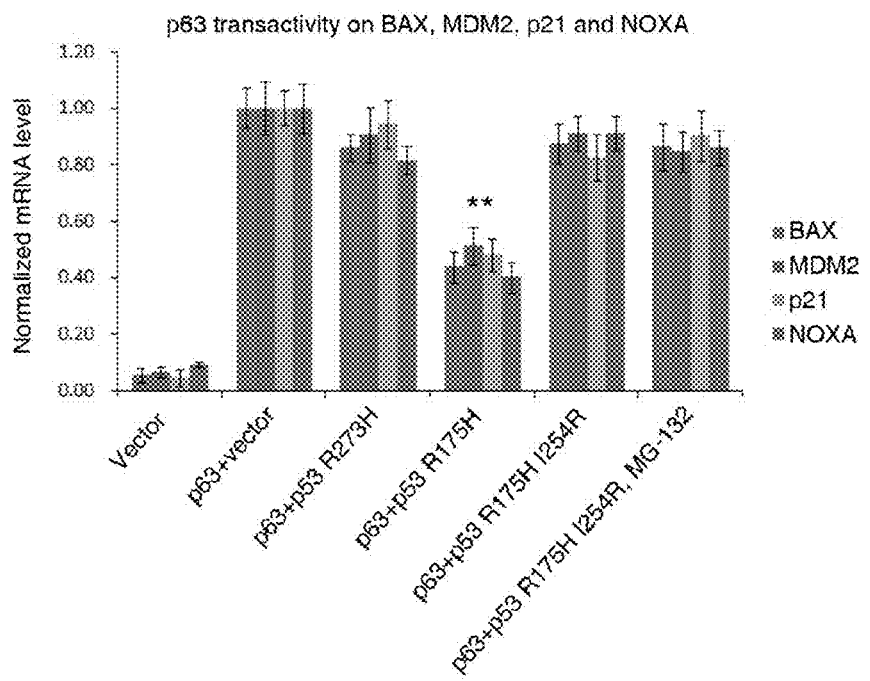

FIG. 15: Aggregated p53 mutants physically interacted with p63 and interfered with its function. Panel a: Co-immunoprecipitation of mutant p53 and p63. The aggregating p53 mutants R110P, E258V, R175H and R282W showed strong physical interaction with p63, which was not detected for WT p53 and contact mutants R248W and R273H. The charged mutations (p53 I254R and p63 I324R) significantly suppressed the interaction between p53-aggregating mutants and p63. Panel b: qPCR suggested that p53 mutant R175H significantly suppressed the transactivity of p63, whereas the introduction of I254R mutation abolished this effect in the absence and presence of MG-132.

Figure 16:
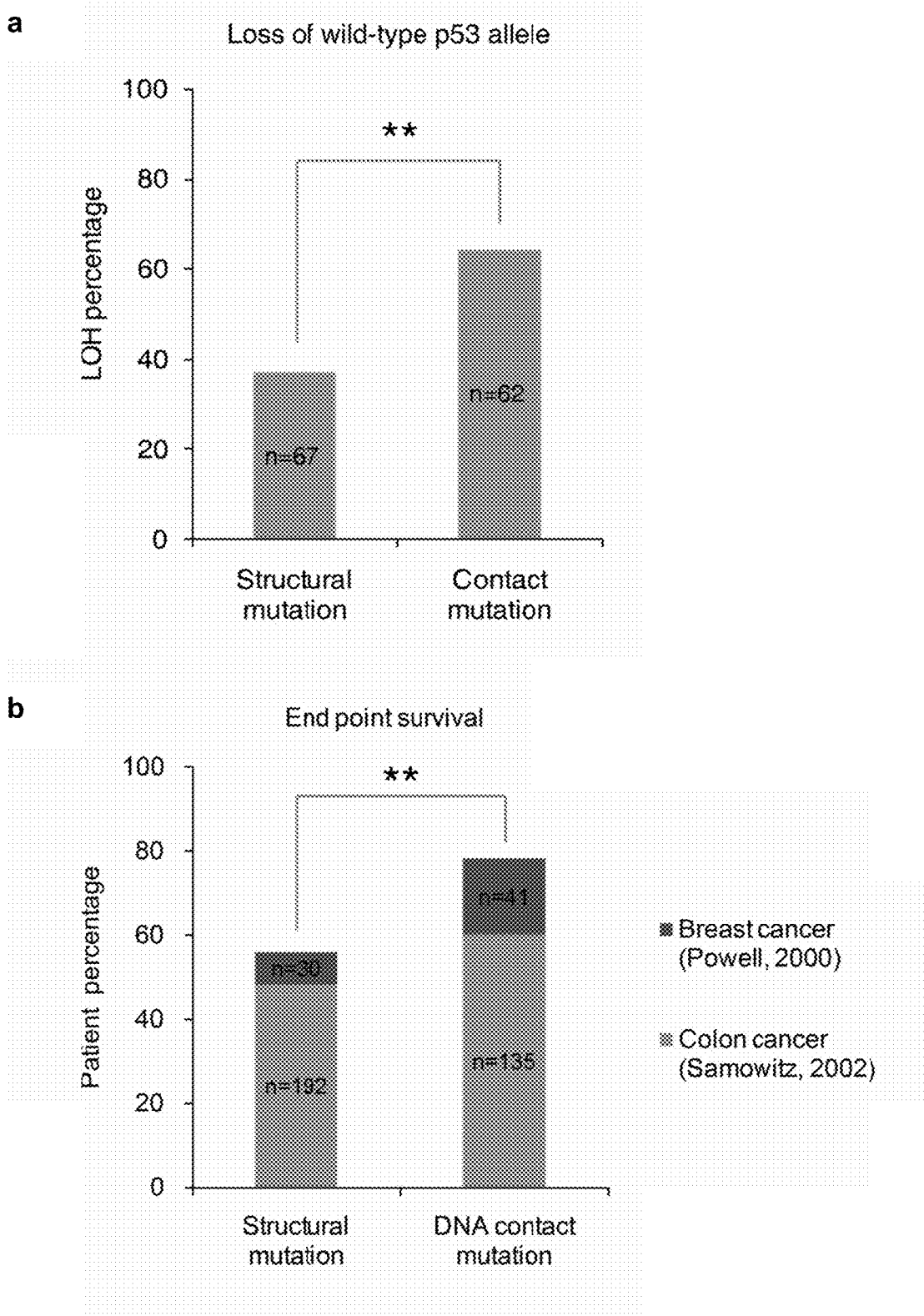

FIG. 16: Aggregation of mutant p53 linked to lower rate of LOH and patient survival. Panel a: Analysis on the p53 germline mutation database revealed a significantly higher rate of p53 LOH in tumors carrying DNA contact mutations (64.5%), compared to a lower rate in those carrying structural mutations (37.3%). P<0.01 (Chi-square test). Panel b: In two large-scale studies on prognosis of breast and colon cancers, the end-point survival of patients with DNA-contact mutations was significantly higher than those carrying aggregating mutations. P<0.01 (Chi-square test).

Figure 17:
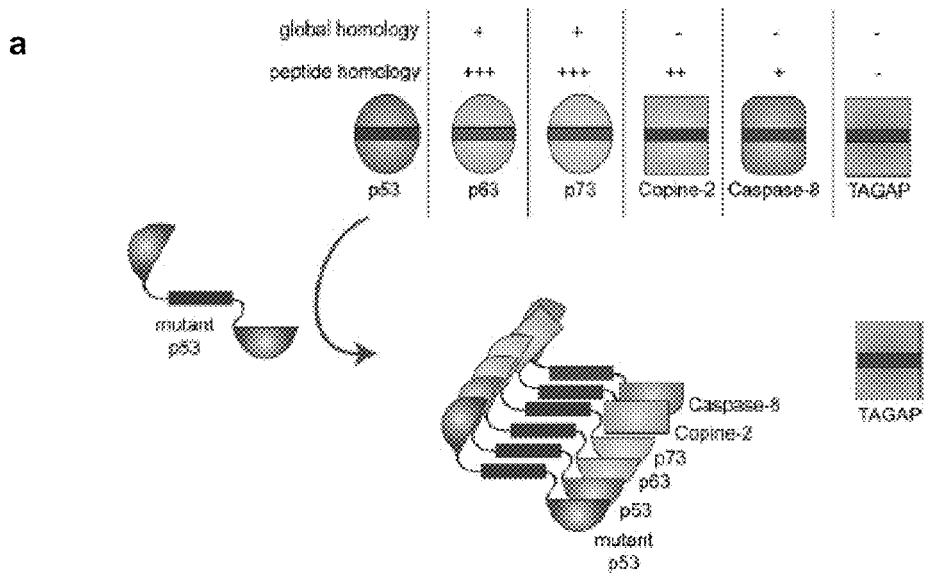
Figure 17:
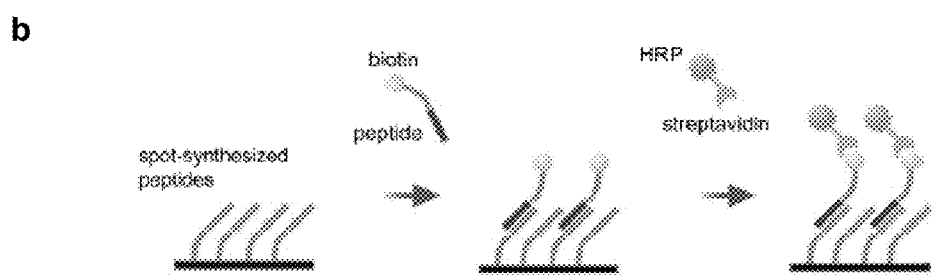
Figure 17:
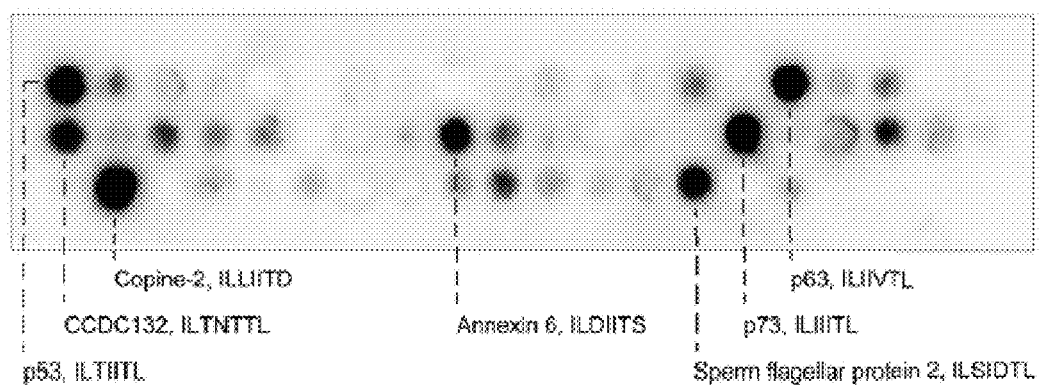

FIG. 17: Peptide-binding assay for the identification of co-aggregation sequences. Panel a: The proposed mechanism that drives the interaction between mutant p53 and target proteins that bear homologous aggregation-prone peptide sequences. The aggregation-nucleating sequence of p53 is labeled in red, which is shared by p63, p73, copine-2 and caspase-8, but not TAGAP. Mutations of p53 may destabilize the protein structure and expose its aggregating sequence, which mediates the association with p63, p73, copine-2 and caspase-8. Panel b: Schematic presentation of binding assay. Peptides to be screened were immobilized on membrane, and biotinylated p53-aggregating peptide was incubated with membrane, followed by binding with HRP-conjugated streptavidin and exposure. Panel c: Binding of p53-aggregating peptide with target peptides. The positions of immobilized peptides are labeled in upper panel, and the information of each peptide can be found in Table 2.

Figure 18:
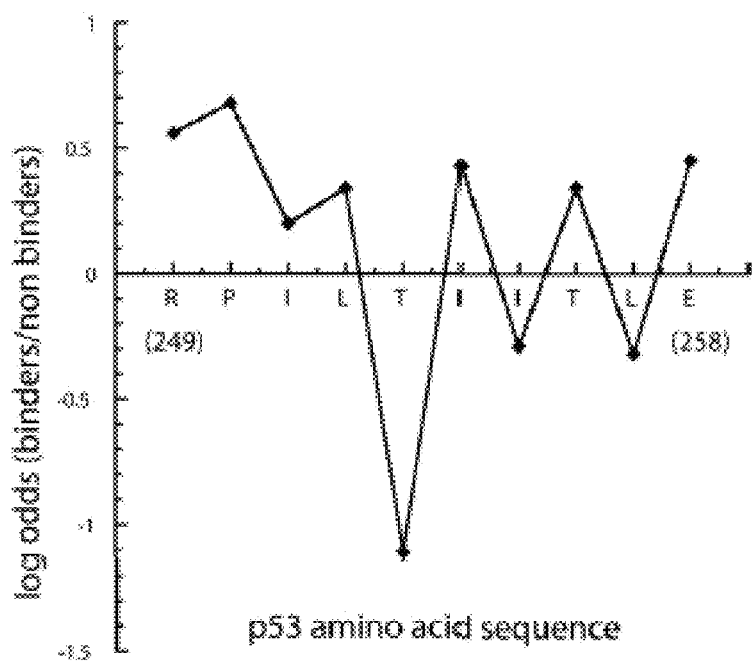
Figure 18:
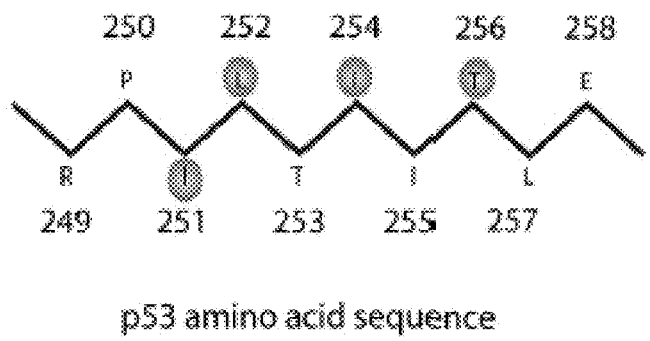

FIG. 18: Sequence specificity of coaggregated peptides is consistent with beta-sheet structure. Panel a: Sequence determinants of peptide co-aggregation by multiple sequence alignment and conservation scoring of the interacting and non-interacting target peptides. The X-axis indicates the position of residues, whereas the Y-axis shows the log odds of binder peptides against non-binder peptides. Panel b: Strong sequence conservation of I251, L252, I254 and T256 for the interacting peptides and low conservation in the intervening positions. With the exception of Ile251, the conserved residues cluster to a structurally conserved beta-sheet interface whereas the variable residues form the opposing variable beta-sheet interface.

Figure 19:
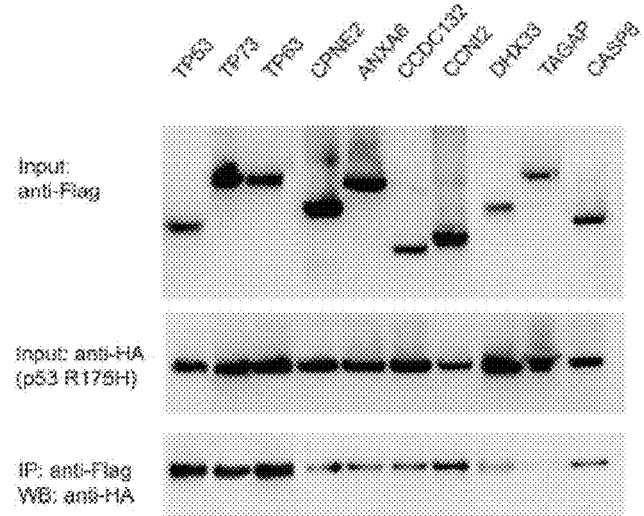
Figure 19:
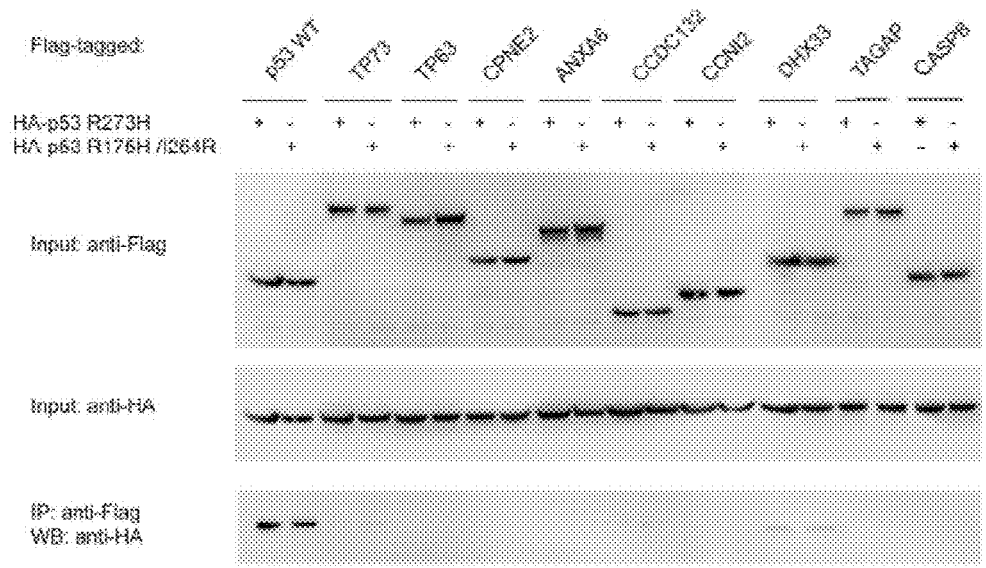

FIG. 19: Co-immunoprecipitation of mutant p53 and target proteins. HA-tagged p53 and FLAG-tagged target proteins were coexpressed in Hela cells, and target proteins were immunoprecipitated with specific antibody for FLAG tag. The co-immunoprecipitated mutant p53 R175H (panel a), R273H or R175H/I254R (panel b) were detected with anti-HA.

Figure 20:
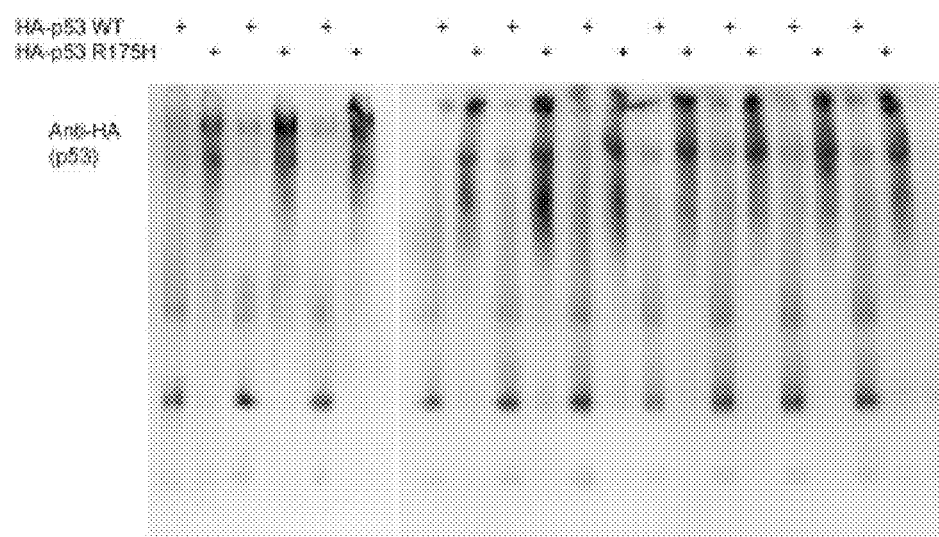
Figure 20:
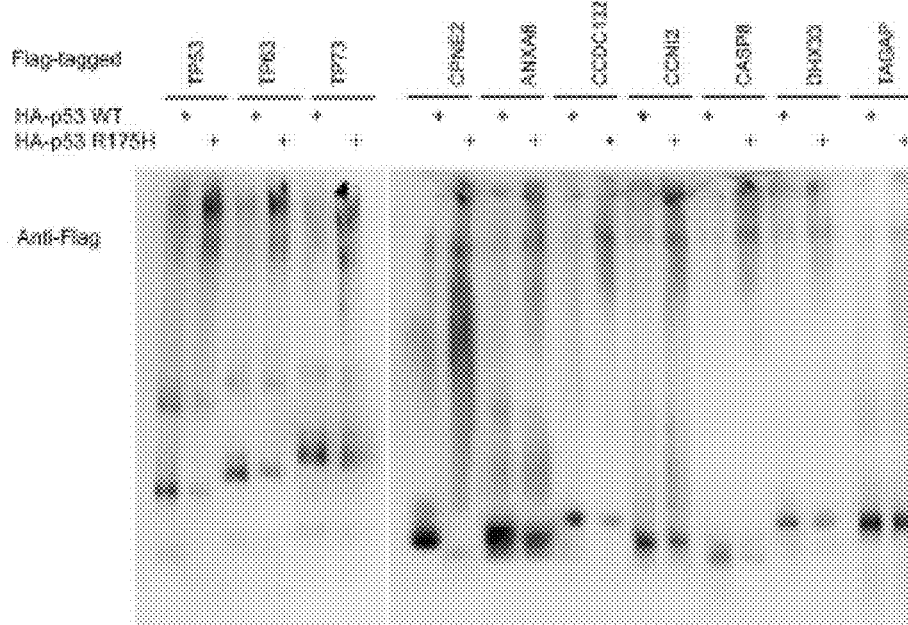
Figure 20:
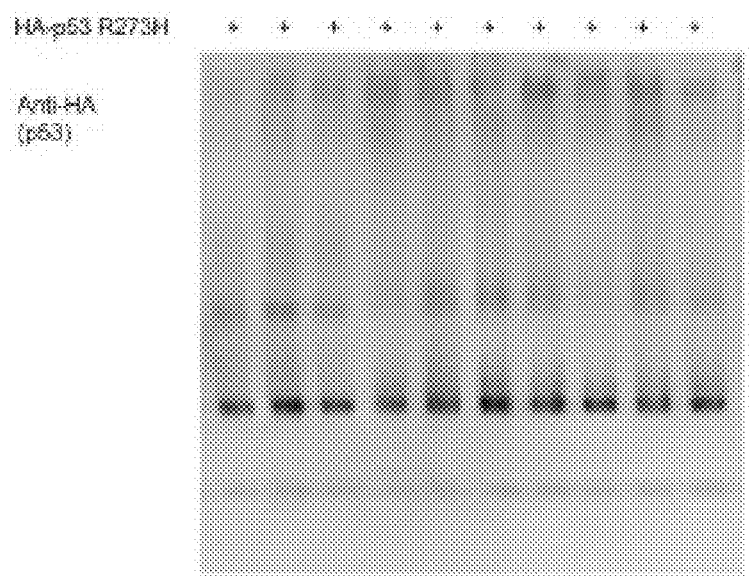
Figure 20:
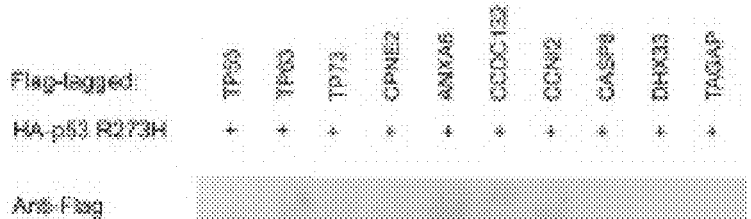

FIG. 20: Blue Native-PAGE (BN-PAGE) of HA-tagged p53 and FLAG-tagged target proteins coexpressed in Hela cells. Panels a and b: Each target protein was coexpressed with wild-type p53 or R175H mutant, and the aggregation status of p53 R175H and target proteins were respectively detected by BN-PAGE. Panels c and d: Target proteins were coexpressed with p53 mutant R273H and analyzed by BN-PAGE.

Figure 21:
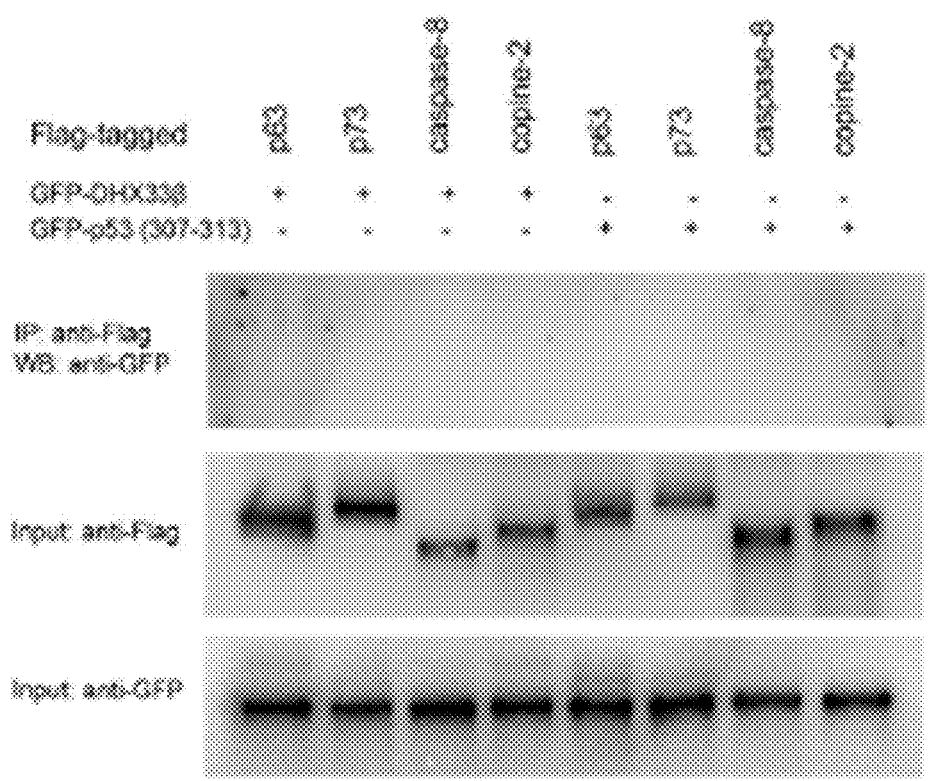

FIG. 21: Colocalization and interaction of p53β-GFP with target proteins. co-IP of GFP fusion proteins with target proteins coexpressed in Hela cells. The FLAG-tagged target proteins were immunoprecipitated, and the interacting GFP fusion protein was detected by antibody specific for HA tag.

Figure 22:
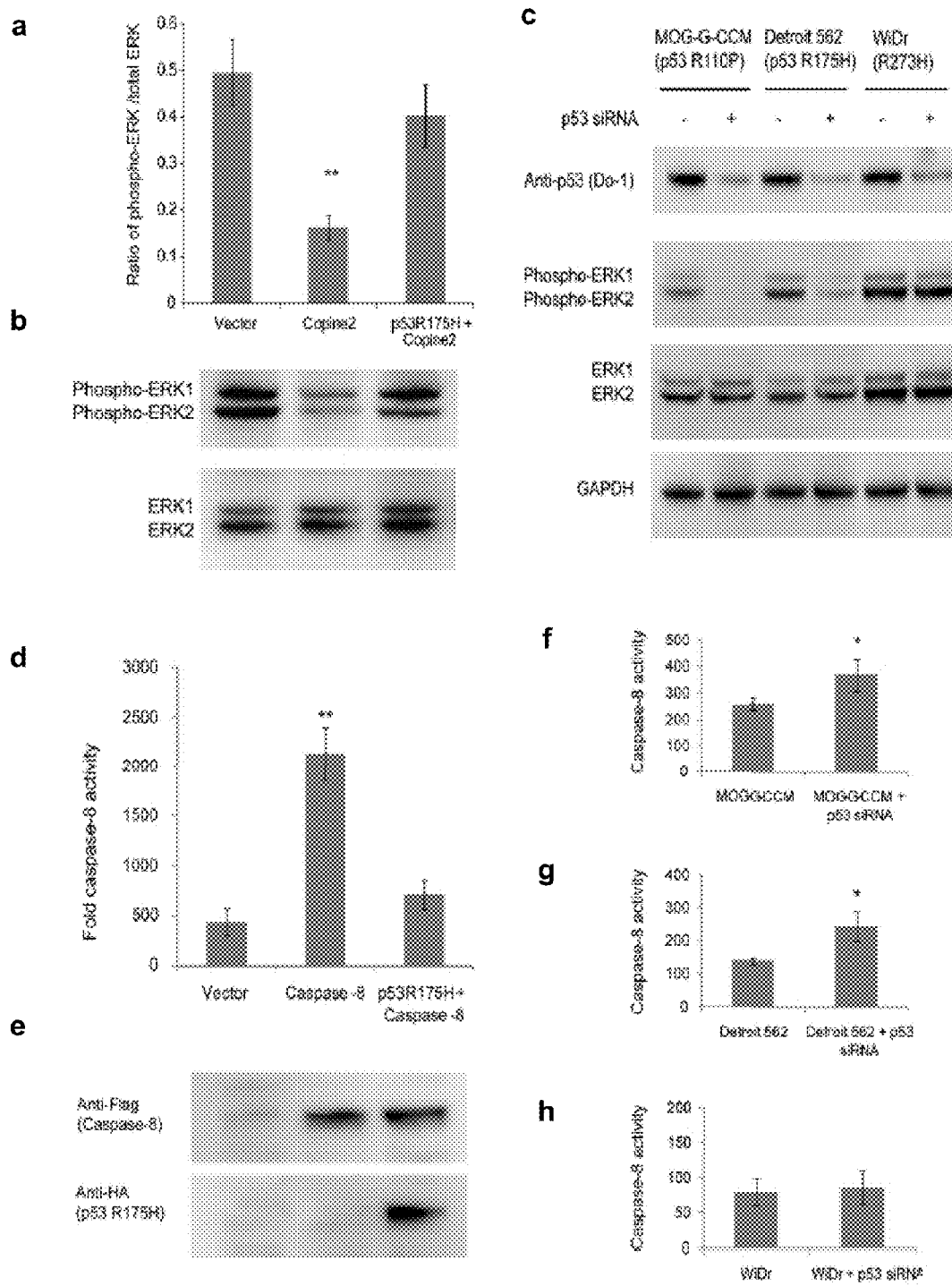

FIG. 22: Functions of copine-2 and caspase-8 modulated by mutant p53. Panel a: Phosphorylation of ERK1/2 affected by copine-2 and p53 mutant R175H. Hela cells expressing the empty vector, copine-2 or p53R175H plus copine-2 were analyzed for the ratio of phosphorylated ERK1/2 in total ERK1/2 using specific antibodies. Data represent mean values±s.d. (n=3). P<0.01 (student t-test). Panel b: Representative Western blots of phosphorylated ERK1/2 (p44 and p42) and total ERK1/2. Panel c: Phosphorylation of ERK1/2 in different tumor cell lines affected by RNAi of mutant p53. The MOG-G-CCM (p53 R110P), Detroit 562 (p53 R175H) and WiDr (p53 R273H) cells were transfected with p53 siRNA, and the levels of p53, GAPDH, phosphorylated ERK1/2 and total ERK1/2 were detected respectively. Panel d: Caspase-8 activity in Hela cells stably transfected with empty vector, caspase-8 without or with p53R175H. Data represent mean values±s.d. (n=3). P<0.01 (student t-test). Panel e: Expression level of exogenous caspase-8 and p53 mutant R175H in stably transfected Hela cells. Panels f through h: The activity of caspase-8 in cells treated as in panel c. Data represent mean values±s.d. (n=3). *P<0.05 (student t-test).

Figure 23:
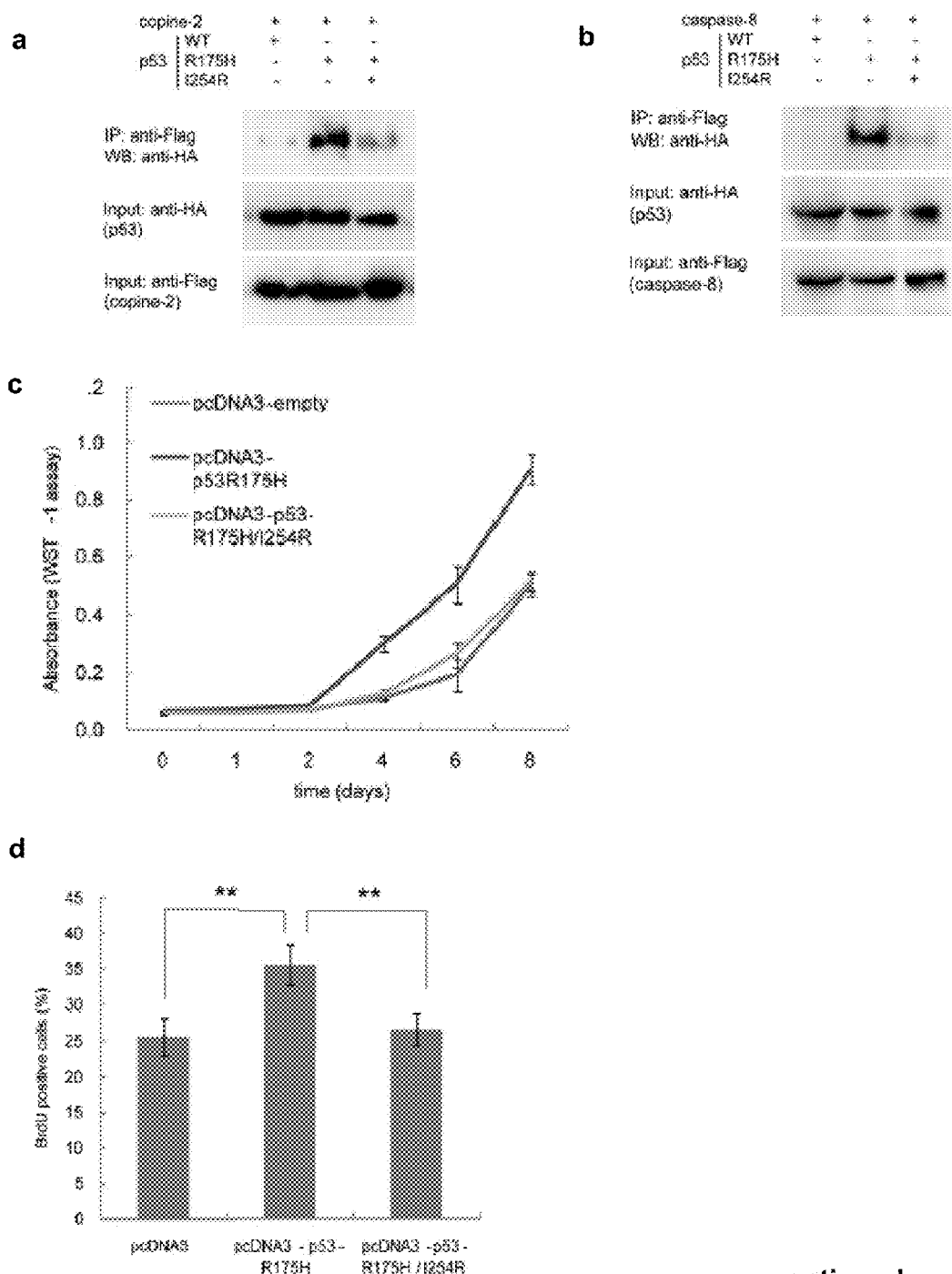
Figure 23:
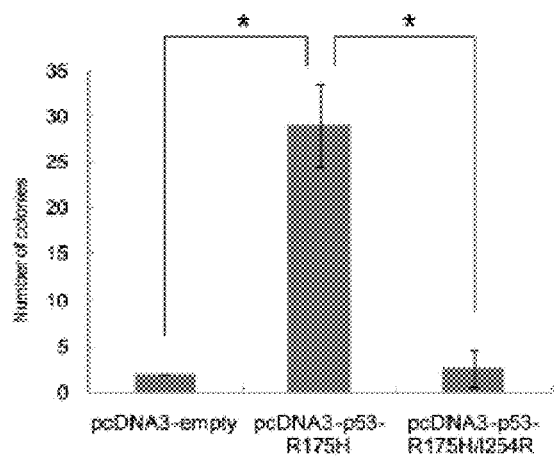

FIG. 23: Suppression of co-aggregation by a secondary charged mutation. Panel a: Co-immunoprecipitation (Co-IP) of copine-2 and p53 wild-type, R175H and R175H/I254R mutants in 4T1 cells. FLAG-tagged copine-2 was immunoprecipitated and p53-HA was detected by anti-HA (upper panel). The input controls of p53 and copine-2 are shown in the middle and lower panels. Panel b: Co-IP of caspase-8 and wild-type p53, R175H and R175H/I254R. The co-immunoprecipitated p53, input p53 and input caspase-8 are shown in upper, middle and lower panels, respectively. Panel c: WST-1 assay reveals the growth curve of 4T1 cells stably transfected with pcDNA3 vector, p53 R175H mutant and p53 R175H/I254R mutant. Panel d: Incorporation of BrdU in each stable cell line. The percentage of cells incorporated with BrdU are shown. Data represent mean values±s.d. (n=4). **P<0.01 (student t-test). Panel e: Soft agar colony formation assay of 4T1 stably transfected with the same set of plasmids. The number of colonies formed in each well are shown. Data represent mean values±s.d. (n=3). *P<0.05 (student t-test).

Figure 24:
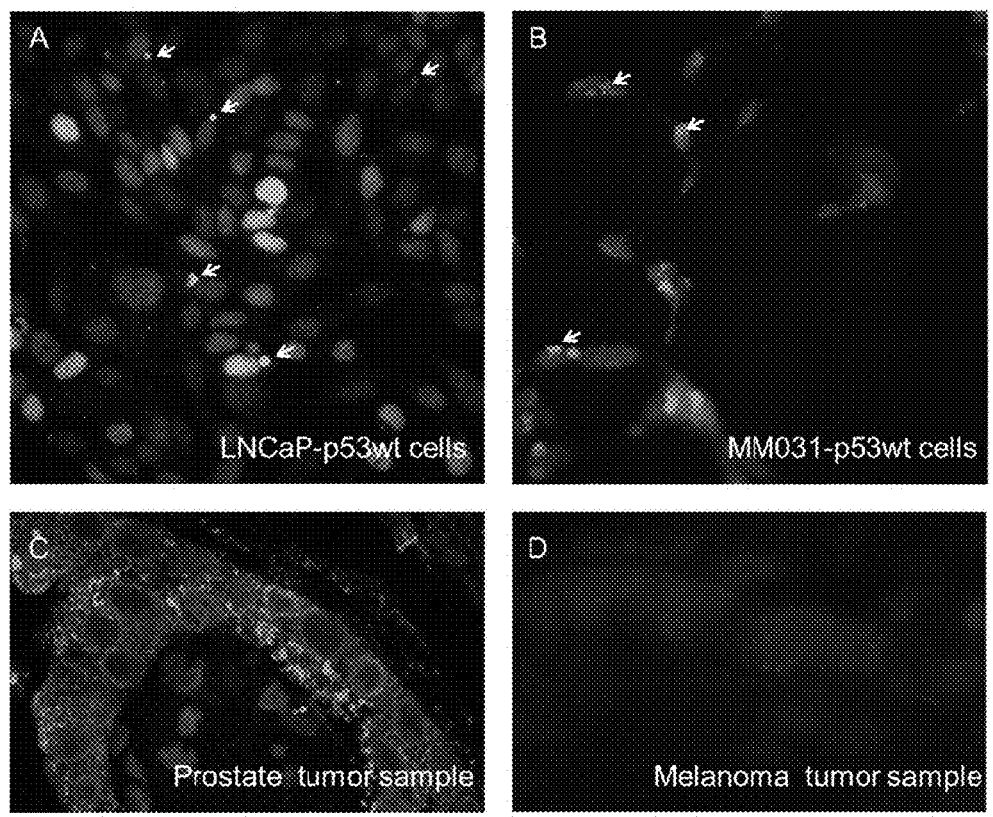

FIG. 24: By immuno-histochemical analysis of various clinical tumor samples, it was observed that, even in the absence of mutant p53, wt p53 could aggregate. When staining for p53 in the prostate cancer cell line LNCaP (panel A), and in a primary melanoma cell line MM031 (panel B), cytoplasmic inclusions of p53 (white arrows) were observed. A similar phenotype was observed in clinical samples of both prostate (panel C) and melanoma (panel D) tumors.

Figure 25:
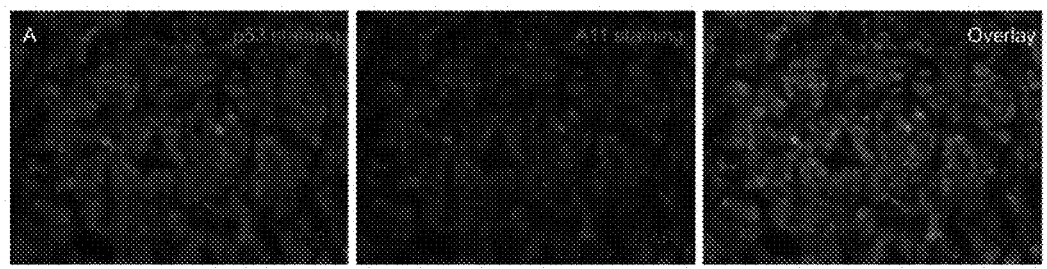

FIG. 25: Clinical sample showing cytoplasmic inclusions of p53, which was co-stained with the oligomer-specific antibody (A11). A nearly perfect co-localization could be observed between p53 and A11, showing that p53 is in an oligomeric state.

Figure 26:
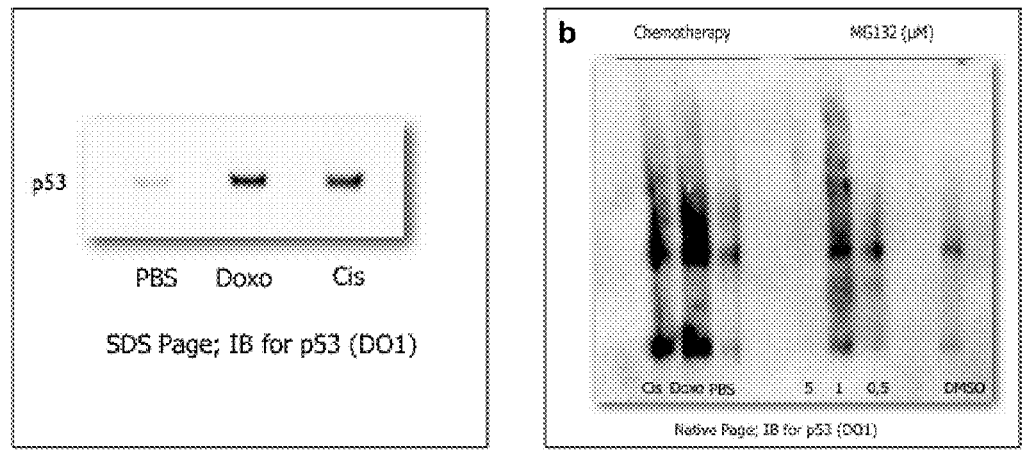

FIG. 26: Panel A: Western blot analysis of the U2OS cell line treated with the chemotherapeutic agents Doxorubicin or Cisplatin showing increased expression levels of p53. Panel b: Native page analysis showing high molecular-weight species of p53 upon treatment with cisplatin or doxorubicin, comparable to treatment with the proteasomal inhibitor MG132 at the indicated concentrations.

Figure 27:
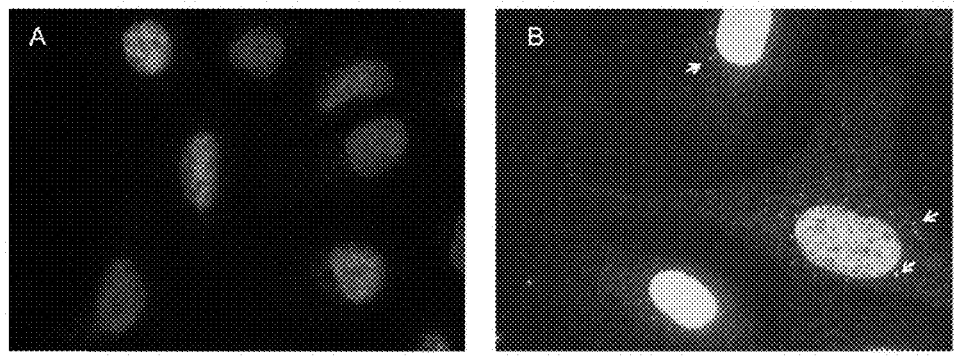
Figure 27:
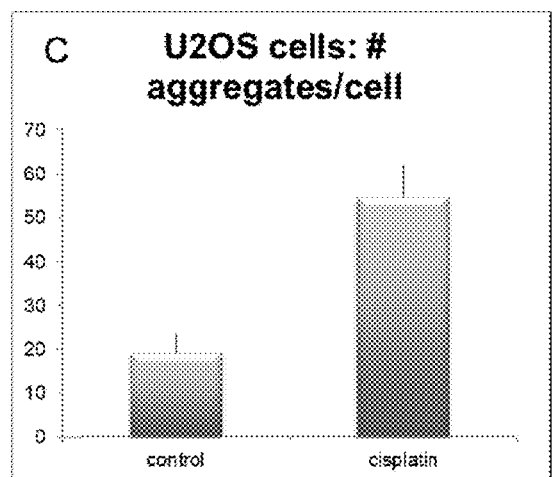

FIG. 27: When performing immunofluorescent staining for p53 in U2OS cells, it was subsequently observed, as compared to a control condition in baseline levels (panel A), an increased accumulation of non-soluble inclusions of p53 in the cytoplasm (white arrows) (panel B). The features of these inclusions were subsequently quantified using the InCell Analyzer 2000 (>1000 cells/condition), in which a greater than three-fold increase in cytoplasmic aggregates in U2OS cells was observed upon treatment with cisplatin (panel C).

Figure 28:
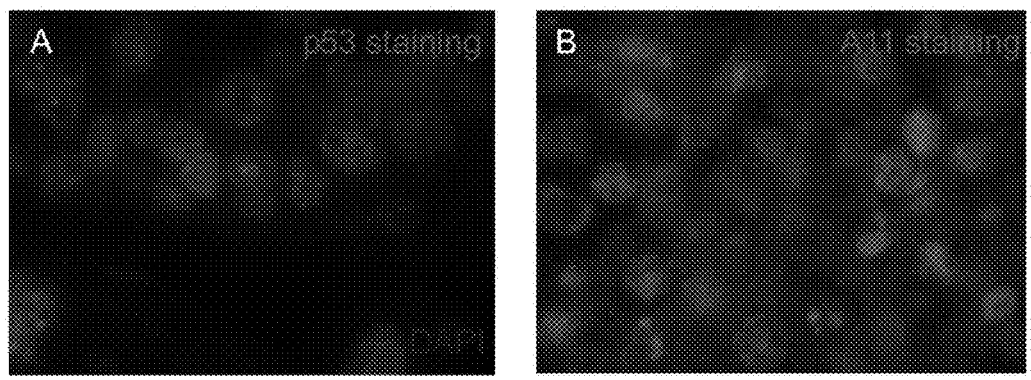

FIG. 28: When analyzing the status of p53 in histological samples of cisplatin-resistant ovarium tumor tissue, p53 could be observed in large aggreosomed-like inclusions (panel A). Importantly, these aggregates consisted of only WT p53 and not mutant p53. Strikingly, these inclusions were observed in the nucleus, and their oligomeric state was confirmed by A11 staining (panel B).

Figure 29:
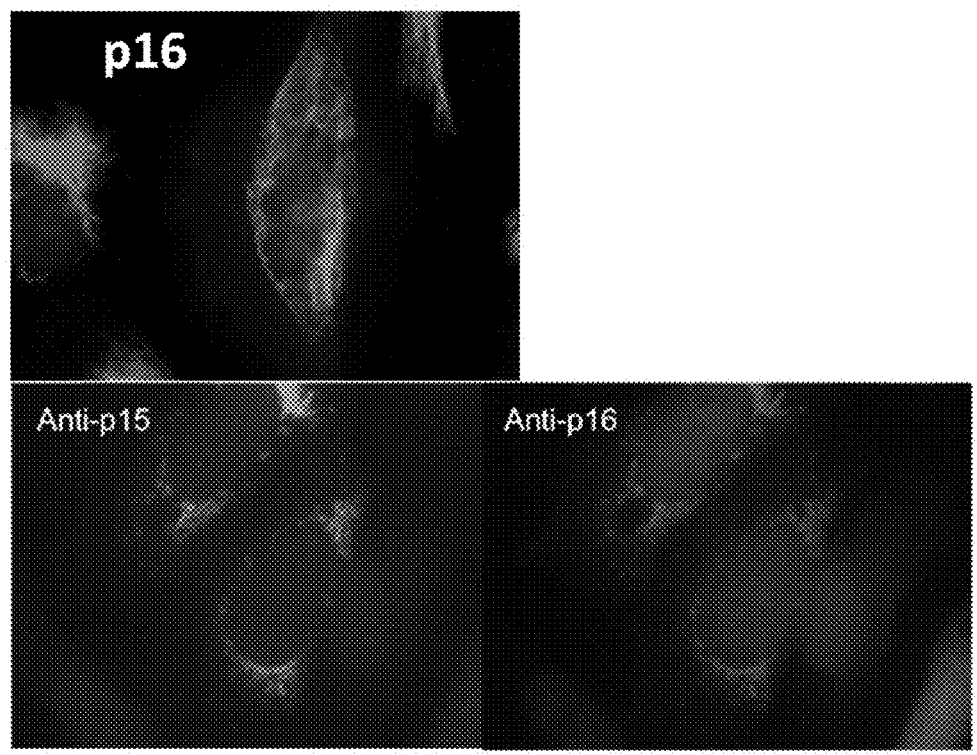

FIG. 29: Confocal image of cellular localization of p16 and p15 in HEK293 cells. DAPI stained (blue), p16 antibody (red) and vimentin (green).

Figure 30:
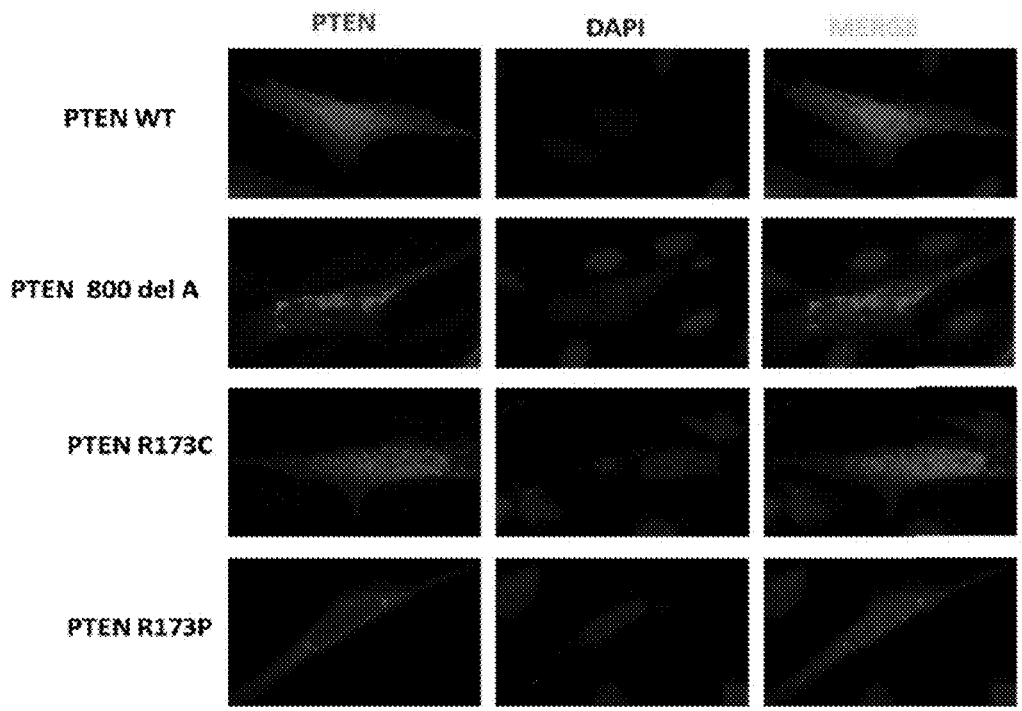

FIG. 30: Confocal image of cellular localization of PTEN wild-type, PTEN mutant 800 del A, PTEN mutant R173C, PTEN mutant R173P in HEK293 cells. DAPI stained (blue), anti-FLAG antibody (red).

Figure 31:
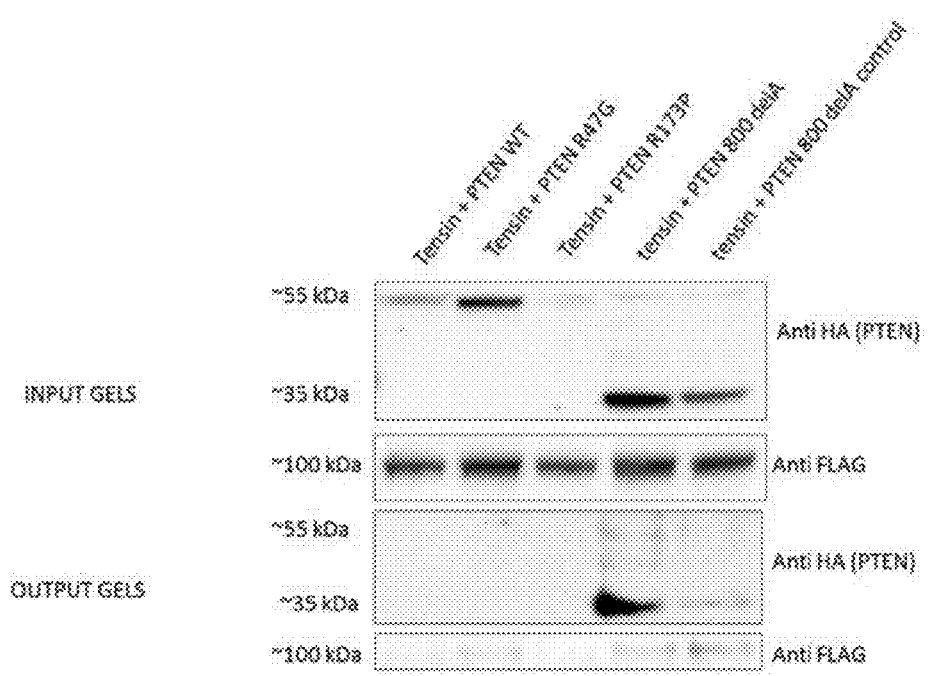

FIG. 31: Co-immunoprecipitation (Co-IP) of mutant PTEN and tensin.

DETAILED DESCRIPTION

Definitions

The disclosure will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated. Furthermore, the teens "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Unless otherwise defined herein, scientific and technical terms and phrases used in connection with the disclosure shall have the meanings that are commonly understood by those of ordinary skill in the art. Generally, nomenclatures used in connection herewith, and techniques of molecular and cellular biology, genetics and protein and nucleic acid chemistry and hybridization described herein are those well known and commonly used in the art. The methods and techniques of the disclosure are generally performed according to conventional methods well known in the art and as described in various general and more specific references that are cited and discussed throughout the present specification unless otherwise indicated. See, for example, Sambrook et al., *Molecular Cloning: A Laboratory Manual,* 2d ed., Cold Spring Harbor Laboratory Press, Cold Spring Harbor, N.Y. (1989); Ausubel et al., *Current Protocols in Molecular Biology,* Greene Publishing Associates (1992, and Supplements to 2002).

The term "coaggregation" or "aggregation," as used herein, refers to the formation of aggregates of proteins, and both terms are interchangeably used herein.

As used herein, the term "hydrophobic amino acids" refers to the following 13 amino acids: isoleucine (I), leucine (L), valine (V), phenylalanine (F), tyrosine (Y), tryptophan (W), histidine (H), methionine (M), threonine (T), lysine (K), alanine (A), cysteine (C), and glycine (G). The term "aliphatic amino acids" refers to I, L or V residues. The term "charged amino acids" refers to arginine (R), lysine (K)—both positively charged; and aspartic acid (D), glutamic acid (E)—both negatively charged. Although histidine is sometimes referred to as positively charged, since the nitrogen in its side chain can be protonated in acidic conditions, it is herein not envisaged under the charged amino acids, unless explicitly stated otherwise. Because the positive charge in physiological conditions is not comparable to that of R or K residues, it is the charge in physiological conditions that is important herein.

The phrase "a stretch of X contiguous amino acids," wherein X is a number, as used herein, refers to the fact that these X amino acids are present as an uninterrupted stretch, in the same order, in a protein of an organism (thus, naturally occurring). In other words, the stretch corresponds to the exact sequence of the protein over a length of X residues.

"Polypeptide," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally occurring amino acid polymers.

The term "identity," as used herein, is similar to "sequence identity" and refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, H is, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the disclosure, "sequence identity" will be understood to mean the "match percentage" calculated by the DNASIS computer program (Version 2.5 for WINDOWS®; available from Hitachi Software Engineering Co., Ltd., South San Francisco, Calif., USA) using standard defaults as used in the reference manual accompanying the software. "Similarity" refers to the percentage number of amino acids that are identical or constitute conservative substitutions. Similarity may be determined using sequence comparison programs such as GAP (Deveraux et al. 1984, *Nucleic Acids Research* 12:387-395). In this way, sequences of a similar or substantially different length to those cited herein might be compared by insertion of gaps into the alignment, such gaps being determined, for example, by the comparison algorithm used by GAP.

In a first aspect, the disclosure relates to a method of screening for a compound that inhibits or disrupts co-aggregation of one or more member proteins of a tumor-associated protein aggregome, wherein the method comprises the following steps:
 a. Providing a cell expressing both an aggregation-prone engineered member protein and one or more wild-type member proteins of the protein aggregome; or
 b. Alternatively, providing a cell expressing one or more wild-type member proteins of the protein aggregome in the presence of a chemical agent, such as a chemotherapeutic agent;
 c. Contacting the cell with a candidate compound; and
 d. Measuring the amount of co-aggregation of one or more member proteins of the protein aggregome and/or the activity of one or more wild-type member proteins of the protein aggregome;
wherein the co-aggregation is mediated by the exposure of a beta-aggregating region that is present in the member proteins, the beta-aggregating region comprising an amino acid sequence as follows:
 a stretch of 4 to 16 contiguous amino acids, at least 50% of which are hydrophobic amino acids, and in which at least one aliphatic residue or F is present, and if only one aliphatic residue or F is present, at least one, and preferably at least two, other residues are selected from Y, W, A, M and T; and in which no more than 1, and preferably no P, R, K, D or E residue is present.

In a specific embodiment, the method as described above further comprises the step of:
 e. Comparing the measured coaggregation or activity in step d in the presence or absence of the candidate compound,
 wherein the candidate compound is identified as a compound that inhibits or disrupts the coaggregation when a reduced/loss of coaggregation and/or a higher activity is measured in the presence of the compound as compared to in the absence of the candidate compound.

The term "beta-aggregating region," as used herein, refers to beta-aggregation inducing regions naturally occurring in proteins that can be found by using computer algorithms, such as TANGO, and will be further illustrated hereafter. Synonyms include beta-aggregation-inducing region or aggregation-nucleating region ("segment" is an equivalent term for "region") or self-association region.

Protein aggregation is known as an unwanted, disease-causing phenomenon. Aggregation refers to the fact that a protein that is normally soluble is changed into an insoluble protein or an aggregated protein in its normal biological environment. It is widely accepted that cross-beta-mediated aggregation is the most frequently occurring and biologically relevant mechanism of aggregation.[78] "Cross-beta aggregation" (or simply "beta-aggregation") is the term used to indicate that aggregation is nucleated via the formation of intermolecular beta sheets to which each molecule in the aggregate contributes an identical strand typically comprising at least four contiguous amino acids. It is well-established now that individual strands interact to form an intermolecular beta sheet and that this structure forms the backbone of the aggregate.[79, 80] "Beta-aggregating regions" in target proteins can be determined by computer programs, such as TANGO, which were developed for predicting the aggregation propensity of peptides and proteins.

The Tango algorithm has been described in more detail elsewhere[17] (especially the Methods section on pages 1305 and 1306 are herein specifically incorporated by reference; see also the Supplementary Notes 1 and 2 of the same article for further details on the methods and the data sets used for the calibration and the testing of the TANGO algorithm; more background can also be found in WO2007/071789). Briefly, to predict beta-aggregating regions of a protein or peptide, TANGO simply calculates the partition function of the phase-space. To estimate the aggregation tendency of a particular amino acid sequence, the following assumptions are made: (i) In an ordered beta-sheet aggregate, the main secondary structure is the beta-strand. (ii) The regions involved in the aggregation process are fully buried, thus paying full solvation costs and gains, full entropy and optimizing their H-bond potential (that is, the number of H-bonds made in the aggregate is related to the number of donor groups that are compensated by acceptors; an excess of donors or acceptors remains unsatisfied). (iii) Complementary charges in the selected window establish favorable electrostatic interactions, and overall net charge of the peptide inside but also outside the window disfavors aggregation. TANGO can be accessed on the World Wide Web. A high Tango score of a sequence stretch typically corresponds to a sequence with high (and kinetically favorable) beta-aggregation propensity. The zyggregator algorithm is another example.[74] These algorithms identify aggregation-prone sequences by comparing the aggregation propensity score of a given amino acid sequence with an average propensity calculated from a set of sequences of similar length.

Cross-beta aggregation of an amino acid region in a polypeptide or protein can be initiated when (1) it has a high hydrophobicity, (2) it has a good beta-sheet propensity, (3) it has a low net charge and (4) it is solvent-exposed. Thus, beta-aggregating protein regions are most often buried in the folded state and are not exposed to the solvent. The latter is confirmed by the experimental finding that in many globular proteins, aggregation occurs during refolding or under conditions in which denatured or partially folded states are significantly populated, i.e., at high concentration or as a result of destabilizing conditions or mutations (as detailed further herein).

A beta-aggregating region typically comprises an amino acid sequence of the following formula: a stretch of 4 to 16 contiguous amino acids, at least 50% of which are hydrophobic amino acids, and in which at least one aliphatic residue or F is present, and if only one aliphatic residue or F is present, at least one, and preferably at least two, other residues are selected from Y, W, A, M and T; and in which no more than 1, and preferably no P, R, K, D or E residue is present.

According to the above requirement, at least 50% of the amino acids in the stretch are hydrophobic amino acids, i.e., are amino acids selected from I, L, V, F, Y, W, H, M, T, K, A, C, and G. Further, a beta-aggregating region may also encompass a stretch of 4 to 16 contiguous amino acids, wherein at least 60% of the amino acids are hydrophobic amino acids, or at least ⅔ of the amino acids are hydrophobic amino acids, or at least 70% are hydrophobic amino acids, or at least 75% are hydrophobic amino acids, or at least 80% are hydrophobic amino acids, or at least 85% are hydrophobic amino acids, or at least 90% are hydrophobic amino acids, or at least 95% are hydrophobic amino acids, or even all amino acids are hydrophobic amino acids. Alternatively, it can be that at least three amino acids in the stretch are hydrophobic amino acids, particularly, at least four are hydrophobic amino acids, more particularly, at least five are hydrophobic amino acids, at least six or even more than six are hydrophobic amino acids.

According to the above requirement, at least one residue selected from I, L, V and F (aliphatic residue or F) is present, most particularly, more than one such residue is present. If only one of the residues of the stretch is an I, L, V or F residue, at least one residue in the stretch is selected from Y, W, M, T or A. More particularly, in these embodiments, at least two residues are selected from Y, W, M, T or A. According to very specific embodiments, at least two residues in the stretch are selected from I, L, V, F, Y, and W (i.e., from aliphatic or non-charged aromatic residues). According to other specific embodiments, at least three residues in the stretch are selected from I, L, V, F, Y, W, M, T, and A. According to further specific embodiments, at least four residues in the stretch are selected from I, L, V, F, Y, W, M, T, and A.

It should be noted that two residues selected from R, K, D and E may be present, as long as the net charge is zero (i.e., if their charges are opposite).

According to the above requirement, a beta-aggregating region typically comprises a stretch of 4 to 16 contiguous amino acids, more specifically, of 4 to 15 amino acids, of 4 to 14 amino acids, of 4 to 13 amino acids, of 4 to 12 amino acids, of 4 to 11 amino acids, of 4 to 10 amino acids, of 4 to 9 amino acids, or of 4 to 8 amino acids. It may also be that the length of the stretch is at least 5 amino acids. Accordingly, a beta-aggregating region may also comprise a stretch of 5 to 13 amino acids, particularly of 5 to 12 amino acids, of 5 to 11 amino acids, of 5 to 10 amino acids, of 5 to 9 amino acids, or of 5 to 8 amino acids. It may also be that the length of the stretch is at least six amino acids. Accordingly, a beta-aggregating region may also comprise a stretch of 6 to 13 amino acids, particularly of 6 to 12 amino acids, of 6 to 11 amino acids, of 6 to 10 amino acids, of 6 to 9 amino acids, or of 6 to 8 amino acids. It often occurs that beta-aggregating regions are stretches of six or seven amino acids.

Evidence is provided in the disclosure that the peptide sequence of a beta-aggregating region naturally occurring in a protein is the mediating factor for the protein to form an interactome of aggregation-specific interactions or aggregome, under conditions that the peptide comprised in the protein is exposed to the environment (i.e., a protein rendered aggregation prone through mutation, through fusion to another protein, through the presence of chemical agent, etc.). Thus, by "protein aggregome" is meant an aggregation-specific interactome of a protein, i.e., a set of proteins that form aggregation-specific interactions (referred to as "member proteins") engaged by an unfolded or misfolded protein wherein the beta-aggregating region is exposed to the environment, and wherein the interactions are not formed when the unfolded or misfolded member protein adapts its native conformation. In analogy therewith, by "member protein" or "family member" is meant a protein that forms part of a particular protein aggregation interactome or aggregome. Member proteins typically share an identical, or closely related, beta-aggregation peptide sequence. Notably, except for the beta-aggregating sequence, member proteins can be (but do not have to be) unrelated (i.e., low overall % sequence identity).

According to preferred embodiments, the above-described method of screening for compounds is meant to target co-aggregation of member proteins that form part of a tumor-associated protein aggregome. In that regard, the term "tumor-associated protein aggregome" refers to a particular protein aggregome (as defined hereinbefore) wherein aggregation-specific interactions of member proteins contribute to oncogenic gain-of-function by inactivation of multiple proteins in antiproliferative and apoptotic pathways. In other words, inactivation of member proteins of a tumor-associated protein aggregome is pro-proliferative and anti-apoptotic in a cellular context. Typically, a tumor-associated protein aggregome harbors a tumor-suppressor protein as a member protein.

The term "tumor-suppressor protein" is well known by the skilled artisan and refers to its function in preventing the development of cancer. Tumor-suppressor genes express proteins that help prevent or "suppress" abnormal cells from developing into full-blown tumors. When such genes are disabled, as they frequently are in cancer cells, cells can grow uncontrollably, forming tumors that are the hallmarks of cancer. Examples of tumor-suppressor genes include, without the purpose of being limitative, p53 (UNIPROT identifier P53_HUMAN, accession number P04637), p16 (UNIPROT identifier CD2A1_HUMAN, accession number P42771), pRb (UNIPROT identifier RB_HUMAN, accession number P06400), APC (UNIPROT identifier APC_HUMAN, accession number P25054), PTEN (UNIPROT identifier PTEN_HUMAN, accession number P60484), ATM (UNIPROT identifier ATM_HUMAN, accession number Q13315).

As used herein, "p53" refers to the tumor-suppressor protein p53 involved in the regulation of cell proliferation and is also well known in the art. The transcription factor p53 integrates numerous signals controlling cell life and death. Upon oncogenic or other stresses, p53 gets activated, which results in cell cycle arrest, cellular senescence, DNA repair or apoptosis. Active p53 (FIG. 1) is built up by four identical subunits of 393 residues that form two interacting dimers generating a tetramer. The structure of each subunit can be divided into five domains associated with different functions: the N-terminal transactivation domain (TAD), followed by a proline-rich region (PRR), next, the central DNA-binding core domain (p53C), then the tetramerization domain (TET) that includes a nuclear export signal, and finally, the C-terminus (CT) that comprises three nuclear localization signals. The central core domain of p53, that embodies roughly half of p53, accounts for more than 80% of the mutant p53 forms, mostly due to a single missense mutation. These p53C mutations can be subdivided in two classes: the "contact mutants" and "structural mutants." The contact mutants contain a mutation that directly affects DNA binding, due to the mutation and concomitant loss of an essential DNA-contacting residue, such as R273H and R248W. The structural mutants contain a mutation that distorts and destabilizes the structure of p53, which can even result in global unfolding of the protein. The p53C domain is intrinsically thermodynamically unstable and dictates the overall stability of the tetrameric p53 protein complex. In addition, the majority of hot-spot disease mutants such as R175H, R282W, R248Q, R249S and R110P further destabilize the protein.

As used herein, "PTEN" refers to the tumor-suppressor protein PTEN and is well known in the art. The PTEN protein modifies other proteins and fats (lipids) by removing phosphate groups, which consist of three oxygen atoms and one phosphorus atom. Based on this activity, the PTEN protein is a type of enzyme called a phosphatase. Accordingly, the PTEN gene belongs to the family of genes called PTP (protein tyrosine phosphatases). The PTEN gene may be the most frequently mutated gene in prostate cancer and in cancer of the uterine lining (endometrial cancer). PTEN mutations also have been identified in several other types of cancer, including certain aggressive brain tumors (glioblastomas and astrocytomas) and an aggressive form of skin cancer called melanoma. Mutations in the PTEN gene result in an altered enzyme that has lost its tumor-suppressor function. The loss of this enzyme likely permits certain cells to divide uncontrollably, contributing to the growth of cancerous tumors. In some cases, the presence of PTEN mutations (such as del 800) is associated with more advanced stages of tumor growth.

As used herein, "p16" refers to the tumor-suppressor protein cycline-dependent kinase A2 inhibitor (also named p16) and acts as a negative regulator of the proliferation of normal cells by interacting strongly with CDK4 and CDK6. This inhibits their ability to interact with cyclins D and to phosphorylate the retinoblastoma protein pRb. Mutation, promoter hypermethylation and loss of heterozygosity involving the tumor-suppressor gene p16 have been detected in a wide variety of human cancers. Examples of p16 mutations include, without the purpose of being limitative, G101W, R24P, S56I and L65P.

As used herein, "pRb" refers to the tumor-suppressor retinoblastoma protein pRb and is well known in the art. It is dysfunctional in many cancer types. pRb belongs to the pocket protein family, whose members have a pocket for the functional binding of other proteins.

Also encompassed are homologs, including orthologs and paralogs, of the tumor-suppressor proteins of the disclosure. As used herein, the term "homolog" means a gene related to a second gene by descent from a common ancestral DNA sequence. The term "homolog" may apply to the relationship between genes separated by speciation (e.g., ortholog), or to the relationship between genes originating via genetic duplication (e.g., paralog). As used herein, the term "ortholog" refers to genes in different species that have evolved from a common ancestral gene via speciation. Orthologs often (but certainly not always) retain the same function(s) during the course of evolution. Thus, functions may be lost or gained when comparing a pair of orthologs. As used herein, the term "paralogs" refers to genes produced via gene duplication within a genome. Paralogs typically evolve new functions or else eventually become pseudogenes.

Examples of homologs of p53 include the paralogs p63 (UNIPROT identifier P63_HUMAN, accession number Q9H3D4) and p73 (UNIPROT identifier P73_HUMAN, accession number O15350). As used herein, "p63" and "p73" are members of the p53 gene family (63% identity of p53 with p73, and 60% of p53 with p63), and their transactivation isoforms have partial functional overlap with p53. Although p63 and p73 are rarely mutated in tumors, their functions are frequently inhibited by mutant p53, leading to an increase in oncogenic potential of the affected cells.[13, 24] Examples of homologs of p16 include p15 (UNIPROT identifier CDN2B_HUMAN, accession number P42772). Examples of homologs of PTEN include Tensin-3 (UNIPROT identifier TENS3_HUMAN, accession number Q68CZ2).

Notably, the occurrence of tumor-associated protein aggregomes in a cell is indicative for a disease, in particular, cancer. Non-limiting examples of tumor-associated protein aggregomes are provided hereafter and is also further illustrated in the Example section. As confirmed by analyzing clinical samples from patients suffering from cancer, it is often the unfolding or misfolding of a tumor-suppressor protein (e.g., through mutation of the protein, or through the use of chemotherapeutic agents, or through general proteostatic collapse) that initiates the process of forming aggregomes. Thus, according to a specific embodiment, the tumor-associated protein aggregome as referred to in the above-described screening method is a tumor-suppressor protein aggregome. To illustrate this further, a tumor-suppressor aggregome may be chosen from the group comprising a p53 aggregome, a PTEN aggregome, a p16 aggregome and a pRb aggregome. According to more specific embodiments, member proteins of a p53 aggregome may be chosen from the group comprising p53 (UNIPROT identifier P53_HUMAN, accession number P04637), p63 (UNIPROT identifier P63_HUMAN, accession number Q9H3D4), p73 (UNIPROT identifier P73_HUMAN, accession number O15350), copine-2 (UNIPROT identifier CPNE2_HUMAN, accession number Q96FN4), caspase-8 (UNIPROT identifier CASP8_HUMAN, accession number Q14790); member proteins of a first PTEN aggregome may be chosen from the group comprising PTEN (UNIPROT identifier PTEN_HUMAN, accession number P60484), tensin-3 (UNIPROT identifier TENS3_HUMAN, accession number Q68CZ2); member proteins of a second PTEN aggregome may be chosen from the group comprising PTEN (UNIPROT identifier PTEN_HUMAN, accession number P60484), oxidative stress-induced growth inhibitor 1 (UNIPROT identifier OSGI1_HUMAN, accession number Q9UJX0); member proteins of a p16 aggregome may be chosen from the group comprising p16 (UNIPROT identifier CD2A1_HUMAN, accession number P42771), p15 (UNIPROT identifier CDN2B_HUMAN, accession number P42772).

In particular embodiments, the amino acid sequence of a member protein of a p53 aggregome comprises the stretch ILTIITL (SEQ ID NO:2), which is identical to the naturally occurring beta-aggregating region in the p53 tumor-suppressor protein, or may comprise a non-identical but closely related stretch of amino acids (for example, see Table 1). In other particular embodiments, the amino acid sequence of a member protein of a first PTEN aggregome comprises the stretch YLVLTLT (SEQ ID NO:62), which is identical to a naturally occurring beta-aggregating region in the PTEN tumor-suppressor protein, or may comprise a non-identical but closely related stretch of amino acids (for example, YLVLNLS (SEQ ID NO:63) in Tensin-3). In still other particular embodiments, the amino acid sequence of a member protein of a second PTEN aggregome comprises the stretch VALLF (SEQ ID NO:60), which is identical to a naturally occurring beta-aggregating region in the PTEN tumor-suppressor protein (for example, oxidative stress-induced growth inhibitor 1 (Osgin1)), or may comprise a non-identical but closely related stretch of amino acids. In still other particular embodiments, the amino acid sequence of a member protein of a p16 aggregome comprises the stretch TLVVLH (SEQ ID NO:84), which is identical to a naturally occurring beta-aggregating region in the p16 tumor-suppressor protein (for example, p15), or may comprise a non-identical but closely related stretch of amino acids. Typically, one or two substitutions may occur in such a stretch of amino acids. Substitutions can be either conservative or non-conservative. Conservative substitution is the substitution of amino acids with other amino acids whose side chains have similar biochemical properties (e.g., are aliphatic, are aromatic, are positively charged, etc.) and is well known to the skilled person. Non-conservative substitution is then the substitution of amino acids with other amino acids whose side chains do not have similar biochemical properties (e.g., replacement of a hydrophobic with a polar residue). Conservative substitutions will typically yield sequences that are not identical anymore, but still highly similar.

According to preferred embodiments of the above-described screening method, the aggregation-prone engineered member protein is a mutated member protein, for example, a mutated tumor-suppressor protein such as a mutated p53 carrying a mutation chosen from the group comprising R110P, R110L, R175H, Y220C, G245S, R248Q R249S, P250L, E258V, R282W, or a mutated p16 carrying a mutation such as S56I, or a mutated PTEN carrying a mutation PTEN 800 del A, R173C, R173P. In the alternative, the aggregation-prone engineered member protein is a fusion protein of a wild-type member protein fused to a protein, preferably a detectable protein, such as a fluorescent protein (e.g., green fluorescent proteins, and derivatives thereof, red fluorescent proteins, and derivatives thereof, etc.; which are all well known in the art).

The term "aggregation-prone engineered member protein," as used herein, means the protein that is encoded by the engineered member protein and is prone to aggregate in vivo or in vitro. Within the context of the disclosure, "engineered" refers to a protein that is not the wild-type protein. In particular, it refers to a modified protein, for example, modified by mutation or by fusion to another protein. The types of mutation include substitution, insertion or deletion of nuclear acid residue(s) that cause the substitution, insertion, deletion or frameshift of encoded protein sequence. Similarly, the term "aggregation-prone mutated tumor-suppressor protein," as used herein, means the protein that is encoded by the mutated tumor suppressor and is prone to aggregate in vivo or in vitro.

Within the context of the disclosure, the term "coaggregation" or "aggregation" includes the aggregation of aggregation-prone engineered member proteins as well as the coaggregation with other member proteins, in particular, antiproliferative proteins and/or pro-apoptotic proteins. Notably, coaggregation is not only confined to the sequestration of wild-type member proteins by an aggregation-prone engineered version of the wild-type member protein (i.e., homo-aggregates, for example, homo-aggregates of mutant p53 and wild-type p53), but also encompasses the formation of hetero-aggregates between homologs of the wild-type member protein and an aggregation-prone engineered version of the wild-type member protein (for example, hetero-aggregates of mutant p53 and wild-type p63/p73) as well as between unrelated member proteins (except for an identical or closely related beta-aggregating sequence) and an aggregation-prone engineered version of the wild-type member protein. In particular embodiments, "coaggregation" is meant to include the formation of aggregates of wild-type member proteins or non-aggregating mutants of member proteins (for example, p53 contact mutants) or combinations thereof. This type of coaggregation will particularly occur in the presence of a chemical agent, such as a chemotherapeutic agent (as described further herein).

Thus provided is a cell-based assay to screen for compounds that inhibit or disrupt co-aggregation of one or more member proteins of a tumor-associated protein aggregome. Preferably, assays are performed in prokaryotic cells, eukaryotic cells, advantageously in mammalian cells, such as human cells, or yeast cells, such as *Saccharomyces cerevisae*. Preferably, cultured cell lines are used, for example, mammalian cell lines, preferably human cell lines.

The terms "inhibits," "inhibiting" or "inhibition," as used herein, mean blocking of (co)aggregation and includes preventing the accumulation of aggregation-prone misfolded proteins. The terms "disrupts," "disrupting" or "disruption" refer to the solubilization and/or degradation of aggregated proteins. Both terms encompass causing a net decrease of protein aggregation by either direct or indirect means.

The term "compound" or "candidate compound" is used herein in the context of a "test compound" or a "drug candidate compound" described in connection with the methods of the disclosure. As such, these compounds comprise organic or inorganic compounds, derived synthetically or from natural resources. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies, antibody fragments or antibody conjugates. For high-throughput purposes, compound libraries may be used. Examples include, but are not limited to, natural compound libraries, allosteric compound libraries, peptide libraries, antibody fragment libraries, synthetic compound libraries, etc. The term "agent," as used herein, refers to an antisense polynucleotide, or a ribozyme, or a small interfering RNA (siRNA).

The read-out for the identification of compounds that impair the aggregative behavior and/or the confirmation of positive hits can be done in a number of ways. Preferably, initial screens are performed in cells, for example, yeast cells, or in cultured cell lines, for example, mammalian cell lines, preferably human cell lines. Further validation of the therapeutic potential of promising compounds is preferably done in animal models, for example, murine models.

Reactivation of wild-type member proteins (for example, tumor-suppressor proteins, homologs thereof, or unrelated proteins containing an identical or closely related beta-aggregating region as for the tumor-suppressor protein), and thus counteracting the dominant-negative effect and gain-of-function activity of structural destabilized member proteins (for example, structural destabilized tumor-suppressor proteins) can be done by measuring the activity of the wild-type member protein and comparing the measured activity in the presence or absence of candidate compounds. The phrase "measuring the activity," as used herein, refers to measuring the activity both at the nucleic acid and/or protein level. For example, this can be done by performing qPCR of target genes of a particular wild-type member protein, or by making use of a reporter plasmid construct containing a reporter gene under the control of member protein-responsive elements so that the read-out is shut off under aggregating conditions and turned on once the aggregation between wild-type and structurally destabilized member protein is abolished. Otherwise, any biochemical assay that reports on wild-type function or any direct functional assay such as a cell proliferation assay can be useful ways of identifying aggregation-breaking compounds. Alternatively, one can also directly determine the level of aggregation in the presence or absence of candidate compounds. The phrase "measuring the amount of coaggregation," as used herein, refers to measuring the degree or level of coaggregation and can be done by comparing (fractionated) cell lysates on native PAGE and SDS-PAGE, followed by Western blotting, by using the PROTEOSTAT® Aggresome Detection Kit (ENZO Lifesciences), by immunofluorescence staining, etc., in the presence or absence of candidate compounds. All of those are well-established techniques by the skilled person in the art and are also described in the Example section.

According to specific embodiments, the screening method as described above further comprises one or more of the following steps:
 a. measuring the degree of degradation of one or more wild-type member proteins and aggregation-prone engineered member protein of the protein aggregome; or
 b. measuring cell survival, or
 c. measuring sensitivity to chemotherapeutic agents.

Examples of assay methods for identifying compounds in the context of the disclosure are described in the Example section, without the purpose of being limitative. It should be clear to the skilled artisan that the present screening methods might be based on a combination or a series of measurements, particularly when establishing the link with aggregation. Also, it should be clear that there is no specific order in performing these measurements while practicing the disclosure.

Also disclosed is a method of identifying a compound that inhibits or disrupts the coaggregation of an aggregation-prone mutated tumor-suppressor protein with a wild-type tumor-suppressor protein and/or with a homolog of the wild-type tumor-suppressor protein, comprising the following steps:
 a. Providing a cell expressing both an aggregation-prone mutated tumor-suppressor protein and either of a wild-type tumor-suppressor protein or a homolog of the wild-type tumor-suppressor protein,
 b. Contacting the cell with a candidate compound,
 c. Measuring the amount of coaggregation, or alternatively measuring the activity of the wild-type tumor-suppressor protein, or alternatively measuring the activity of the homolog of the wild-type tumor-suppressor protein,
 d. Comparing the measured coaggregation or activity in step c in the presence or absence of the candidate compound, wherein the candidate compound is identified as a compound that inhibits or disrupts coaggregation when a reduced/loss of coaggregation and/or a higher activity is measured in the presence of the compound as compared to in the absence of the candidate compound.

Within the context of this embodiment, the term "coaggregation" or "aggregation" includes the aggregation of aggregation-prone mutated tumor proteins as well as the coaggregation with other tumor-suppressor proteins. Notably, coaggregation is not only confined to the sequestration of wild-type tumor-suppressor proteins by an aggregation-prone mutated version of the wild-type tumor-suppressor protein (i.e., homo-aggregates, for example, homo-aggregates of mutant p53 and wild-type p53), but also encompasses the formation of hetero-aggregates between homologs of the wild-type tumor-suppressor protein and an aggregation-prone mutated version of the wild-type suppressor protein (for example, heteroaggregates of mutant p53 and wild-type p63/p73). In particular embodiments, coaggregation is meant to include the formation of aggregates of wild-type tumor-suppressor proteins or non-aggregating mutants of tumor-suppressor proteins (for example, p53 contact mutants) or combinations thereof.

The term "aggregation-prone mutated tumor-suppressor protein" as used herein, means the protein that is encoded by the mutated tumor-suppressor and is prone to aggregate in vivo or in vitro. The types of mutation include substitution, insertion or deletion of nuclear acid residue(s) that cause the substitution, insertion, deletion or frameshift of encoded protein sequence.

In a second aspect, the invention also encompasses aggregation-disrupting agents or compounds identified by the screening method according to the invention, for use as a medicament and, in particular, as an antitumor agent to prevent and/or to treat cancer.

As used herein, the term "preventing cancer" means inhibiting or reversing the onset of the disease, inhibiting or reversing the initial signs of the disease, inhibiting the appearance of clinical symptoms of the disease. As used herein, "treating cancer" or "treating a subject or individual having cancer" includes substantially inhibiting the disease, substantially slowing or reversing the progression of the disease, substantially ameliorating clinical symptoms of the disease or substantially preventing the appearance of clinical symptoms of the disease. In particular, it includes inhibition of the replication of cancer cells, inhibition of the spread of cancer, reduction in tumor size, lessening or reducing the number of cancerous cells in the body, and/or amelioration or alleviation of the symptoms of cancer. A treatment is considered therapeutic if there is a decrease in mortality and/or morbidity, and may be performed prophylactically or therapeutically. A variety of subjects or individuals are treatable. Generally, such individuals are mammals or mammalian, where these terms are used broadly to describe organisms that are within the class mammalia, including the orders carnivore (e.g., dogs and cats), rodentia (e.g., mice, guinea pigs, and rats), and primates (e.g., humans, chimpanzees, and monkeys). In many embodiments, the individuals will be humans. A "patient" is a human subject in need of treatment.

As used herein, the term "cancer" refers to any neoplastic disorder, including such cellular disorders as, for example, renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer, mammary adenocarcinoma, pharyngeal squamous cell carcinoma, and gastrointestinal or stomach cancer.

In one embodiment, the compounds according to the disclosure are particularly useful for the prevention and/or treatment of cancer in a subpopulation of subjects having a structural destabilizing mutation in a tumor-suppressor protein, for example, a mutation in a p53 tumor-suppressor protein, such as a R175H, R282W, R248Q, R248W, R249S, R110P, or in a p16 tumor-suppressor protein, such as S56I, or in a PTEN tumor-suppressor protein, such as PTEN 800 del A, R173C, R173P. According to another specific embodiment, the compounds are particularly useful for the prevention and/or treatment of cancer in a subpopulation of subjects treated with or under treatment with chemotherapeutic agents. Chemotherapy is the treatment of cancer with an antineoplastic drug or with a combination of such drugs in a standardized treatment regimen. The majority of chemotherapeutic drugs can be divided in to alkylating agents, antimetabolites, anthracyclines, plant alkaloids, topoisomerase inhibitors, and other antitumor agents. All of these drugs affect cell division or DNA synthesis and function in some way. Examples of currently used chemotherapeutica include, without limitation, alkylating agents, such as cisplatin, carboplatin, oxaliplatin, mechlorethamine, cyclophosphamide, chlorambucil, ifosfamide; or plant-derived substances, such as vincristine, vinblastine, vinorelbine, vindesine, paclitaxel, docetaxel; or topoisomerase inhibitors, such as irinotecan, topotecan, amsacrine, etoposide, etoposide phosphate, teniposide; or cytotoxic antibiotics, such as doxorubicin, daunorubicin, valrubicin, idarubicin, epirubicin, bleomycin, plicamycin, mitomycin; or antimetabolites, such as fluorouracil.

According to other specific embodiments, the compounds are particularly useful for the prevention and/or treatment of cancer in a subpopulation of subjects suffering from a general reduction in proteostasis capacity or general proteostatic collapse. The term "proteostatic collapse," as used herein, refers to a general reduction in proteostasis capacity, for example, due to the loss of function of an important element of the protein quality control machinery, such as a chaperone or protein degradation mediator (proteasome, autophagosome, or ubiquitin ligases). This occurs in individuals through aging. It can also be induced by RNAi or chemical inhibitors (e.g., lactacystin, MG-132, pifithrin, geldanamycin), or by over-expression of another aggregating protein, leading to so-called proteostatic overloading.

The disclosure also relates to a pharmaceutical composition comprising a therapeutically effective quantity of a compound according to the disclosure, for use as a medicament and, in particular, as an antitumor agent to prevent and/or to treat cancer, together with at least one pharmaceutically acceptable carrier, diluent and/or excipient.

The term "medicament to prevent and/or treat" relates to a composition comprising molecules as described above and a pharmaceutically acceptable carrier or excipient (both terms can be used interchangeably) to prevent and/or to treat diseases as indicated above. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers.

By "effective quantiy" or "effective amount" in the context of treating or preventing a condition is meant the administration of that amount of a compound to an individual in need of such treatment, either in a single dose or as part of a series, which is effective for treatment or prophylaxis of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The medicament may be administered by any suitable method within the knowledge of the skilled man. The preferred route of administration is parenterally. In parental administration, the medicament of this invention will be formulated in a unit dosage injectable form such as a solution, suspension or emulsion, in association with the pharmaceutically acceptable excipients as defined above. However, the dosage and mode of administration will depend on the individual or subject. These medicaments can be intended for human or veterinary use.

In a specific embodiment it should be clear that the therapeutic method of the disclosure against cancer can also be used in combination with any other cancer therapy known in the art such as irradiation, chemotherapy or surgery.

In still another aspect, the disclosure also envisages a method of screening for a new member protein of a tumor-associated protein aggregome indicative for a disease, in particular, cancer, comprising the following steps:

a. Identifying in at least one protein at least one region of 4 to 16 contiguous amino acids, at least 50% of which are hydrophobic amino acids, and in which at least one aliphatic residue or F is present, and if only one aliphatic residue or F is present, at least one, and preferably at least two, other residues are selected from Y, W, A, M and T; and in which no more than 1, and preferably no P, R, K, D or E residue is present;

b. Contacting the protein identified in step a with an aggregation-prone engineered member protein of a tumor-associated protein aggregome;

c. Assessing the aggregation and/or function of the protein of step a.

According to a particular embodiment, the new member protein that is identified by using the above screening method is a new target for the treatment of cancer.

Contacting the protein identified in step a with an aggregation-prone engineered member protein of a tumor-associated protein aggregome (see definitions as described hereinbefore) may be entirely in vitro, e.g., with purified protein in a test tube or a plate. However, the methods can also be used in cellular systems. Function can, e.g., be assessed using suitable reporter read-outs (see also supra).

Preferably, the method of screening for new member proteins of tumor-associated protein aggregomes is performed in a cell-based assay. For example, the candidate member protein and a known aggregation-prone mutated member protein of a tumor-associated aggregome can be co-expressed in a cell. Subsequently, the aggregation can be evaluated by performing co-localization studies and/or co-immunoprecipitation studies, and/or BN-PAGE followed by Western analysis, which is all exemplified in the Example section. Additionally or alternatively, the function of the new member protein can be evaluated by making use of existing functional assays. Assessing the aggregation and/or function of a protein can be done by assessing protein activity, degradation of aggregates, sensitivity to chemical agents, cell survival, cell growth, cellular reproduction, cellular senescence.

Alternatively, an in vitro peptide binding assay can also be used as is described in Example 11.

Notably, it will be clear that the candidate new member protein will likely contain a beta-aggregating region that is identical to or closely related to known member proteins of a particular tumor-associated protein aggregome.

The disclosure might also be useful for diagnostic applications. Accordingly, in still another aspect, the invention also provides a method to stratify individuals suffering from cancer comprising the step of assessing the conformational status of a member protein of a tumor-associated protein aggregome, irrespective of the presence of a structural destabilizing mutation in the member protein.

The following examples are intended to promote a further understanding of the disclosure. While the disclosure is described herein with reference to illustrated embodiments, it should be understood that the invention is not limited hereto. Those having ordinary skill in the art and access to the teachings herein will recognize additional modifications and embodiments within the scope thereof. Therefore, the disclosure is limited only by the claims attached herein.

EXAMPLES

I. Identification and Characterization of a p53 Aggregrome and Agents Disrupting Co-Aggregation of Member Proteins of p53 Aggregome Example 1

Structurally Destabilized p53 Mutants Aggregate In Vitro

In order to investigate the effect of contact and structural mutations in p53 on their cellular distribution, wild-type and mutant p53 in the human osteosarcoma SaOS-2 cell line, which is devoid of endogenous p53, was first transiently over-expressed. Immunofluorescence revealed a predominant nuclear distribution of wild-type p53 and of the DNA-contact mutants R248W and R273H. In contrast, p53 mutants R175H, R282W, R249S, R248Q, P250L, E258V, R110L and R110P showed reduced nuclear staining, with a compensatory increase of cytoplasmic staining (data not shown; and FIG. 2, panel a), with the latter regularly containing "punctate" cytoplasmic spots. A punctate staining suggested the assembly of mutant p53 into large aggregates within the peri-nucleus, and was consistent with an impaired nuclear import of p53.[14]

Figure 2:
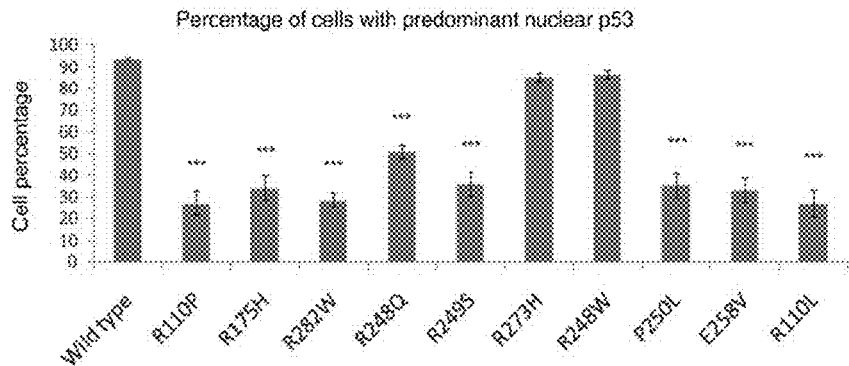
FIG. 2: The aggregation of mutant p53 over-expressed in SaOS-2 cells. Panel a: Statistics on the localization of p53 mutants over-expressed in SaOS-2 cells. Data represent mean values±s.d. (n=4). All mutants were compared to the wild-type. ***P<0.001 (student t-test). Panel b: Blue-Native PAGE of wild-type and mutant p53 expressed in SaOS-2 cells. Cell lysate was prepared under non-denaturing conditions, and electrophoresis was performed without SDS. The first lane shows molecular weight marker, and the rest of the gel indicates immunoblot of p53 using Do-1 antibody. Panel c: SDS-PAGE showed similar expression levels of mutant and wild-type p53. Actin was detected as loading control.
Figure 2:
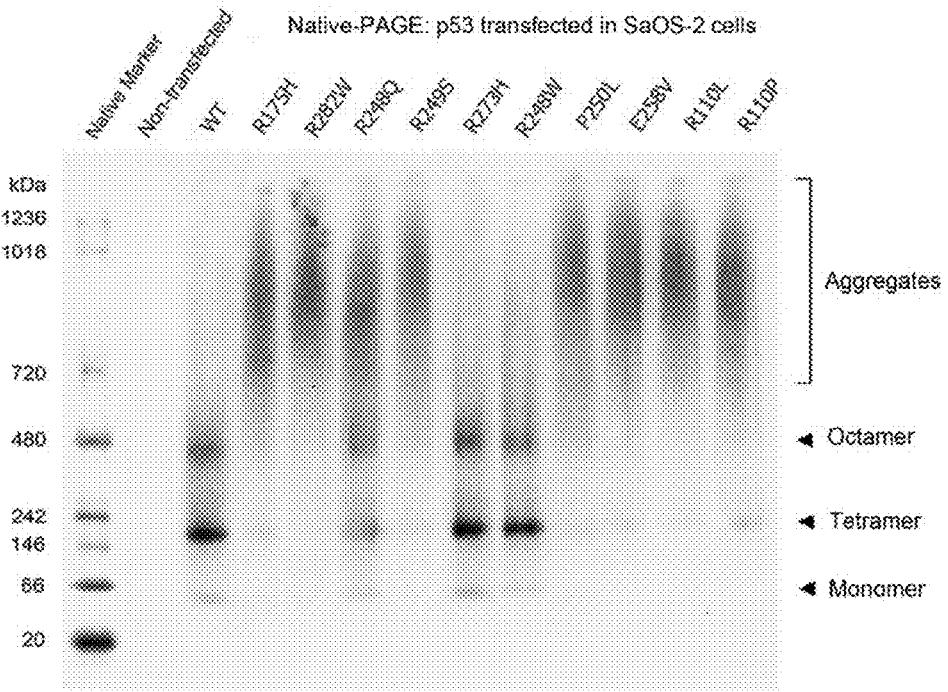
Figure 2:
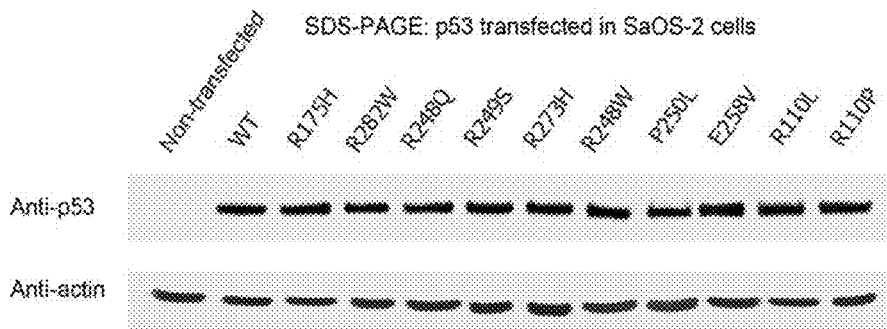

To further investigate the aggresomal nature of the observed inclusions, several strategies were adopted. (i) Since the formation of cytoplasmic inclusions in aggresomes is an active process that depends on cytoskeletal integrity,[15] transfected cells were treated with nocodazole, a small chemical that disrupts microtubule assembly. Indeed, following nocodazole treatment, the cellular distribution of mutant p53 shifted from a punctate to a diffuse cytoplasmic staining, thereby confirming the aggresomal nature of these inclusions (data not shown). (ii) The oligomerization state of p53 in SaOS-2 cells by Blue-Native PAGE (BN-PAGE) and Western blot analysis was also assessed, after cell lysis with a mild detergent (CHAPS). In agreement to previous reports,[16] transiently over-expressed wild-type p53 appeared as monomers, tetramers and octamers on Western blot and an identical pattern was also observed for the DNA-contact mutants R248W and R273H (FIG. 2, panel b). However, over-expression of the aggregating mutants R175H, R282W, R248Q, R249S, P250L, E258V, R110L and R110P caused a shift in molecular mass ranging from 800 kDa up to the fractionation limit of the gel (10,000 kDa), consistent with the formation of large multimeric assemblies (FIG. 2, panel b). In denaturing but non-reducing PAGE, the oligomers and aggregates were dissociated into monomers, and all mutants were expressed at similar levels (FIG. 2, panel c).

Example 2

Analysis of the Aggregation Propensity of p53

Figure 1:
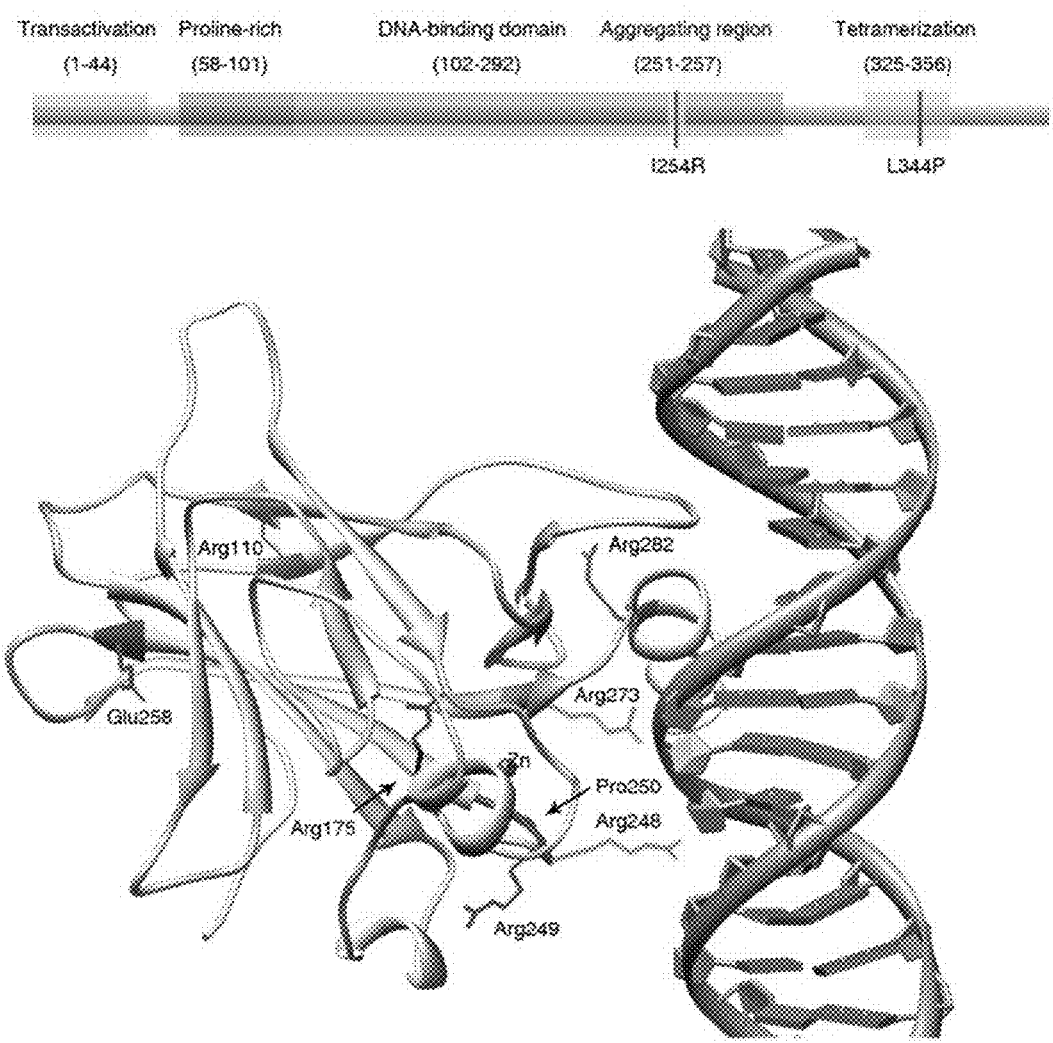
FIG. 1: Structure of p53 protein and the effects of mutations on protein cellular localization. The schematic domain structure of p53 is shown in the upper panel. An aggregation-prone sequence sits in the DNA-binding domain, spanning the residues 251 to 257. Mutations that can inhibit aggregation (I254R) or abolish tetramerization (L344P) are labeled in red. The structure of p53 DNA-binding domain is shown in the lower panel. The structural mutations (R110P, R175H, R248Q, R249S and R282W) and the contact mutations (R248W and R273H) are, respectively, labeled in red and green. The aggregation-prone sequence is shown in yellow. (Protein Data Bank code 1TUP, image generated by VMD software).
Figure 3:
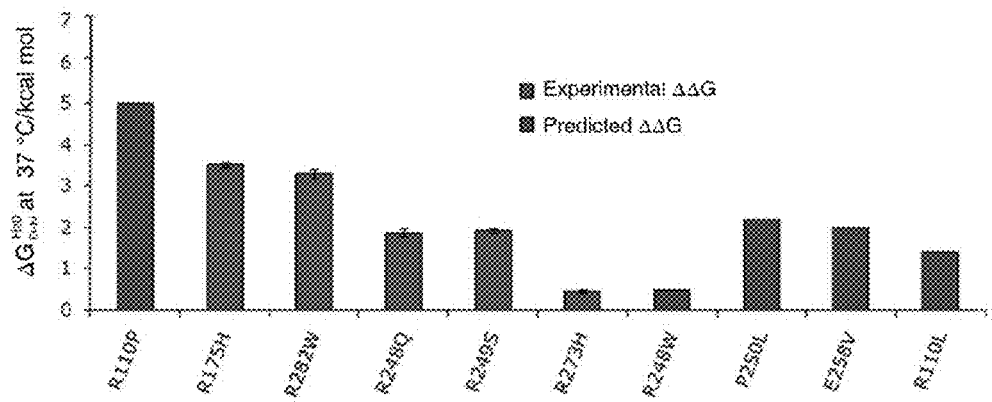
FIG. 3: Structural stability and aggregation-prone sequence of p53 mutants. Panel a: Experimental DDG values were taken from previously published data.[48] For mutations where no experimental data was available, DDG values were calculated using the molecular force field FoldX.[49] Panel b: TANGO prediction for the aggregation propensity of wild-type p53. The sequence segment ILTIITL (amino acids 251-257) showed a high tendency to form β-sheet aggregation.
Figure 3:
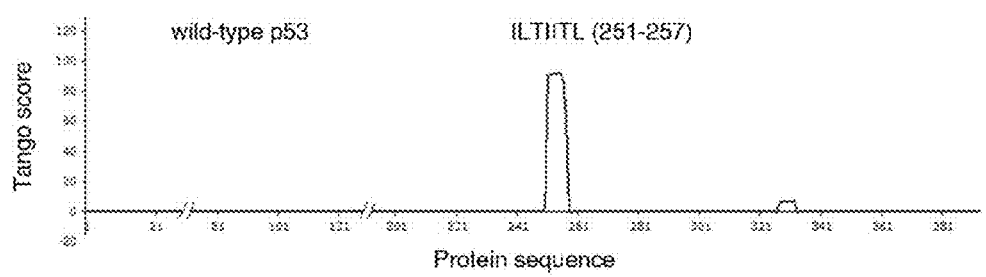

To better understand why structurally destabilized mutations in p53 would induce aggregation, TANGO,[17] an algorithm to predict protein aggregation sequences, was used to identify regions in the protein that would be prone to aggregation. Here, an aggregation-nucleating segment was identified that spans residues 251 to 257 (ILTIITL; SEQ ID NO:2) in the hydrophobic core of the p53 DNA-binding domain (DBD). In the native structure, these residues form a β-strand that is an integral part of the hydrophobic core of the p53 DBD (FIG. 1). Mutations that destabilize the tertiary structure of the DBD are, therefore, likely to increase the exposure of regions that are normally buried in the hydrophobic core,[18] such as the aggregation-nucleating region, and, therefore, also prone to trigger aggregation of the p53 protein by assembly of the aggregation-nucleating stretch into an intermolecular β-sheet-like structure (FIG. 3).

Figure 4:
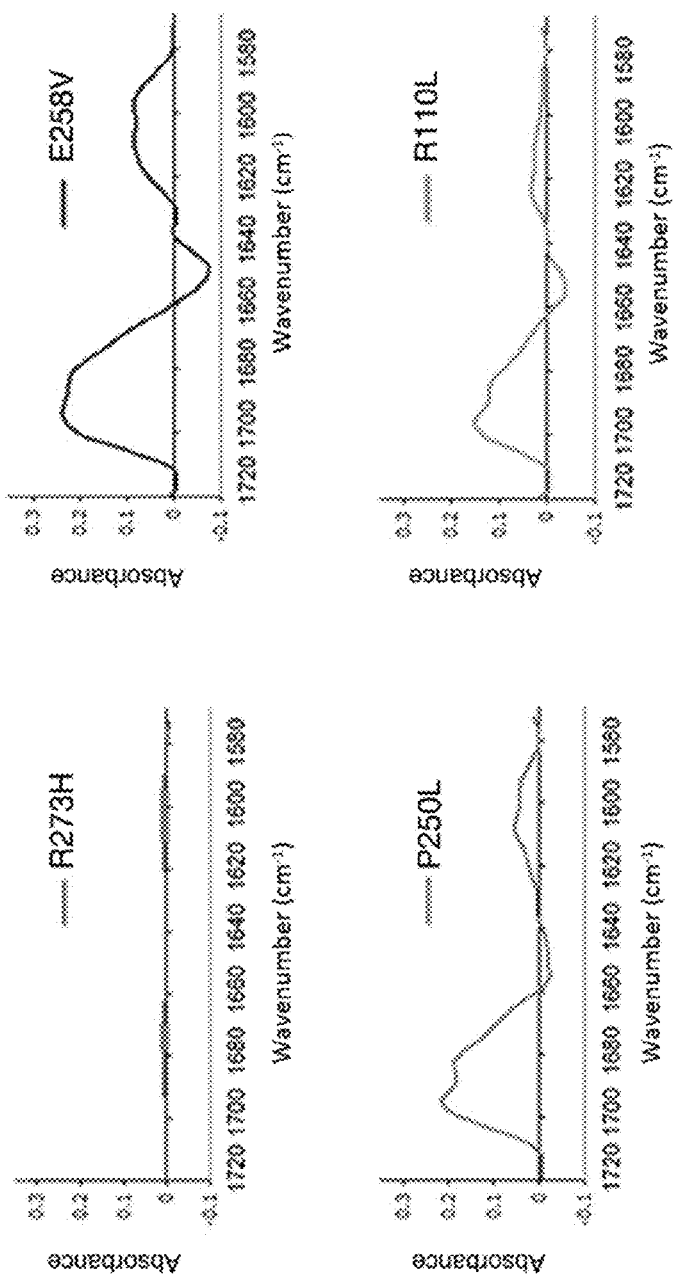
FIG. 4: Characterization on the secondary structure of p53 mutant aggregates. Panel a: FT-IR spectra of p53 mutants purified from cultured cells. The aggregating mutants (P250L, E258V and R110L) showed increased absorbance near 1615 and 1683 $cm^{-1}$. Panel b: FT-IR spectrometry of protein aggregates formed by p53 core domain. The IR absorbance spectrum (plot in red) was estimated for the content of different secondary structures (plots in green). The bands ranging from 1610-1640 $cm^{-1}$ are assigned to β-sheet, 1640-1650 $cm^{-1}$ to random coil, 1650-1660 $cm^{-1}$ to α-helix and 1660-1700 $cm^{-1}$ to β-turn structure. Panel c: FT-IR of proteinase K-digested p53 aggregates. The β-sheet structure was remaining, whereas the other secondary structures (e.g., random coil and α-helix) have largely been lost.
Figure 4:
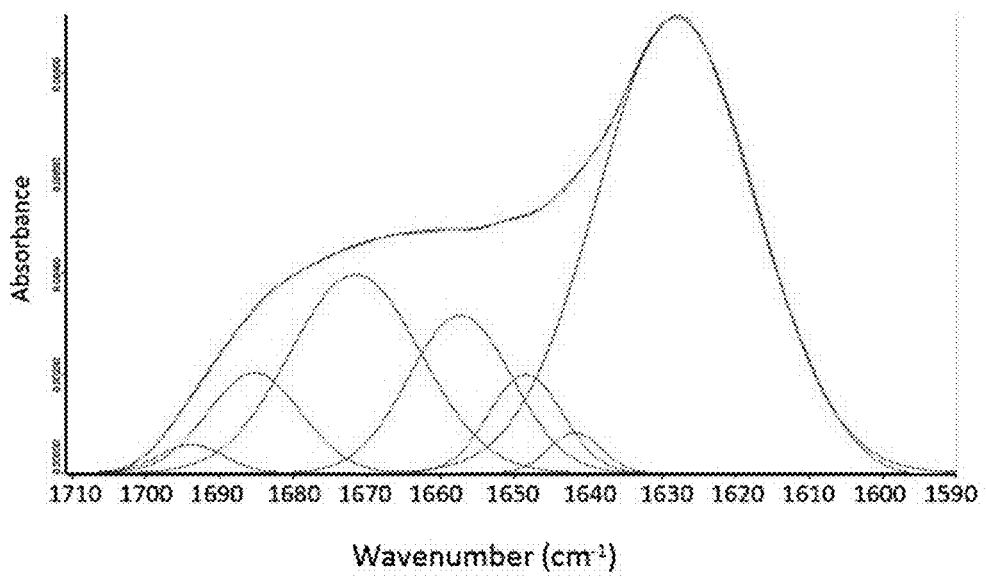
Figure 4:
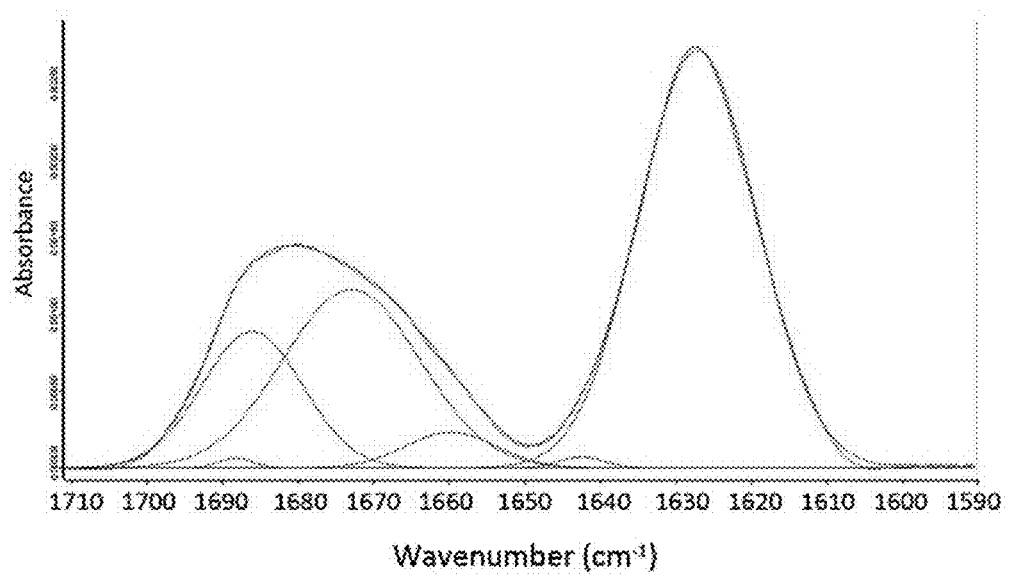

To retrieve information on the secondary-structure content of the p53 mutants, Fourier Transform Infrared (FT-IR) spectrometry was performed. Therefore, Hemagglutinin-tagged p53 (HA-p53) was transiently over-expressed and immunopurified from SaOS-2 cells. Different spectra showed that contact mutants such as R273H had a wild-type conformation, whereas aggregating mutants such as P250L, E258V and R110L had increased absorbance around 1615 and 1683 $cm^{-1}$, consistent with an increase in intermolecular β-sheet structure (FIG. 4, panel a). In addition, when using recombinant p53 DBD, produced in *E. coli*, the formed aggregates had an amorphous macromolecular structure as judged by electron microscopy (data not shown) and were enriched in intermolecular β-interactions as judged by FT-IR analysis (FIG. 4, panel b). These results are consistent with previous findings[19] and support the notion that p53 mutants assemble into higher order polymers via β-aggregation.

In order to confirm that residues 251-257 act as an aggregation nucleus, several strategies were used. First, digesting the aggregates formed by the recombinant p53 DBD with proteinase K, resulted in a proteolytic cleavage product that retained an amorphous morphology (data not shown) with intermolecular β-structure, but that was depleted of other regular secondary structure (FIG. 4, panel c). Subsequent electrospray ionization-mass spectrometry (ESI-MS) analysis yielded peptide fragments covering residues 252-256, thereby confirming the incorporation of these residues in the core of the aggregates. Second, fluorescently labeled peptides encompassing residues 251-257 in SaOS-2 cells were transfected and it was found that they accumulated in perinuclear inclusions (data not shown). Equally, N-terminal fusions of this same peptide were over-expressed to GFP and again found punctuate inclusion formation (data not shown). These experiments show that residues 251-257 have a strong aggregation propensity and are sufficient to induce aggregation of an entire protein.

Example 3

Interfering with the Aggregation Propensity of p53

Figure 5:
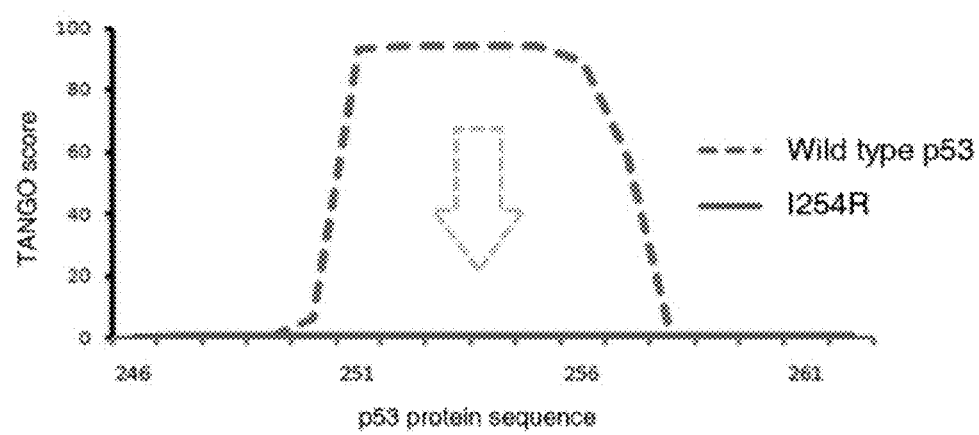
FIG. 5: Validation of aggregation-prone region in p53 DNA-binding domain. Panel a: Predicted effect of mutation I254R on the aggregation propensity of p53. The y-axis shows predicted aggregation propensity (TANGO score) of sequence 251-257. The mutation I254R that introduced positive charge was sufficient to suppress its aggregation propensity. Panel b: BN-PAGE of p53 mutants over-expressed in SaOS-2 cells. The designed mutation I254R suppressed aggregation of E258V and R175H mutants, resulting in sufficient degradation of these mutants. The presence of MG-132 compound inhibited proteasomal degradation of mutant p53, but only resulted in the formation of low molecular-weight species.
Figure 5:
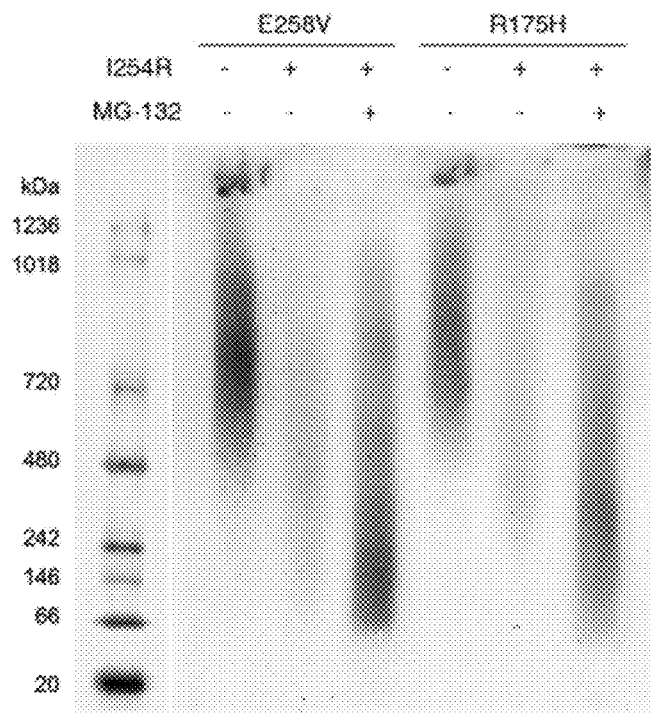

To further reveal the significance of this aggregating zone, an in silico analysis was performed using TANGO, searching for additional mutations that would abrogate the aggregation propensity of that zone. Several mutations with such characteristics were identified and introduced into the p53 expression vectors. An example of such mutation is residue 254, present in the middle of the aggregation nucleus, which were mutated from a hydrophobic to a positive charge (I254R) (FIG. 5, panel a). By introducing this additional mutation, suppressed aggregation of these p53 mutants was expected.

Figure 6:
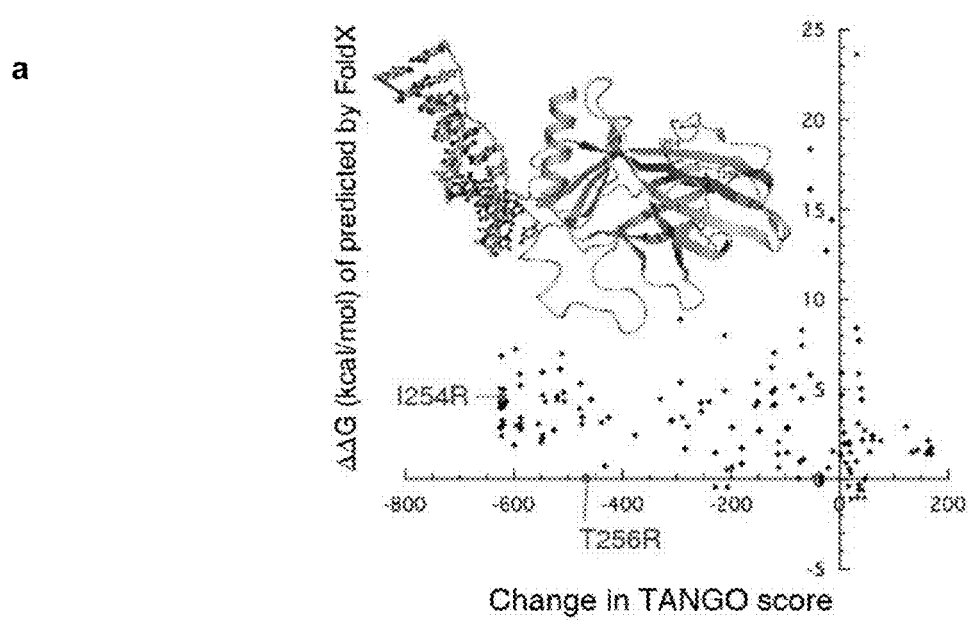
FIG. 6: Effect of T256R mutation on the aggregation of p53 mutants. Panel a: In silico, random mutagenesis screen whereby the change in free energy (y-axis, FoldX prediction) and the change in aggregation propensity (x-axis, TANGO score) were calculated as the difference with the p53WT. The I254R mutation bared a maximal reduction in TANGO score, though this was accompanied by an increase in free energy.
Figure 6:
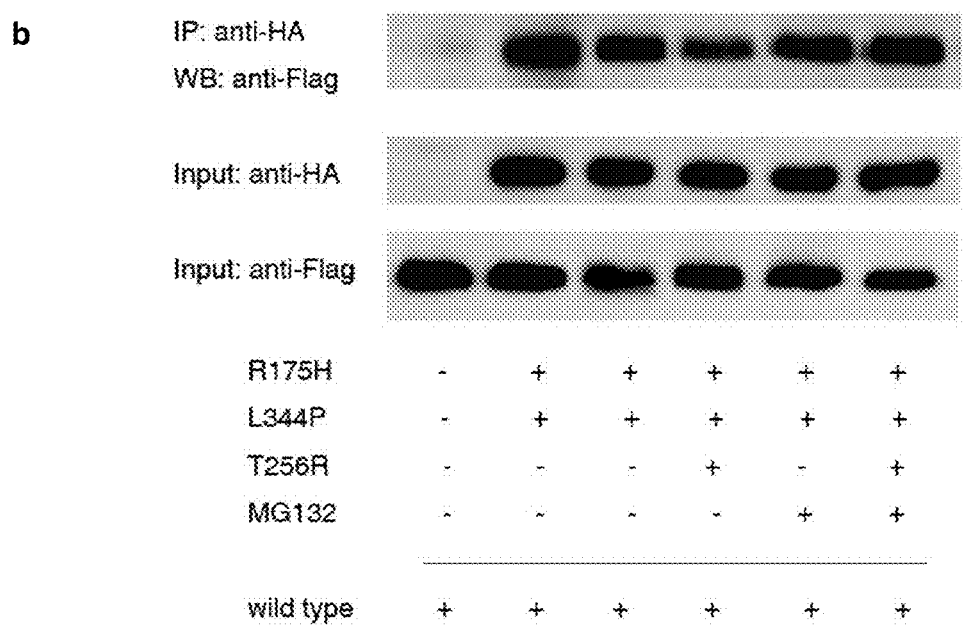
Figure 6:
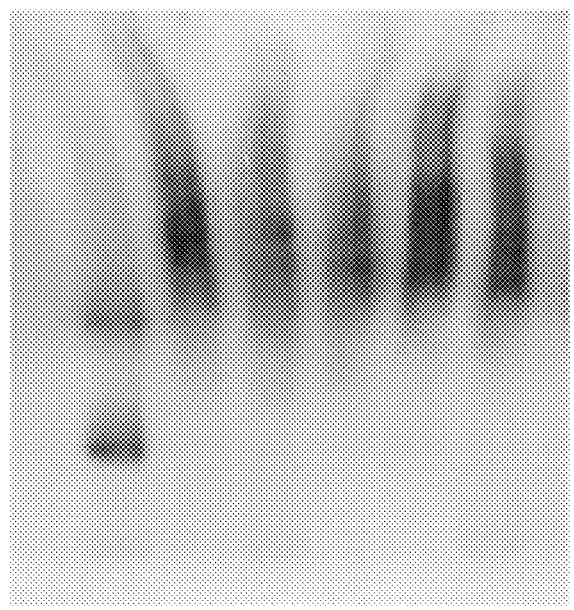

Indeed, when analyzing the double mutant $p53^{E258V/I254R}$ and $p53^{R175H/I254R}$ proteins, on BN-PAGE after transient over-expression in SaOS-2 cells, both failed to aggregate; instead, they were efficiently degraded as indicated by the significant reduction in overall mutant protein levels compared to the wild-type (FIG. 5, panel b). Importantly, even when preventing these double mutants from degradation by adding a proteasomal inhibitor (20 μM MG-132) to the medium, these mutants still did not aggregate into high molecular-weight bands, but instead accumulated as misfolded, but soluble p53 (FIG. 5, panel b). Consistently, the I254R mutation also inhibited the aggregation of the p53 (251-257)-GFP fusion protein, resulting in a homogenous distribution of the protein within the cell (data not shown). On the contrary, another designed mutation T256R, that partially alleviates but does not suppress the aggregation propensity of the protein, did not suppress the aggregation of mutant p53, suggesting the critical role of residues 251-257 in nucleating aggregation (FIG. 6).

Example 4

Aggregation of Destabilized p53 Mutants in Human Tumors

To exclude the possibility of artefacts from over-expression, tumor cell lines carrying endogenous mutant p53, including MOG-G-CCM (p53 R110P) astrocytoma, HT-1376 (p53 P250L) bladder carcinoma, Detroit 562 (p53 R175H) pharynx carcinoma, 1301 (p53 R282W) T-cell leukemia, were analyzed for their cellular distribution of p53. Comparable to the over-expression of most mutant p53 proteins in SaOS-2 cells (see above), a marked punctate staining was observed that accumulated throughout the perinucleus. In contrast, a homogeneous nuclear distribution of endogeneous p53 was observed in U-2 OS osteosarcoma cells (p53 wild-type) and WiDr (p53 R273H) colon carcinoma (FIG. 7; and data not shown), comparable to previous reports.[20]

Importantly, these inclusions stained positive for Thioflavin T, a fluorescent dye that binds preferentially to β-aggregates, indicating that the large inclusions were indeed formed by aggregation. Accordingly, BN-PAGE analysis revealed an increased molecular weight of the endogenous p53 in the mutant cell lines MOG-G-CCM, HT-1376, Detroit 562 and 1301, but not in the U2-OS, WiDr and Ramos Burkitt's lymphoma (p53 I254D) cell lines (FIG. 8, panels a and b). Consistently, cytoplasmic p53 was also found in tumor cells derived from heart, kidney and thymus lymphomas from a knock-in mouse model expressing p53R172H, the mouse equivalent of human mutation R175H.[13]

Finally, a blind screen of samples from ten colorectal adenocarcinomas yielded a single case carrying a point mutation in the DNA-binding domain (R282W). Consistent with results from cultured cell lines, immunofluorescence revealed cytoplasmic inclusions of p53, but no nuclear staining in the mutant sample (FIG. 9). In contrast, no inclusions were found in tumor samples from patients not carrying an aggregating mutation.

Example 5

Structurally Destabilized p53 Mutants Co-Aggregate with Wild-Type p53

To investigate whether the higher aggregation propensity of mutant p53 can lead to co-aggregation of wild-type p53, co-transfection experiments were performed into SaOS-2 cells of HA-tagged mutant p53 and FLAG-tagged wild-type p53. Immunofluorescence showed cytoplasmic retention and co-localization of both wild-type and mutant p53 within aggregates (data not shown). Also in BN-PAGE, wild-type p53 aggregated and co-migrated with mutant p53 upon co-transfection (FIG. 10, panel a). Co-immunoprecipitation experiments of mutant HA-p53 from cell lysates showed tetramerization-independent interaction between aggregating mutant and FLAG-WT p53 (FIG. 10, panel b). Consistent with previous observations, this interaction was also abolished in the presence of the I254R mutation. Similarly, the introduction of positive or negative charges (I254D, I255R and I255D) also prevented mutant p53 from aggregating and interacting with wild-type p53. This observation was specific for the aggregation-nucleating region as the introduction of charges outside this zone did not prevent mutant p53 (co-) aggregation (data not shown).

To determine whether forced cytoplasmic localization caused by a deficient Nuclear Localization Signal (NLS) in p53 could induce aggregation of p53, the K305N mutation that prevents binding of p53 to the NLS receptor was introduced.[21] The resulting NLS mutant did not aggregate, thereby suggesting that the aggregation of p53 is mutation-specific, rather than dependent on the subcellular localization (data not shown).

Example 6

Aggregation-Dependent Dominant-Negative Effects

To validate the concept of dominant-negative activity of mutant-induced wild-type p53 aggregation, the transcriptional activity of p53 was monitored using a PG-13 luciferase reporter plasmid containing 13 contiguous p53 DNA-binding sites in SaOS-2 cells that were transfected with wild-type and/or mutant p53. Reverse transcriptase quantitative-PCR (qPCR) was also performed on four endogenous p53-regulated genes, namely MDM2, BAX, p21 and NOXA.[22] As compared to over-expression of wild-type p53 alone, expression of mutant p53 showed dramatically reduced luciferase activity (FIG. 12, panel a) confirming their loss-of-function phenotype. More importantly, the loss of luciferase activity and target gene expression was also observed upon co-transfection of wild-type and aggregating mutant p53, confirming the dominant character of these disease-related mutations (FIG. 12, panel b).

As previously mentioned, it is largely accepted that dominant-negative activity results from the incorporation of mutant p53 into mixed tetramers.[7] However, the results suggest that the dominant-negative action of conformationally destabilized mutants (more than 30% of reported cases) is exerted through mutant-induced co-aggregation. If the former mechanism is correct, dominance should be strictly dependent on the tetramerization domain (TD). However, if dominance is aggregation-driven, it should also be dependent on the aggregation-nucleation sequence spanning residues 251 to 257.

To distinguish between these two possibilities, aggregating and contact mutants were modified by secondary mutations that suppress tetramerization, aggregation or both. In order to probe tetramerization, p53 mutants were generated that carry both a disease-causing mutation and the tetramerization-suppressing mutation L344P.[23] In order to probe aggregation, mutant p53 was also generated that carries both a disease-causing mutation and the aggregation-suppressing mutation I254R. Finally, as a control, triple mutants were generated combining the disease mutation, the tetramerization-suppressing and the aggregation-suppressing mutations. The dominant-negative activity of these mutants was subsequently tested for their interaction with, and dominant-negative effect on, wild-type p53.

First, the ability of contact mutants R273H and R248W to inhibit p53-induced expression of MDM2, BAX, p21 and NOXA upon co-expression with the wild-type p53 in SaOS-2 cells was assessed. This inhibition was alleviated upon suppression of tetramerization via the L344P mutation, while the aggregation-suppressing mutant I254R had no effect (FIG. 12, panel c), demonstrating that the dominant-negative activity of contact mutants is indeed exerted strictly through tetramerization. In contrast, however, the dominant-negative activity of aggregation-prone mutants E258V and R282W was reduced but not abrogated when tetramerization was suppressed via the L344P mutation. To completely abrogate the dominance of the aggregating mutations, it was necessary to also suppress their aggregation propensity by including the additional I254R mutation (FIG. 12, panel d). This tetramerization-independent interaction was confirmed by co-immunoprecipitation. While both contact and aggregating p53 mutants with an intact tetramerization domain (TD) precipitated together with wild-type p53, only the subset of aggregating p53 mutants was still able to interact with wild-type p53 when the L344P mutation was present (FIG. 10, panel b). Only the loss of the aggregation propensity caused by the I254R mutation (FIG. 11) alleviated the interaction of aggregating mutants with wild-type p53. BN-PAGE further confirmed that introduction of the L344P mutant converted wild-type p53 as well as the contact mutant R273H and R248W into p53 monomers. In contrast, aggregating p53 mutants R282W and E258V still formed large aggregates in the presence of the L344P mutation, and did not show a monomer band in BN-PAGE, whereas wild-type p53 still co-migrated as high molecular weight species (FIG. 12, panel e). Together, these data indicate that, contrary to contact mutants, the dominance of structurally destabilized mutants originates from their increased aggregation propensity.

To exclude that the suppressive effect of the I254R mutant results from increased mutant degradation rather than from a suppression of its aggregation propensity, the effect of the I254R and L344P mutants on the dominance of disease mutants in the presence of the proteasomal inhibitor MG-132 was measured. Under these conditions, the ability of the contact mutant R273H to interact with wild-type p53 and to interfere with p53-induced expression of MDM2, BAX, p21 and NOXA upon co-expression with the wild-type p53 in SaOS-2 cells was again strictly dependent on tetramerization (data not shown).

The dominant-negative activity of the aggregating mutant R175H again showed a more complex behavior than the contact mutant and could only be abrogated when both tetramerization and aggregation were suppressed simultaneously. Co-immunoprecipitation and BN-PAGE of wild-type p53 with the R175H mutant in the presence of the proteasomal inhibitor MG-132 further confirmed these effects. Co-precipitation of wild-type p53 with R175H could only be abrogated when both tetramerization and aggregation were suppressed. Wild-type was precipitated with the mutant, however, only when either tetramerization or aggregation were suppressed. Moreover, BN-PAGE showed a clear difference in the oligomerization state of the precipitated wild-type p53 in both cases. Whereas wild-type p53 forms high-molecular weight aggregates in the presence of the tetramer-incompetent R175H/L344P, wild-type p53 remains tetrameric in the presence of the aggregation-incompetent R175H/I254R (data not shown).

Together, these data demonstrate that the dominant-negative effect of structurally destabilized mutants is determined by aggregation, and that the tetramerization domain cooperates with the aggregation-nucleating region to co-precipitate wild-type p53 into aggregates.

Example 7 p53 Aggregation Inactivates p63 and p73 by Co-Aggregation

As already mentioned above, a pivotal mechanism in the tumorigenic characteristics of mutant p53 is to interact with and attenuate the function of its paralogues p63 and p73. These are members of the p53 gene family (63% identity of p53 with p73, and 60% of p53 with p63), and their transactivation (TA) isoforms have partial functional overlap with p53. Although p63 and p73 are rarely mutated in tumors, their functions are frequently inhibited by mutant p53 leading to an increase in oncogenic potential of the affected cells.[13, 24]

Inactivation is probably achieved by direct interactions between mutant p53 and its paralogues involving interactions between the DNA-binding domains of p53 and its paralogues by an undetermined mechanism.[25] Due to a low structural conservation of their tetramerization domains, p53 and its paralogues cannot tetramerize and, therefore, the interaction should be tetramer-independent.[26] Using TANGO, it was found that p53, p63 and p73 encode highly conserved aggregating sequences in the same structural motif (FIG. 13). Since co-aggregation of proteins depends strictly on sequence similarity rather than hydrophobicity,[27] mutant p53 might also be able to induce co-aggregation and inactivation of p63 and p73. To investigate this hypothesis, mutant p53 and the transactivation domain (TA) of p63 or p73 (TAp63α/TAp73α) were co-expressed in SaOS-2 cells. In the presence of wild-type p53, both p63 and p73 predominantly localized to the nucleus; in contrast, co-expression of aggregating p53 mutants (R282W and R110P) with TAp63α/TAp73α, drove p63 and p73 into perinuclear aggregates. The aggregates of mutant p53 and p63/p73 showed strong co-localization inside vimentin-caged aggresomes. Addition of nocodazole disrupted the vimentin network and resulted in diffused punctuate aggregates in the cytoplasm, confirming the aggresomal co-localization of aggregated p53 and its paralogues. Co-expression with the p53 NLS mutant K305N (see above) did not alter the localization of p63 and p73, demonstrating that subcellular localization of p53 per se is not sufficient to retain p63 and p73 in the cytoplasm (data not shown).

BN-PAGE showed that in the presence of wild-type p53 or contact mutants (R248W, R273H), native p63 and p73 exist as monomers, tetramers and octamers. In the presence of aggregating p53 mutants (R110L, E258V, R175H, R282W and R249S), p63 and p73 instead form large aggregates (data not shown).

Immunofluorescent labeling of p53 and p73 in kidney lymphoma of p53$^{R172H/H}$ transgenic mice, as well as in liver and lung metastasis of osteosarcoma in p53$^{R172H/+}$ mice, showed that p73 co-localized with p53 in cytoplasmic inclusions. Consistently, in human colon carcinoma tissues carrying p53 mutant R282W, p73 also co-localized with p53 in cytoplasmic inclusion aggregates (data not shown).

To examine the role of the aggregating sequences of p53 (251-257; SEQ ID NO:2), p63 (321-327; SEQ ID NO:4) and p73 (271-277; SEQ ID NO:3) in the interaction and aggregation of p53 with p63 and p73, the aggregation-suppressing mutations p53(I254R), p63(I324R) and p73(I274R) were analyzed by co-immunoprecipitation. Upon co-expression in SaOS-2 cells, contact mutants R273H and R248W interacted only very weakly with p63 and p73 (FIG. 14, panel a and FIG. 15, panel a); this was in contrast to the aggregating p53 mutants R175H, R282W and R110P that strongly interacted with p63 and p73. Introduction of aggregation-suppressing mutations completely abolished the interaction between p53 and its paralogues. Likewise, p63 I324R or p73 I274R did not interact with p53 R282W (FIG. 14, panel a and FIG. 15, panel a).

The role of mutant p53 aggregation on the functional inactivation of p63 and p73 was also addressed by measuring their transactivation activity on MDM2, p21 and BAX genes by RT-qPCR. While expression of p63 or p73 solely induced the expression of the different reporter genes, co-expression with the p53-aggregating mutant R282W substantially inhibited p63 and p73 function (FIG. 14, panel b and FIG. 15, panel b). Importantly, suppression of the aggregation propensity of p53-R282W by introduction of the I254R mutation restored the transcriptional activity of p63 and p73, showing that co-aggregation with mutant p53 is responsible for their inactivation (FIG. 14, panel b and FIG. 15, panel b). To exclude any functional overlap with p53, the effect of p53 mutants on genes that are exclusively regulated by p73 was also tested. Expression of p57$^{Kip2}$ and Jun-B[28, 29] which regulate p53-independent apoptosis pathways, was increased by p73; this increase was significantly inhibited upon co-expression with the p53 R282W mutant. Again, suppression of aggregation in p53 R282/I254R fully restored p73 function (FIG. 14, panel c). To exclude the possibility that the loss of activity observed for the I254R variants results from proteasomal degradation rather than a suppression of their aggregation propensity, the qPCR experiments were repeated in the presence of MG-132 and yielded similar results (FIG. 14, panel b and FIG. 15, panel b).

These results demonstrate that the gain-of-function activity of structurally destabilized mutants results from their increased aggregation propensity allowing them to co-precipitate p63 and p73 into inactive cellular inclusions.

Example 8 p53 Aggregation Up-Regulates Hsp70 and Hsp90

Heat Shock Proteins are frequently found to be over-expressed in a wide range of tumors, and members of several chaperone families have been demonstrated to promote tumor cell proliferation and inhibit cellular death pathways.[30] As protein denaturation and aggregation are powerful triggers of heat shock response, the accumulated p53 aggregates may acquire anti-apoptotic properties through the activation of heat shock proteins. In order to study the effect of p53 aggregates on the expression level of two important cancer-related chaperones Hsp70 and Hsp90,[31, 32] wild-type and mutant p53 were over-expressed in the SaOS-2 cells and chaperone levels were examined by Western Blot and qPCR. While over-expression of the contact mutant R273H resulted in chaperone levels similar to those seen with wild-type p53, over-expression of the aggregating mutant R175H induced a substantial up-regulation of both Hsp70 and Hsp90 (FIG. 14, panels d and e). Suppression of the aggregation propensity in the disease mutant R175H by the additional mutations I254R or I254D restored wild-type chaperone levels.

Example 9 p53 Aggregation, LOH and Patient Survival

Further analysis as to whether aggregation of mutant p53 leads to stronger dominant-negative effect and lower survival rate in human tumors was performed. If the wild-type p53 allele is strongly inhibited by the mutant, a lower rate of loss of heterozygosity (LOH) should be observed. Consistently, analysis of the p53 germline mutation database (129 cases)[33] revealed that tumors that carry DNA contact mutations display approximately two-fold higher rate of LOH than those with destabilized mutations (p<0.01, FIG. 16, panel a). The lower selective pressure for loss of the remaining wild-type p53 allele in destabilized germline mutations suggests a stronger dominant-negative effect of structurally destabilized aggregating mutants. When independent studies were compiled on patient survival (623 cases),[34, 35] it was found that the patient's long-teen survival was significantly higher for contact mutants than for aggregating mutants (p<0.01, FIG. 16, panel b). The poorer prognosis of patients carrying aggregating mutants supports the model that p53 mutants gain oncogenic function through aggregation.

Example 10

Structural Basis of p53 Aggregome

In the above examples, it was demonstrated that the inactivation of p63 and p73 by mutant p53 is determined by a specific aggregation-prone sequence in its DNA-binding domain encompassing residues $^{251}$ILTIITL$^{257}$ (SEQ ID NO:2; further termed p53β) that becomes exposed in mutant p53. Association of p53β with the homologous sequences in WT p53, p63 and p73 results in mutant p53-induced aggregation and inactivation of both WT p53 and its paralogues. It was then investigated whether aggregation-induced interactions mediated by p53β could be at the origin of a broader rewiring of the mutant p53 interactome and its gain-of-function. More specifically, examination was performed as to whether evolutionary unrelated proteins sharing only a p53β-like sequence were also susceptible to specific interactions and aggregation with mutant p53 and whether this also led to their functional inactivation. Using a peptide-based interaction assay, novel p53β interacting peptides were identified from a variety of proteins belonging to cell growth and apoptotic pathways. Subsequently, by using the full-length proteins from a selected subset, p53β-specific interactions and co-aggregation of these proteins with mutant p53 in cultured cells were validated, and more importantly, also in clinical samples of human tumors. Eventually, the inhibitory nature of these interactions was demonstrated by showing how specific, mutant p53-mediated aggregation of copine-2 and caspase-8 stimulates Erk phosphorylation and inhibits apoptosis. Overall, these data illustrate the existence of a mutant-induced p53 aggregome with gain of proliferative function, and provide a specific structural mechanism explaining its emergence (schematic representation in FIG. 17, panel a, and illustrated in Examples below).

Example 11 p53β Interacts with Homologous Peptides of Unrelated Proteins

In the above examples, it was demonstrated that aggregation between members of the p53 family is determined by the interaction of p53β ($^{251}$ILTIITL$^{257}$; SEQ ID NO:2) with the equivalent aggregation-prone sequences in both p63 (p63β: $^{321}$ILIIVTL$^{327}$; SEQ ID NO:4) and p73 (p73β: $^{321}$ILII-ITL$^{327}$; SEQ ID NO:3), resulting in their functional inactivation. Although not identical, the p63β and p73β sequences are highly homologous to p53β, with only two and one mismatched amino acids, respectively. This is in contrast to the relatively lower homology at the whole protein level (49% sequence identity for p63 and 48% for p73). As aggregation of an entire protein is determined by such short aggregating peptide sequences rather than by overall homology,[73] investigation was performed to determine whether the presence of a p53β-like peptide in evolutionary unrelated proteins is sufficient for co-aggregation with mutant p53.

In order to identify aggregating peptides that match p53β, the human proteome for peptides that have high homology with the p53β peptide were screened. While p53β is unique to p53, in silico analysis identified 56 additional peptides (Table 2) that have no more than two mismatches with p53β. Subsequently, the ability of the selected peptides to interact with p53β using an in vitro peptide-binding assay was empirically determined. Therefore, the 56 selected peptides were spot-synthesized on a cellulose membrane, which was subsequently incubated with biotinylated p53β peptide (FIG. 17, panel b). After washing, the membrane was treated with streptavidine-HRP to detect p53β binding (FIG. 17, panel c). Consistently, the assay successfully identified control peptides including p53β itself, as well as the equivalent sequences from p63 and p73. Among the 56 peptides probed, six p53β interacting peptides having a similar affinity as p53β for itself (75-110% of signal intensity compared to p53β self-interaction) (Table 1) and 27 peptides displaying weaker interaction (between 10-50%) (Table 2) were identified. Interestingly, some of the strongest interacting peptides stem from proteins that have an overall sequence identity with p53 below 15%. The sequence identity between p53β and their interacting peptide, however, is 75%. Although the function of the proteins from which these 33 interacting peptides stem is often poorly characterized, some interesting cases can be identified. Along with the previously identified p63 and p73, which are inactivated by mutant p53 in cancer, segments were found belonging to Copine-2 (CPNE2), which is a negative regulator of growth factor signaling,[72] methionine synthase (METH), which has been associated to methionine dependence in tumors,[64] CGRF1, a negative regulator of cell proliferation,[67] and caspase-8 (CASP8), a key element for apoptosis, the inactivation of which is associated to chemoresistance and found in a variety of human cancers.[66]

From the peptide blot, it was also clear that sequence similarity alone was not sufficient to induce interaction and co-aggregation with p53β, as some target sequences, despite an identical overall identity, did not interact with p53β. Analysis of the sequence determinants of co-aggregation by multiple sequence alignment and conservation scoring was begun. In order to allow clear-cut analysis, the sequence features of the eight strongest interacting peptides (intensity >40% compare to p53β self interaction) were compared to the twenty peptides that show least interaction intensity (intensity <10%). In FIG. 18, panel a, the conservation per position is shown as "log-odd" values, i.e., the logarithm of the probability that the position is more conserved in the interacting peptides versus the non-interacting set. This approach is required in order to correct for sequence biases in small datasets and positive values indicate enrichment in the positive set. The analysis revealed strong sequence conservation of I251, L252, I254 and T256 for the interacting peptides and low conservation in the intervening positions. With the exception of Ile251, these residues follow an (i,i+2) pattern consistent with an extended β-strand conformation on which conserved residues cluster to form a structurally conserved β-sheet interface, whereas the variable residues form the opposing variable β-sheet interface (FIG. 18, panel b). Sequence variability at the positions 252, 254 and 256 is very low and restricted to conservative mutations (mostly at position 256). Importantly, mutation of these positions to charged residues leads to a strong reduction of p53β interaction. Conversely, conservation on the intervening positions 253, 255 and 257 is not selected for in the interacting peptides. The structure-activity analysis presented here suggests that p53β-pepspot interaction is indeed geared by beta-interactions, such as observed in the core of aggregates of many proteins.[65, 70] Moreover, the beta interaction that emerges from the pepspot interactions is in agreement with a β-strandmediated mode of interaction found in crystal structures,[71] whereby a conserved β-sheet interface provides the structural substrate for co-aggregation.

Example 12 p53β Mediates the Interaction and Co-Aggregtion of Mutant p53 with Multiple Proteins In order to test whether p53β can mediate the interaction and co-aggregation of full-length proteins with mutant p53, full-length clones were obtained for a subset of nine proteins containing peptide sequences whose interaction with p53β in the pepspot assay spanned the full intensity range (FIG. 17, panel c). This set encompassed the known interactors p63 and p73, but also comprised potentially novel p53 interacting proteins containing p53β like sequences. Apart from CPNE2 and CASP8 mentioned earlier, the set was composed of Annexin-6 (ANXA6), Cyclin-I2 (CCNI2), T-cell activation GTPase-activating protein (TAGAP), a putative ATP-dependent RNA helicase (DHX33), and a poorly characterized coiled-coil domain protein (CC132).

Upon transient co-expression of these target proteins (fused to a FLAG epitope sequence) with the aggregation-prone mutant p53R175H (fused to an HA epitope sequence) in HeLa cells, a first indication of interaction was detemmrined from quantifying the colocalization as Pearson's coefficients in confocal immunofluorescence microscopy images (data not shown). In general, proteins that strongly colocalized with p53R175H (e.g., copine-2, annexin-6 or the previously identified p63 and p73) in HeLa cells were also the proteins from which the peptide fragment displayed a strong interaction with p53β in the peptide-binding assay (Table 1); whereas proteins that showed little colocalization with p53R175H (e.g., DHX33 and TAGAP) were also poor binders to p53β at the peptide level. In fact, a plot of the Pearson's correlation coefficients of colocalization against the quantified intensity obtained in the peptide blot assay, resulted in a correlation between these values ($R^2=0.78$), suggesting that for these proteins, the interaction is to a large extent geared by the short p53β sequence. On the other hand, individual points deviate significantly from linearity, showing that the structural stability of the target protein and the exposure of its p53β-like sequence modulates the basic propensity to co-aggregate with p53β that is given by the peptide fragment.

When the seven novel target proteins are co-expressed with WT p53 or the non-aggregating p53R273H contact mutant, only poor colocalization was observed. In addition, the non-aggregating control mutant p53R175HI254R also fails to colocalize with these proteins. These data demonstrate that colocalization between the target protein and p53 is dependent on the increased aggregation propensity of misfolded p53R175H, which is mediated by p53β.

To demonstrate that colocalization results from direct interaction between p53R175H and the target protein, co-immunoprecipitation experiments were performed. There, the same interactions between p53R175H and the target proteins were found, which correlated well with the peptide binding assay (see higher). However, for WT p53, p53R273H as well as for p53R175HI254R, no interactions with the target proteins could be observed (FIG. 19), confirming that p53β mediated the interactions between the destabilized p53R175H mutant and target proteins.

To further probe the conformational dependence of these interactions, the effect of the mutant p53 conformation on the co-aggregation of the target proteins by Blue Native-PAGE (BN-PAGE) and Western blot was investigated. Upon co-expression of the target proteins with either the wild-type p53 or p53R273H, both p53 and the target proteins mainly migrated independently as bands corresponding to their native molecular weight (FIG. 20). However, co-expression with p53R175H resulted in the formation of high molecular-weight species (on the upper part of the gel) of both the target protein and p53R175H, concomitant with a decrease in native protein levels. This observation is consistent with the presence of both aggregated p53 and co-aggregated target proteins (FIG. 20). These data validate the notion that colocalization and interaction of p53R175H with the target proteins are dependent on the conformational status of p53. Indeed, when p53 adopted its native conformation, the target proteins could also fold properly and maintain their native status. However, when p53 was strongly aggregated, the target proteins also aggregated and co-migrated with mutant p53 as high molecular-weight species on a native gel.

Finally, to confirm the determining role of the p53β peptide in the interaction and aggregation of p53 with the target proteins, p53β was fused to GFP and then this fusion was co-expressed pairwise with the target proteins. As with full-length p53, the p53β-GFP fusion colocalized with the target proteins. On the contrary, upon suppression of the aggregation propensity of p53β by including the I254R mutation (p53β-IR-GFP), colocalization of GFP with the target proteins was abbrogated. Similarly, a non-aggregating sequence fragment of p53 ($^{307}$ALPNNTS$^{313}$; SEQ ID NO:57) fused to GFP did not colocalize with the target proteins. Consistent with the poor specific colocalization of full-length DHX33 with p53R175H, the aggregation-prone sequence of DHX33 (DHX33β-GFP) fused to GFP also failed to colocalize with p63, p73, copine-2 and caspase-8, although it formed cytoplasmic aggregates. Finally, co-immunoprecipitation experiments confirmed that the observed colocalization resulted from direct p53β-mediated aggregation-specific interactions. Indeed, p53β-GFP co-immunoprecipitated with the target proteins, whereas the p53β-IR-GFP, $^{307}$ALPNNTS$^{313}$-GFP or DHX33β-GFP did not (FIG. 21).

Two candidates were selected for further analysis that showed consistent and specific co-aggregation as full-length proteins and for which functional assays were readily available with p53R175H, namely copine-2 and caspase-8. Below, the functional effects resulting from co-aggregation with p53R175H were described and show how mutant p53-induced aggregation results in superimposed inactivation of copine-2 and caspase-8.

Example 13

Copine-2 Aggregation and Mutant p53 Aggregation are Associated in Tumor Cell Lines and Human Tumors Copine-2 was identified as a strong positive hit in the above assays. Copine-2, a member of the copine family of calcium-dependent membrane-binding proteins, is widely expressed in various tissues.[68] In order to test whether copine-2 can co-aggregate with mutant p53 under endogenous expression conditions, the localization of p53 and copine-2 in human tumor cell lines and clinical tissues samples were analyzed (data not shown). By immunofluorescence, it was found that endogenous wild-type p53 (U-2 OS osteosarcoma cells) and contact mutant p53R273H (WiDr colon carcinoma), localized in the nucleus. In both cases, copine-2 was either expressed at low level (U-2 OS) or showed homogenous distribution in the whole cell (WiDr). However, in the cells expressing p53 mutant R175H (Detroit 562 pharynx carcinoma) and R110P (MOG-G-CCM astrocytoma), both p53 and copine-2 were found in perinuclear aggregate-like structures. Suppression of endogenous p53 expression by siRNA abolished the formation of copine-2 aggregates, suggesting that mutant p53 was the cause of copine-2 aggregation. In a human colon carcinoma tissue sample that carried p53 mutant R282W, both p53 and copine-2 were found to be colocalized in perinuclear aggregates. As a control, a human colon carcinoma bearing wild-type p53, displayed nuclear p53 staining and homogenous distribution of copine-2.

Example 14

Mutant p53-Induced Aggregation Inactivates Copine-2 and Enhances EGF Signaling

Previous studies have suggested that copine-2 binds to MEK1, a mitogen-activated protein kinase (MAPK) kinase, and, therefore, might be involved in the regulation of MAPK activation.[72] In addition, MAPK (ERK) signaling has been involved in increased prostate cancer progression by mutant p53, partly explained by increased ERK1/2 signaling through EGF (Sauer, et al., *Oncogene* 2010, p. 2628). As the duration and the intensity of MAPK signaling can profoundly modify the biological outcome, the effect of copine-2 on ERK1/2 phosphorylation in the context of a cellular response to EGF was tested. Here, it was found that copine-2 tempered the phosphorylation of ERK1/2, thus suggesting a negative regulatory effect on EGF-dependent cell signaling (FIG. 22, panels a and b). By analyzing previously published microarray data,[69,77] it was found that copine-2 was significantly down-regulated in malignant oncocytomas (t-test, p<0.0001) and immune-resistant cancer cells (t-test, p<0.001; data not shown), being consistent with the notion that copine-2 has an antiproliferative function. Moreover, co-expression with mutant p53 R175H abrogated the ability of copine-2 to temper ERK1/2 phosphorylation, resulting in higher levels of activated ERK1/2 (FIG. 22, panels a and b).

Example 15

Agent Disrupting Co-Aggregation of Mutant p53 and Copine-2

Consistent with the above data, knock-down of endogenous aggregating mutant p53 in MOG-G-CCM and Detroit-562 cells by RNAi (sc-29435, Santa Cruz Biotechnology) rescued copine-2 function and decreased ERK1/2 phosphorylation upon EGF stimulation, an effect that was not observed for the WiDr cells expressing non-aggregating mutant R273H (FIG. 22, panel c). These results suggest that mutant p53 aggregation may potentiate the EGF-dependent cell proliferation signaling pathway by co-aggregation with copine-2, which negatively regulates ERK phosphorylation.

Example 16

Mutant p53 Aggregation Suppresses Caspase-8 Function Through Interaction with the p53β Peptide Since caspase-8 also showed interaction with mutant p53 in the peptide-binding and co-IP assays, tests were performed to determine whether mutant p53 may interfere with the function of co-expressed caspase-8. To this end, Hela cells were stably transfected with p53 mutant R175H and caspase-8, and activity of caspase-8 was measured by the cleavage of labeled substrate (IETD-pNA(acetyl-Ile-Glu-Thr-Asp p-nitroanilide). Compared to the cells transfected with caspase-8 alone, the coexpression of aggregating mutant p53 yielded significantly lower caspase-8 activity (FIG. 22, panels d and e).

Example 17

Agent Disrupting Co-Aggregation of Mutant p53 and Caspase-8

Consistent with the above data, knock-down of endogenous p53-aggregating mutants in MOG-G-CCM (R110P) and Detroit-562 (R175H) cells by RNAi (sc-29435, Santa Cruz Biotechnology) rescued caspase-8 activity. Again, such effect was not detected in the WiDr cells that carried non-aggregating mutant R273H (FIG. 22, panels f through h).

Example 18 p53β-Mediated Aggregation is Associated to Increased Cell Proliferation

To further address the relevance of p53β-mediated aggregation on cell tumorigenicity, 4T1 breast cancer cells that are devoid of endogenous p53 were used. In these cells, the target protein was first co-transfected (either copine-2 or caspase-8) with wild-type p53, mutant p53 R175H or p53 R175H/I254R. Comparable to the observations in Hela cells, co-immunoprecipitation experiments showed no interaction between wild-type p53 and the target proteins, whereas the mutant p53 R175H showed strong physical association with copine-2 and caspase-8. The latter interaction could moreover be abolished by introducing the I254R mutation (FIG. 23, panels a and b).

In order to assess whether a reduced aggregation propensity (by introducing the I254R mutation) would affect the gain-of-function capacity of mutant p53 R175H, the proliferation capacity of 4T1 cells, stably transfected with either empty vector, mutant p53 R175H or p53 R175H/I254R, was also analyzed. As compared to cells not expressing p53, the p53 R175H mutant significantly accelerated cell proliferation. As suggested by the previous findings, this acceleration could be counteracted by introducing the aggregation-suppressive I254R mutation on top of the R175H mutation (FIG. 23, panels c and d). This demonstrates that by inhibiting the aggregation propensity of mutant p53, its gain-of-function activity can be suppressed. In addition, the ability of tumor cells to grow in absence of anchorage, depends on their ability to overcome apoptosis ("anoikis") and to proliferate. Consistent with the other observations, mutant p53 R175H conferred enhanced clonogenic capacity to 4T1 cells seeded in soft agar, whereas p53 R175H/I254R completely abrogated this capacity (FIG. 23, panel e).

Overall, these data strongly suggest that an important part of the gain-of-function features of structurally destabilized p53 mutants, can be explained by their aggregation behavior.

Example 19

WT p53 is Aggregated in Various Tumor Samples

Tumor-suppressor p53 is mutated in approximately 50% of human cancers. However, this means that p53 is still in its wildtype configuration in the other 50% of cases. As shown in the above examples, the aggregation of structurally destabilized p53 mutants displays oncogenic gain-of-function activity by co-aggregation with various tumor suppressors and pro-apoptotic proteins. In addition, it is known that the DNA binding domain of p53 is only marginally stable, making it susceptible for aggregation.[52]

By immuno-histochemical analysis of various clinical tumor samples, it was observed that, even in the absence of mutant p53, wt p53 could aggregate. This was observed in different types of tumors including melanoma and prostate cancer, and this both in established cell lines and clinical tumor samples. Indeed, when staining for p53 in the prostate cancer cell line LNCaP (both wt and a line that was made resistant to androgen receptor signalling), and in several melanoma cell lines (Mel1617, MM031), cytoplasmic inclusions of p53 were observed (FIG. 24). To ensure that we were not observing the structurally destabilized mutant p53, all the cell lines and clinical samples were subjected to sequencing. No mutations could be observed in the p53 coding region, showing that also p53 WT can aggregate in a tumor environment. When staining clinical samples showed aggregated p53, the aggregated nature of these inclusions was confirmed by staining them with oligomer-specific antibody (A11), which was initially designed to detect oligomers of Amyloid β, but which turned out to recognize the β-sheet structural aspects of aggregated proteins. When co-staining p53 and A11 in a sample of colorectal cancer showing cytoplasmic p53, nearly perfect co-localization was observed showing that p53 is indeed present in an aggregated state (FIG. 25).

Example 20

WT p53 Aggregates Upon Chemotherapy-Induced Expression

It is becoming increasingly evident that resistance is also seen in cancers harboring wild-type p53, which might be explained by a change of conformation of wt p53 into a "mutant configuration."[76] Cell lines harboring wt p53 were used and enhanced the expression using previously described chemotherapeutic agents. As expected, Western blot analysis showed that upon cisplatin treatment, U2OS tumor cells started to accumulate WT p53. This was only mediated at the protein level as no changes were observed at the RNA level. However, when performing native page analysis, part of p53 ran as a high molecular weight smear, suggesting the presence of aggregates (FIG. 26). This smear was comparable to the observation in cells that had been treated with compounds inhibiting the proteostatic machinery (MG132 and Bortezomib). When performing immunofluorescent staining for p53 in U2OS cells, increased accumulation of non-soluble, inclusions of p53 in the cytoplasm was subsequently observed. The features of these inclusions were subsequently analyzed using the InCell Analyzer 2000 (>1000 cells/condition), in which a greater than three-fold increase in cytoplasmic aggregates in U2OS cells upon treatment with cisplatin was observed (FIG. 27).

When analyzing the status of p53 in histological samples of cisplatin-resistant ovarium tumor tissue or end stage prostate samples, p53 could be observed in large aggreosome-like inclusions. Importantly, these aggregates consisted of only WT p53 and not mutant p53. Strikingly, these inclusions could occur either in the cytoplasm but were also observed in the nucleus, as confirmed by A11 staining (FIG. 28).

II. Characterization of Other Tumor-Suppressor Aggregromes

Example 21

Generalization of Concept of Aggregation for Other Tumor-Suppressor Proteins

Next, testing was performed to determine whether other tumor-suppressor proteins, such as p16 and its paralog p15, or PTEN, might also exhibit aggregation propensity, either in vitro or in different tumor contexts.

Therefore, p16 and its paralog p15 in HeLa cells were first over-expressed, making use of the mammalian expression vector pCMV, in a similar way as was described above for p53. Immunofluorescence revealed a reduced nuclear staining for p16 and p15, with a compensatory increase of cytoplasmic staining, with the latter regularly containing "punctate" cytoplasmic spots. A punctate staining suggested the assembly of p16 and p15 tumor-suppressor proteins into large aggregates within the perinucleus (FIG. 29).

In a similar way, wild-type PTEN, mutant PTEN 800 del A, PTEN R173C and PTEN R173P were over-expressed in HeLa cells. The mutants show clear perinuclear aggregates (FIG. 30).

To exclude the possibility of artifacts from over-expression, tissue samples from human tumors were analyzed for the cellular distribution of a variety of tumor-suppressor proteins. For example, it could be confirmed that cytoplasmic accumulation of p16 was also observed in tissue samples from ovarian tumor (data not shown).

In conclusion, the above data provide evidence for a generalization of the concept of aggregation for other tumor-suppressor proteins. Further to that, bioinformatic analysis (data not shown) indicated that several other tumor suppressors have similar profiles.

Example 22

Analysis of the Aggregation Propensity of p16 and PTEN

Analysis of the intrinsic aggregation propensity of p16 using the TANGO algorithm reveals one region with an aggregation propensity score higher than 20: TLVVLH (SEQ ID NO:84). One other protein was identified that contains an identical short sequence segment: the p16 homolog p15 (also containing TLVVLH (SEQ ID NO:84)).

Analysis of the intrinsic aggregation propensity of PTEN using the TANGO algorithm reveals five regions with an aggregation propensity score higher than 20, spread out through the entire sequence: $_{132}$VMICAYLLH$_{140}$ (SEQ ID NO:58), $_{173}$YVYYYSYLL$_{171}$ (SEQ ID NO:59), $_{190}$VALLF$_{194}$ (SEQ ID NO:60), $_{269}$MFHF-WVNTFF$_{268}$ (SEQ ID NO:61), $_{314}$YLVLTLT$_{320}$ (SEQ ID NO:62). Two other proteins were identified that contain a similar short sequence segment: the PTEN homolog Tensin-3 (containing YLVLNLS (SEQ ID NO:63)) and the unrelated protein Osgin1, for Oxidative stress growth inhibitor, (containing VALLF (SEQ ID NO:60)).

In order to probe the aggregation-dependent interaction between PTEN and its homolog Tensin, co-immunoprecipitation was performed of both proteins when transiently over-expressed in Hek293 cells (proteins were cloned under CMV promotor and with FLAG and HA affinity tags, respectively). The interaction for the wild-type PTEN, a non-aggregating mutation R47G, the mildly aggregating R173P and the severely aggregating frameshift mutant 800delA were compared.

Lysates were prepared as before and co-IP protocol for aggregated p53 was followed (see Material and Method section). In short, Tensin was immunoprecipitated using the FLAG tag and the presence of PTEN in the precipitates was investigated using the HA tag on the blots. An additional mutated version of 800delA was analyzed, in which an aggregation-reducing residue was introduced in the strongest aggregating regions. The combination of the A137R, Y178R and L193R mutations was used to achieve this. By plotting the number of cells in which cytoplasmic inclusions of PTEN can be observed by confocal microscopy, it was observed that the aggregation load is reduced by about half due to these mutations (data not shown). As can be seen from the Western blot of the co-IP, only the severely aggregating mutant 800delA was found to interact with Tensin (FIG. 31). Similar experiments were undertaken to probe the aggregation-specific interaction between PTEN and Osgin-1, showing similar results: interaction for the 800delA mutant, which is reduced in the control mutant (data not shown).

III. Screening Assays for Compounds Disrupting Co-Aggregation

Example 23

Screening for Compounds Having an Effect on the Aggregation of Mutant p53 Protein The effect of several compounds on the aggregation of mutant p53 protein was tested, using a stable reporter cell line: U2OS-p53R175H-PG13. The human osteosarcoma U-2 OS cells (ATCC number HTB-96) express wild-type p53 and is commonly used as a cellular model for studying p53 function. The U-2 OS cells were stably transfected with plasmid expressing the R175H mutant (pcDNA3-HA-p53 R175H) and PG13 luciferase. When the aggregation of R175H mutant is inhibited (and thus the dominant negative effect of mutant p53 is suppressed), the wild-type p53 transcribes the PG-13 reporter gene and gives luciferase signal.

The U2OS-p53R175H-PG13 cells were incubated in the presence of different concentrations of compounds ranging from 15 to 150 μM, and the effect of compounds was analyzed at different points. Some compounds caused the inhibition of mutant p53's DN effect (data not shown).

The effect of the compounds on the aggregation of mutant p53 was then analyzed. Some compounds inhibited the aggregation of p53 mutant R175H (data not shown).

Example 24

Screening for Compounds Having an Effect on the Aggretation of Wild-Type p53 Protein in the Presence of Chemotherapeutic Agent Commonly used chemotherapeutic agents, such as cisplatin, were found to be able to induce protein aggregation in a cell-line carrying wild-type p53 and increase aggregation of mutant p53 (see Example 20). Since these compounds rely on inducing apoptosis in the tumor cells, loss of wild-type p53 through aggregation may be an important mechanism for the emergence of drug-resistance.

A panel of tumor cell lines of known p53 status will be employed, such as the wild-type cell line U2OS and the melanoma line Mel1617 carrying Y220C cells. Cells will be treated with compound plus chemotherapeutic agent and cell number after three days of treatment will be determined. Synergistic effects of compound on the effectiveness of chemotherapeutic agent will be calculated from the cell numbers observed with the single treatments. Chemotherapeutic agents will be cisplatin, doxorubicin and 5-FU. Sensitization factor will be calculated.

At an early time point, before massive cell death sets in, such as after 6 or 10 hours of treatment, cell lysates will be prepared and Native page Western blot analysis of the aggregation status of p53 will be performed, as well as assessment of the functional status of the p53 pathway by qPCR, or a global analysis will be performed of the functional status of the cell by genome-wide RNA sequencing. The exact time point will be determined by time-resolved high content analysis of the number of p53 inclusions in these cells.

Example 25

Screening for Compounds Having an Effect on the Aggregation of Wild-Type p53 Protein in the Presence of Chemotherapeutic Agent Fusion proteins of human p53 were generated, both wild-type or with a mutation (e.g., R175H), with a fluorescent protein (e.g., Cherry) in a mammalian expression vector, driven by a CMV promoter, and containing a G418-resistance marker. Subsequently, these constructs were transfected in several cell lines, including HEK293, U2OS and Saos2, followed by selection for G418 resistance. Following selection, it was observed that most TG418-resistant cells, transfected with p53-R175H/Cherry, expressed both cytoplasmic and nuclear inactive p53-R175H/Cherry protein. However, when analyzing cells transfected with p53-WT/Cherry, the cells either did not show any expression anymore (probably silenced through methylation), or contained cytoplasmic inclusions of aggregated p53-WT/Cherry (data not shown), showing that aggregation of p53-WT is an actual mechanism of eliminating the tumor-suppressor activity of p53. These stable cell lines are excellent tools for compound screening: they can be used to reactivate the aggregated p53 that can be observed (i) by high content screening (migration from cytoplasm to nucleus) and/or (ii) by following the survival of these cells upon treatment with compounds.

IV. Materials and Methods to the Examples

In Silico Analysis of the Aggregation of p53 Wild-Type and Mutants

The aggregation propensity of p53 was analyzed using TANGO,[47] an algorithm to predict aggregation-nucleating sequences in proteins. The effect of cancer mutants on the conformational stability of the p53 DNA binding domain were taken from the literature[48] or else estimated using the FoldX force field.[49]

In Silico Screening of Protein Sequences Analogous with p53-Aggregating Sequence The Human proteome assembly was obtained from intregr8 server at EBI and was filtered for sequence redundancy (85% sequence identity) using cd-hit algorithm.[75] An exhaustive sequence-searching algorithm was employed to search for sequences similar to p53β, allowing up to two mutations. The results were filtered for swiss-prot keywords "membrane," "secreted," "uncharacterized," and "putative" to retain the most relevant hits (list of peptides in Table 2).

In Vitro Peptide-Binding Assay

Peptides of selected sequences were spot synthesized on PVDF membrane (PepSpot, JPT). The membranes were blocked by 1% BSA in phosphate-buffered saline for 1 hour at room temperature, and then incubated with biotinylated peptide containing the p53-aggregating sequence for 1 hour. After rinsing with 0.1% TWEEN® 20 in 25 mM MES buffer pH 7.0, membranes were incubated in HRP-labeled Streptavidin (Thermo) and visualized with electrochemical luminescence (ECL) system.

Plasmid Construction

The mammalian expression plasmid pCMV-HA-p53 encoding HA-tag (YPYDVPDYA (SEQ ID NO:64)) in the N-terminal of full-length p53 has been described elsewhere.[50] Point mutations were introduced to pCMV-HA-p53 vector by oligonucleotide primer-based PCR mutagenesis using Pwo DNA polymerase (Roche). Vectors that express FLAG-tagged proteins were generated using Gateway recombination technology (Invitrogen) according to the manufacturer's instructions. The pcDNA3-FLAG-p53 encoding FLAG-tag (DYKDDDDK (SEQ ID NO:65)) in the N-terminal of full-length p53 is commercially available (plasmid 10838, Addgene). The mammalian expression plasmid pcDNA3-HA-p73α encoding HA-tag (YPYDVPDYA (SEQ ID NO:64)) in the N-terminal of the full-length TAp73α isoform was kindly provided by Prof Gerry Melino (Rome). The pCMV-TAp63α encoding the full-length TAp63α isoform is commercially available (OriGene). The transcriptional activity of p53 was examined by PG13-luciferase reporter plasmid, which contains 13 contiguous p53 DNA-binding sites upstream of the firefly luciferase gene. The pRL-CMV vector (Promega), holding a *Renilla* luciferase, was used as a control vector.

Cell Culture and Transient Transfection

Human cell lines osteosarcoma SaOS-2 (p53-null) and U-2 OS (p53 wild-type), pharynx carcinoma Detroit 562 (p53-R175H), T-cell leukemia 1301 (p53-R282W), brain astrocytoma MOG-G-CCM (p53-R110P), bladder carcinoma HT-1376 (p53-P250L), colon adenocarcinoma WiDr (p53-R273H) and Ramos Burkitt's lymphoma (p53 I254D) cell lines were all cultured in DMEM supplemented with 10% fetal calf serum (Gibco), L-glutamine (4 mM), penicillin (100 U/ml), and streptomycin (100 U/ml). Proliferating cell cultures were maintained in a 5% $CO_2$-humidified incubator at 37° C. Co-transfection of 5 μg pCMV-HA-p53 and 5 μg pcDNA3-FLAG-p53 (or p73 and p63 plasmids) were performed using 50 μL of Lipofectamine 2000 (Invitrogen) following the product manual. Briefly, cells were seeded at $1\times10^6$ cells per 10 cm petri dish (containing gelatin-coated coverslips for immunofluorescence) and reached 90% confluency before transfection. The complex of DNA and Lipofectamine 2000 was prepared in 1250 μL DMEM and incubated for 20 minutes before adding to cells. For luciferase assay, the transfections were performed in 6-well plates and all materials were scaled down in proportion. Twenty-four hours after transfection, cells were removed from the incubator and examined.

HeLa (Human epithelial carcinoma) cells were cultured in DMEM supplemented with 10% fetal calf serum (Gibco), L-glutamine (4 mM), penicillin (100 U/ml), and streptomycin (100 U/ml). Proliferating cell cultures were maintained in a 5% CO2-humidified incubator at 37° C. Co-transfection of 2.5 μg pcDNA3-HA-p53 and 5 μg pDEST-FLAG-CPNE2 (or other FLAG-tagged proteins) were performed using 15 μL of FuGENE HD (Roche) following the product manual. Briefly, cells were seeded at $2.5\times10^6$ cells per 10 cm petri dish (containing gelatin-coated coverslips for immunofluorescence) and reached 90% confluency before transfection. The complex of DNA and FuGENE HD was prepared in 500 μL DMEM and incubated for 20 minutes before adding to cells. For stable transfection, DMEM medium containing 10% fetal calf serum and 500 μg/mL G418 was used to select colonies that carried the transfected vector for six weeks, and expression of the vector was validated by Western blot. Stably transfected cells were maintained in medium containing 250 μg/mL G418 for further analysis. Transfection of siRNA for p53 (Santa Cruz) was performed using X-tremeGENE siRNA transfection reagent (Roche) according to the manufacturer's instructions.

Immunofluorescence Staining

The transgenic mouse models used in this study have been described elsewhere.[13] Tissues were fixed in 4% formaldehyde, dehydrated, embedded in paraffin, and sectioned (5 μm). Paraffin-embedded tissues were deparaffinized in changes of xylene and rehydrated in decreasing concentrations of ethanol. In order to eliminate fixation-caused autofluorescence, tissue sections were incubated in 1 mg/ml sodiumborohydrate for 30 minutes. For cultured cells, coverslips were rinsed twice with phosphate-buffered saline (PBS) and fixed with 4% paraformaldehyde for 20 minutes at 21° C. After being rinsed with PBS, cells were permeabilized and blocked with 0.5% TRITON®-X100 and 2% BSA in PBS for 1 hour. The primary antibodies for HA tag (anti-HA.11 mouse monoclonal, Covance), FLAG-tagged (rabbit polyclonal, Abcam), p53 (mouse monoclonal, Santa Cruz), Vimentin (mouse monoclonal, Santa Cruz), TAp63α (rabbit polyclonal, Santa Cruz), Tap73α (rabbit polyclonal, Abcam) or copine-2 (rabbit polyclonal, Santa Cruz) were respectively diluted 1:150 in blocking buffer and incubated for 40 minutes. The secondary antibodies (goat anti-mouse-Alexa594 or goat anti-rabbit-Alexa488, Invitrogen) were diluted to 1:1000 and incubated for 30 minutes. After staining with DAPI (1:10, 000) and Thioflavin T (10 μM), the coverslips were added with antifade reagent (ProLong Gold, Invitrogen) and kept in dark for 24 hours. Images were acquired with a confocal fluorescence microscope (Ez-cl, Nikon).

A11 staining (Invitogen) was performed according to the manufacturer's instructions. In brief, paraffin sections were deparafinized using xylene and ethanol series, and washed in PBS. Subsequently, antigen retrieval was performed using a 0.1 M glycine/PBS, pH 3.5 buffer in a microwave oven for 35 minutes and slides were allowed to cool in the same bath for 30-45 minutes. Blocking was then performed in 1% BSA, 0.1% cold water fish skin gelatin, 0.1% TWEEN® 20 in PBS with 0.05% sodium azide. A11 antibody (diluted in a 1:1 mixture of blocking solution and PBS to a final concentration of 1-5 μg/mL) was incubated overnight at 4° C. After some washing steps with PBS, the appropriate secondary antibody (Alexa 488 or Alexa 594 conjugated) diluted in a 1:1 mixture of PBS and blocking solution, was added for 1 hour in the dark. Eventually, slides were washed and mounted in ProlongGold (Invitrogen) and subjected to microscopic analysis.

Electrophoresis and Western Blot

SaOS-2 or Hela cells were rinsed with ice-cold 20 mM Tris-HCl, 150 mM NaCl, pH 7.4 (TBS) and lysed with 18 mM 3-[(3-cholamidopropyl) dimethylammonio]-1-propanesulfonic acid (CHAPS) in TBS with DNase and protease inhibitors for 30 minutes at 21° C. or on ice, respectively. Whole-cell lysate was fractionated by both SDS-PAGE (NuPAGE system, Invitrogen) and Blue-Native PAGE (NativePAGE system, Invitrogen) following the product manuals. For SDS-PAGE, sample was denatured at 95° C. for 10 minutes in the presence of 2% sodium dodecyl sulfate (SDS) and then fractionated by 10% Bis-Tris gels in MES-SDS running buffer (0.1% SDS, 50 mM MES, and 50 mM Tris-Base). For Blue-Native PAGE, cell lysate was added with 20% glycerol and 5 mM Coomassie G-250 before loading onto 3-12% Novex Bis-Tris gradient gels. The electrophoresis was performed in a running buffer containing 50 mM BisTris and 50 mM Tricine (plus 0.004% Coomassie G-250 in cathode buffer) under fixed voltage (100V) at 21° C. for 120 minutes. Proteins were transferred onto polyvinylidene fluoride (PVDF) membranes and stained with Coomassie G-250 to display molecular-weight markers (NativeMark, Invitrogen). After fixation with 8% acetic acid for 20 minutes, the PVDF membranes were air-dried and destained with 100% methanol. Membranes were blocked overnight with 4% Bovine Serum Albumin (BSA) in TBS at 4° C. before immunoblotting. To detect HA or FLAG-tagged p53, p63 or p73 on the membrane, the primary antibody (anti-HA.11, Covance) was diluted to 1:1000 in blocking buffer and incubated for 1 hour at 21° C. After three times of rinsing with TBS containing 0.1% TWEEN® 20 (TBST), the membrane was stained with horseradish peroxidase (HRP)-conjugated goat anti-mouse IgG (Promega) and visualized with electrochemical luminescence (ECL) system. Following the irreversible inactivation of HRP by sodium azide ($NaN_3$), the membrane was probed with rabbit anti-FLAG and HRP-conjugated goat anti-rabbit antibodies to detect FLAG-tagged WT p53.

Electroporation of Fluorescently Labeled Peptides into SaOS-2 Cells

The DyLight 488-conjugated fluorescent peptide with amino acid sequence RPILTIITLE or RPILTRITLE (95% purity) was purchased from JPT Peptide Technologies. Peptide was transiently transfected into SaOS-2 cells using a gene pulser Xcell electroporation system (Bio-Rad laboratories Inc) following the manufacturer's instruction.

Luciferase Assay

Wild-type p53 is a transcription factor that induces expression of target genes through binding to a specific DNA responsive element. In order to examine the transdominant activity of p53 mutants, the PG13-luciferase reporter plasmid was used, which contains 13 contiguous p53 DNA-binding sites upstream of the firefly luciferase gene. SaOS-2 cells growing in 6-well plates were co-transfected with pCMV-HA p53 mutant (0.5 µg), PG13 luciferase reporter (0.4 µg) and pRL-SV40-*renilla* luciferase (0.1 µg). The luciferase activity was measured using the Dual-Luciferase Reporter Assay system (Promega) and microplate luminometer (POLARstar). Transcriptional activation by p53 was calculated as the ratio of firefly luciferase activity (reporter)/*Renilla* luciferase activity (control).

Co-Immunoprecipitation

SaOS-2 cells co-transfected with mutant HA-p53 and wild-type FLAG-p53 (or p63, p73) were lysed with CHAPS in TBS with DNase and protease inhibitors for 30 minutes at 21° C. The cell lysate (300 µL) was incubated with mouse anti-HA (or Do-1 anti-p53 in the case p73 was co-transfected) antibody (2 µL) overnight at 4° C. Then, 30 µL of immobilized protein G agarose (Thermo Fisher Scientific) was added, which had been blocked with 2% BSA and untransfected SaOS-2 cell lysate overnight. After incubation at 21° C. for 2 hours, the agarose beads were rinsed with 200 µL TBS five times, and subsequently eluted by heating at 95° C. in presence of SDS. The co-immunoprecipitated wild-type FLAG-53 (or p63, p73) was detected with rabbit polyclonal antibodies.

Hela cells co-transfected with mutant HA-p53 and FLAG-tagged proteins were lysed with RIPA buffer (Thermo) with DNase and protease inhibitors (Roche) for 30 minutes on ice. The cell lysate (300 µL) was incubated with rabbit anti-FLAG (or anti-copine-2) antibody (2 µL) overnight at 4° C. Then, 30 µL of immobilized protein G agarose (Thermo) was added, which had been previously blocked with 2% BSA overnight at 4° C. After incubation at 21° C. for 1 hour, the agarose beads were rinsed with 200 µL TBS three times, and subsequently eluted by heating at 95° C. in presence of SDS (without DTT). The co-immunoprecipitated p53 was detected with mouse anti-HA antibody or anti-p53.

Quantitative Reverse Transcription-PCR(RT-qPCR)

The dominant effects of p53 mutants on transactivation of four target genes (MDM2, BAX, NOXA, and p21) were determined by RT-qPCR. SaOS-2 cells were co-transfected with GFP, WT and mutant p53 (or p63, p73) and incubated for 24 hours before isolation of total RNA using RNEASY® mini kit (QIAGEN). Reverse transcription was performed using the iScript cDNA Synthesis Kit (Bio-Rad) according to the manufacturer's protocols. Quantitative real-time PCR was performed using iQ SYBR Green Supermix (Bio-Rad) on an iCycler iQ real-time PCR detection system (Bio-Rad), using the following primers: p73 forward 5'-AACGCTGC-CCCAACCACGA-3' (SEQ ID NO:66), reverse 5'-GCCG-GTTCATGCCCCCTACA-3' (SEQ ID NO:67); p63 forward 5'-GAAGATGGTGCGACAAACAA-3' (SEQ ID NO:68), reverse 5'-ATGATGAACAGCCCAACCTC-3' (SEQ ID NO:69); BAX forward 5'-TGCTTCAGGGTTTCATCCAG (SEQ ID NO:70), reverse 5'-GGCGGCAATCATCCTCTG-3' (SEQ ID NO:71); NOXA forward 5'-TGGAAGTCGAGT-GTGCTACTCAACT-3' (SEQ ID NO:72), reverse 5'-AGAT-TCAGAAGTTTCTGCCGGAA-3' (SEQ ID NO:73); p21 forward 5'-CGCTAATGGCGGGCTG-3' (SEQ ID NO:74), reverse 5'-CGGTGACAAAGTCGAAGTTCC-3' (SEQ ID NO:75); MDM2 forward 5'-ACCTCACAGATTCCAGCT-TCG-3' (SEQ ID NO:76), reverse 5'-TTTCATAGTATAAGT-GTCTTTTT-3' (SEQ ID NO:77). Jun-B forward 5'-TGGAA-CAGCCCTTCTACCAC-3' (SEQ ID NO:78), Jun-B reverse 5'-CTCAGGAGCATGGGGATAAA-3' (SEQ ID NO:79); $p57^{Kip2}$ forward 5'-CGTTCCACAGGCCAAGTGCG-3' (SEQ ID NO:80), $p57^{Kip2}$ reverse 5'-GCTGGTGCGCAC-TAGTACTG-3' (SEQ ID NO:81) GAPDH forward 5'-TGATGGTACATGACAAGGTGC-3' (SEQ ID NO:82), GAPDH reverse 5'-ACAGTCCATGCCATCACTGC-3' (SEQ ID NO:83). The expression level of each gene was normalized against GADPH, GFP and p53 (or p63, p73).

FT-IR Spectroscopy

Fourier Transform Infrared Spectroscopy was performed on a Tensor 37 FT-IR spectrometer equipped with a BioATR II cell (Bruker). The detector was cooled with liquid nitrogen, and the Bio-ATR II cell was purged by a continuous flow of dried air to minimize water vapor that may interfere with the result. Before and after each measurement, the crystal of the ATR cell was washed with ethanol and water. Samples were measured against background composed of water-covered crystal.

Inhibition of Protein Synthesis, Degradation and Vimentin Network

In the degradation stability test, protein synthesis was blocked by 60 µg/mL cycloheximide 24 hours after transfection, and cells were lysed 0, 3, 6, 12, 24 and 48 hours after the addition of cycloheximide. In the case where protein degradation needed to be inhibited, 10 µM MG-132 was added to cell culture four hours after transfection. In the case where vimentin network needed to be interfered, nocodazole (0.2 µg/ml) was added to SaOS-2 cells 6 hours after transfection. Cells were analyzed by immunofluorescence after 24 hours.

Statistical Analysis

The expression of target genes measured by qPCR data under different conditions was analyzed using unpaired two-tailed t-test, and the frequency of TP53 LOH in LFS families carrying different mutant types was compared by Chi-square test. Similarly, the activity of caspase-8 measured by colorimetric assay and BrdU-positive cells in proliferation assay were analyzed using unpaired two-tailed t-test. The statistical analysis of data was performed using the software packages of Excel 2003 and differences was considered significant if $p<0.05$.

Mitogen-Activated Protein Kinase (MAPK) Activation Assay

Upon reaching 60% confluency, Hela cells were transfected with empty vector, copine-2 without or with p53 R175H mutant and starved overnight in DMEM medium without serum. Vascular endothelial growth factor (VEGF, R&D Systems) was added to cells at final concentration of 25 ng/mL and incubated for 5 minutes, and then cells were lysed using CHAPS buffer containing protease inhibitor (Roche) and phosphatase inhibitor (Thermo) for 20 minutes on ice. Cell lysates were analyzed by SDS-PAGE and probed with antibodies specific for phosphorylated p44/p42 MAPK and total p44/p42 MAPK, respectively.

Caspase-8 Activity Colorimetric Assay

Hela cells were stably transfected with pcDNA3 vector, caspase-8 without or with p53 R175H mutant, and caspase-8 activity of each condition was determined by colorimetric assay kit (Abcam) following the product manual. Briefly, $3\times10^6$ cells were lysed using supplied lysis buffer, and 50 µl lysate was transferred to equal volume of 2× reaction buffer containing 10 mM DTT. After addition of 5 µL-labeled substrate IETD-pNA, the mixture was incubated at 37° C. for 2 hours. Fluorescence intensity of cleaved substrate was measured by a FLUOstar plate reader (BMG) equipped with a 400-nm excitation filter and 505-nm emission filter.

Proliferation Assays

The 4T1 mouse breast cancer cells were stably transfected with pcDNA3 vector, p53 R175H mutant or R175H/I254R mutant, and the expression of p53 was confirmed by Western blot. In the WST-1 assay, $1\times10^4$ cells were plated in 96-well plates. After 1, 2, 4, 6 and 8 days, cells were incubated with WST-1 for 2 hours, and the formazan formed was quantitated at 450 nm with a plate reader. In the BrdU incorporation assay, cells were cultured in 4-well slide chambers in the presence of 10 µM BrdU (Sigma) for 30 minutes, followed by fixation with 4% paraformaldehyde and permeabilization using 0.5% TRITON® X-100 in PBS. DNA was denatured by treating with 0.07 M NaOH for 3 minutes and neutralized by rinsing with TBS. After blocking with 1% BSA in TBS, slides were incubated with FITC-labeled anti-BrdU (Santa Cruz) and DAPI. The soft agar colony formation assay was performed in 24-well plates. Low melting agarose was heated and kept in 48° C., and cells were maintained in DMEM supplemented with 5% serum before growing in agar. The bottom layer was formed by 1% agarose in culture medium, and the top layer containing $1\times10^4$ cells was constructed using 0.5% agarose in medium. After 14 days, the number of cell colonies in each well was counted and the figure was taken by a dark-field microscope.

TABLE 1

Interaction between peptides indicated by peptide-binding assay, colocalization and co-IP experiments.

| UniProt ID of Target Protein | Target Sequence | SEQ ID NO | peptide mismatch with p53β | Sequence Identity protein | Coaggregation (peptide binding) | Colocalization (Pearson's correlation) | Co-IP (Ratio of IP/Input) |
|---|---|---|---|---|---|---|---|
| CPNE2_HUMAN | ILLIITD | 1 | 2 | 1.8% | 111.1% | 70% | 36.70% |
| P73_HUMAN | ILIIITL | 3 | 1 | 25.2% | 99.0% | 53% | 94.10% |
| P63_HUMAN | ILIIVTL | 4 | 2 | 23.6% | 92.0% | 62% | 102.30% |
| SPEF2_HUMAN | ILSIDTL | 5 | 2 | 4.7% | 79.6% | N/A | N/A |
| ANXA6_HUMAN | ILDIITS | 6 | 2 | 8.2% | 78.9% | 43% | 34.60% |
| CC132_HUMAN | ILTNTTL | 7 | 2 | 1.5% | 77.0% | 21% | 36.30% |
| METH_HUMAN | ILTIGTG | 8 | 2 | 1.3% | 49.2% | N/A | N/A |
| CCNI2_HUMAN | ALVIITL | 9 | 2 | 15.5% | 43.4% | 34% | 107.50% |
| CASP8_HUMAN | ILTILTE | 32 | 2 | 12.1% | 11.4% | 26% | 31.00% |
| DHX33_HUMAN | ILTIVSL | 34 | 2 | 11.0% | 10.2% | 2% | 16.42% |
| TAGAP_HUMAN | ILTILCL | 50 | 2 | 10.7% | 4.8% | 1% | 1.30% |

TABLE 2

Identity of the 56 peptide sequences analyzed in the peptide binding assay, related to Table 1.

| Position Nr | Uniprot | Aggregating sequence | Binding intensity (normalized) | SEQ ID NO |
|---|---|---|---|---|
| 42 | CPNE2_HUMAN | ILLIITD | 111,13 | 1 |
| 1 | P53_HUMAN | ILTIITL | 100,00 | 2 |
| 35 | P73_HUMAN | ILIIITL | 98,99 | 3 |
| 16 | P63_HUMAN | ILIIVTL | 92,04 | 4 |
| 54 | SPEF2_HUMAN | ILSIDTL | 79,63 | 5 |
| 29 | ANXA6_HUMAN | ILDIITS | 78,87 | 6 |
| 21 | CC132_HUMAN | ILTNTTL | 76,96 | 7 |
| 38 | METH_HUMAN | ILTIGTG | 49,22 | 8 |
| 23 | CCNI2_HUMAN | ALVIITL | 43,37 | 9 |
| 50 | MX2_HUMAN | DLTIIDL | 40,18 | 10 |
| 30 | CGRF1_HUMAN | ITTGITL | 36,69 | 11 |
| 37 | NOL11_HUMAN | ILTKYTL | 33,34 | 12 |
| 14 | VATA_HUMAN | IYTGITL | 32,12 | 13 |
| 2 | Control | RRPILTIITLEDGS | 30,92 | 14 |
| 24 | CYTIP_HUMAN | LLTIETL | 26,55 | 15 |
| 25 | PRA10_HUMAN | FLTIFTL | 26,40 | 16 |
| 18 | PK3C3_HUMAN | ILQIISL | 26,33 | 17 |
| 22 | KV122_HUMAN | ILTISSL | 23,80 | 18 |
| 49 | TAF4B_HUMAN | ILKQITL | 19,84 | 19 |
| 39 | CBPC3_HUMAN | ILTITTP | 19,59 | 20 |
| 53 | CM031_HUMAN | KLTIITS | 17,88 | 21 |
| 51 | CND2_HUMAN | ILTKSTL | 17,86 | 22 |
| 36 | RTEL1_HUMAN | ILTSGTL | 17,31 | 23 |
| 3 | PDS5A_HUMAN | IVTIITA | 17,21 | 24 |
| 17 | MP2K4_HUMAN | ILGKITL | 16,85 | 25 |
| 28 | MYST3_HUMAN | ILTKPTL | 16,14 | 26 |
| 44 | DHX29_HUMAN | ILQIITE | 15,64 | 27 |
| 56 | CD2A1_HUMAN | ILRQITL | 14,74 | 28 |
| 31 | ZN830_HUMAN | ILTIKEL | 14,09 | 29 |
| 34 | RFC5_HUMAN | ILTEIHL | 12,86 | 30 |
| 46 | BPA1_HUMAN | ILKNITL | 12,10 | 31 |
| 11 | CASP8_HUMAN | ILTILTE | 11,43 | 32 |
| 52 | AL2SA_HUMAN | GLTIPTL | 10,86 | 33 |
| 4 | DHX33_HUMAN | ILTIVSL | 10,20 | 34 |
| 15 | KV117_HUMAN | TLTISTL | 10,18 | 35 |
| 41 | SMG1_HUMAN | ILTLIEL | 9,77 | 36 |
| 33 | PTPC1_HUMAN | IKTIINL | 9,72 | 37 |

TABLE 2-continued

Identity of the 56 peptide sequences analyzed in the peptide binding assay, related to Table 1.

| Position Nr | Uniprot | Aggregating sequence | Binding intensity (normalized) | SEQ ID NO |
|---|---|---|---|---|
| 13 | HEAT1_HUMAN | ILTKISL | 8,65 | 38 |
| 32 | CXL11_HUMAN | IEVIITL | 8,54 | 39 |
| 27 | LRC40_HUMAN | IHAIITL | 8,22 | 40 |
| 43 | KLH32_HUMAN | ILCDITL | 7,89 | 41 |
| 55 | SCC4_HUMAN | IQTISTL | 7,06 | 42 |
| 48 | LONF2_HUMAN | ILVIITR | 6,81 | 43 |
| 10 | BPTF_HUMAN | VLTISTL | 6,72 | 44 |
| 47 | RTTN_HUMAN | ILTICTK | 6,48 | 45 |
| 7 | BN3D2_HUMAN | ALTFITL | 6,47 | 46 |
| 12 | DYH3_HUMAN | ILTFKTL | 6,20 | 47 |
| 40 | BCL6B_HUMAN | ILTDVTL | 5,88 | 48 |
| 8 | CD041_HUMAN | ITTVITL | 5,27 | 49 |
| 5 | TAGAP_HUMAN | ILTILCL | 4,81 | 50 |
| 45 | CT132_HUMAN | IKSIITL | 4,39 | 51 |
| 9 | PGTA_HUMAN | LLTIILL | 3,95 | 52 |
| 26 | TRI18_HUMAN | CLTIITG | 3,67 | 53 |
| 19 | GCDH_HUMAN | MLTEITL | 3,03 | 54 |
| 20 | DIP2B_HUMAN | ILTSQTL | 2,39 | 55 |
| 6 | EPMIP_HUMAN | LLTIINL | 1,55 | 56 |

REFERENCES

1. Aguzzi, A. & O'Connor, T. Protein aggregation diseases: pathogenicity and therapeutic perspectives. *Nat Rev Drug Discov* 9, 237-48 (2010).
2. Huo, Q. Protein complexes/aggregates as potential cancer biomarkers revealed by a nanoparticle aggregation immunoassay. *Colloids Surf B Biointerfaces* 78, 259-65 (2010).
3. Maslon, M. M. & Hupp, T. R. Drug discovery and mutant p53. *Trends Cell Biol* 20, 542-55 (2010).
4. Olivier, M. et al. The IARC TP53 database: new online mutation analysis and recommendations to users. *Hum Mutat* 19, 607-14 (2002).
5. Ang, H. C., Joerger, A. C., Mayer, S. & Fersht, A. R. Effects of common cancer mutations on stability and DNA binding of full-length p53 compared with isolated core domains. *J Biol Chem* 281, 21934-41 (2006).
6. Gannon, J. V., Greaves, R., Iggo, R. & Lane, D. P. Activating mutations in p53 produce a common conformational effect. A monoclonal antibody specific for the mutant form. *Embo J* 9, 1595-602 (1990).
7. Joerger, A. C. & Fersht, A. R. Structural biology of the tumor suppressor p53. *Annu Rev Biochem* 77, 557-82 (2008).
8. Chan, W. M., Siu, W. Y., Lau, A. & Poon, R. Y. How many mutant p53 molecules are needed to inactivate a tetramer? *Mol Cell Biol* 24, 3536-51 (2004).
9. Brosh, R. & Rotter, V. When mutants gain new powers: news from the mutant p53 field. *Nat Rev Cancer* 9, 701-13 (2009).
10. Su, X. et al. TAp63 suppresses metastasis through coordinate regulation of Dicer and miRNAs. *Nature* 467, 986-90 (2010).
11. Leong, C. O., Vidnovic, N., DeYoung, M. P., Sgroi, D. & Ellisen, L. W. The p63/p73 network mediates chemosensitivity to cisplatin in a biologically defined subset of primary breast cancers. *J Clin Invest* 117, 1370-80 (2007).
12. Gaiddon, C., Lokshin, M., Aim, J., Zhang, T. & Prives, C. A subset of tumor-derived mutant forms of p53 down-regulate p63 and p73 through a direct interaction with the p53 core domain. *Mol Cell Biol* 21, 1874-87 (2001).
13. Lang, G. A. et al. Gain of function of a p53 hot spot mutation in a mouse model of Li-Fraumeni syndrome. *Cell* 119, 861-72 (2004).
14. Ostermeyer, A. G., Runko, E., Winkfield, B., Ahn, B. & Moll, U. M. Cytoplasmically sequestered wild-type p53 protein in neuroblastoma is relocated to the nucleus by a C-terminal peptide. *Proc Natl Acad Sci USA* 93, 15190-4 (1996).
15. Johnston, J. A., Ward, C. L. & Kopito, R. R. Aggresomes: a cellular response to misfolded proteins. *J Cell Biol* 143, 1883-98 (1998).
16. Okorokov, A. L. & Orlova, E. V. Structural biology of the p53 tumor suppressor. *Curr Opin Struct Biol* 19, 197-202 (2009).

17. Fernandez-Escamilla, A. M., Rousseau, F., Schymkowitz, J. & Serrano, L. Prediction of sequence-dependent and mutational effects on the aggregation of peptides and proteins. *Nat Biotechnol* 22, 1302-6 (2004).
18. Bullock, A. N. & Fersht, A. R. Rescuing the function of mutant p53. *Nat Rev Cancer* 1, 68-76 (2001).
19. Ishimaru, D. et al. Fibrillar aggregates of the tumor suppressor p53 core domain. *Biochemistry* 42, 9022-7 (2003).
20. Kruse, J. P. & Gu, W. MSL2 promotes Mdm2-independent cytoplasmic localization of p53. *J Biol Chem* 284, 3250-63 (2009).
21. Liang, S. H. & Clarke, M. F. A bipartite nuclear localization signal is required for p53 nuclear import regulated by a carboxyl-terminal domain. *J Biol Chem* 274, 32699-703 (1999).
22. Haupt, S., Berger, M., Goldberg, Z. & Haupt, Y. Apoptosis—the p53 network. *J Cell Sci* 116, 4077-85 (2003).
23. Davison, T. S., Yin, P., Nie, E., Kay, C. & Arrowsmith, C. H. Characterization of the oligomerization defects of two p53 mutants found in families with Li-Fraumeni and Li-Fraumeni-like syndrome. *Oncogene* 17, 651-6 (1998).
24. Strano, S. et al. Physical and functional interaction between p53 mutants and different isoforms of p73. *J Biol Chem* 275, 29503-12 (2000).
25. Li, Y. & Prives, C. Are interactions with p63 and p73 involved in mutant p53 gain of oncogenic function? *Oncogene* 26, 2220-5 (2007).
26. Joerger, A. C. et al. Structural evolution of p53, p63, and p73: implication for heterotetramer formation. *Proc Natl Acad Sci USA* 106, 17705-10 (2009).
27. Rajan, R. S., Illing, M. E., Bence, N. F. & Kopito, R. R. Specificity in intracellular protein aggregation and inclusion body formation. *Proc Natl Acad Sci USA* 98, 13060-5 (2001).
28. Cam, H. et al. p53 family members in myogenic differentiation and rhabdomyosarcoma development. *Cancer Cell* 10, 281-93 (2006).
29. Boominathan, L. Some facts and thoughts: p73 as a tumor-suppressor gene in the network of tumor suppressors. *Mol Cancer* 6, 27 (2007).
30. Hishiya, A. & Takayama, S. Molecular chaperones as regulators of cell death. *Oncogene* 27, 6489-506 (2008).
31. Whitesell, L. & Lindquist, S. L. HSP90 and the chaperoning of cancer. *Nat Rev Cancer* 5, 761-72 (2005).
32. Ciocca, D. R. & Calderwood, S. K. Heat shock proteins in cancer: diagnostic, prognostic, predictive, and treatment implications. *Cell Stress Chaperones* 10, 86-103 (2005).
33. Sedlacek, Z., Kodet, R., Poustka, A. & Goetz, P. A database of gennline p53 mutations in cancer-prone families. *Nucleic Acids Res* 26, 214-5 (1998).
34. Powell, B., Soong, R., Iacopetta, B., Seshadri, R. & Smith, D. R. Prognostic significance of mutations to different structural and functional regions of the p53 gene in breast cancer. *Clin Cancer Res* 6, 443-51 (2000).
35. Samowitz, W. S. et al. Prognostic significance of p53 mutations in colon cancer at the population level. *Int J Cancer* 99, 597-602 (2002).
36. Davison, T. S. et al. p73 and p63 are homotetramers capable of weak heterotypic interactions with each other but not with p53. *J Biol Chem* 274, 18709-14 (1999).
37. Finlay, C. A. et al. Activating mutations for transformation by p53 produce a gene product that forms an hsc70-p53 complex with an altered half-life. *Mol Cell Biol* 8, 531-9 (1988).
38. Milner, J. & Medcalf, E. A. Cotranslation of activated mutant p53 with wild-type drives the wild-type p53 protein into the mutant conformation. *Cell* 65, 765-74 (1991).
39. Friedman, P. N., Chen, X., Bargonetti, J. & Prives, C. The p53 protein is an unusually shaped tetramer that binds directly to DNA. *Proc Natl Acad Sci USA* 90, 3319-23 (1993).
40. Goh, A. M., Coffin, C. R. & Lane, D. P. The role of mutant p53 in human cancer. *J Pathol* 223, 116-26 (2011).
41. Flores, E. R. et al. Tumor predisposition in mice mutant for p63 and p73: evidence for broader tumor-suppressor functions for the p53 family. *Cancer Cell* 7, 363-73 (2005).
42. Bensaad, K. et al. Change of conformation of the DNA-binding domain of p53 is the only key element for binding of and interference with p73. *J Biol Chem* 278, 10546-55 (2003).
43. Bullock, A. N. et al. Thermodynamic stability of wild-type and mutant p53 core domain. *Proc Natl Acad Sci USA* 94, 14338-42 (1997).
44. Rotter, V. p53, a transformation-related cellular-encoded protein, can be used as a biochemical marker for the detection of primary mouse tumor cells. *Proc Natl Acad Sci USA* 80, 2613-7 (1983).
45. Moll, U. M., Riou, G. & Levine, A. J. Two distinct mechanisms alter p53 in breast cancer: mutation and nuclear exclusion. *Proc Natl Acad Sci USA* 89, 7262-6 (1992).
46. Ostermeyer, A. G., Runko, E., Winkfield, B., Ahn, B. & Moll, U. M. Cytoplasmically sequestered wild-type p53 protein in neuroblastoma is relocated to the nucleus by a C-terminal peptide. *Proc Natl Acad Sci USA* 93, 15190-4 (1996).
47. Fernandez-Escamilla, A. M., Rousseau, F., Schymkowitz, J. & Serrano, L. Prediction of sequence-dependent and mutational effects on the aggregation of peptides and proteins. *Nat Biotechnol* 22, 1302-1306 (2004).
48. Bullock, A. N., Henckel, J. & Fersht, A. R. Quantitative analysis of residual folding and DNA binding in mutant p53 core domain: definition of mutant states for rescue in cancer therapy. *Oncogene* 19, 1245-56 (2000).
49. Schymkowitz, J. et al. The FoldX web server: an online force field. *Nucleic Acid Res* 33, W382-W388 (2005).
50. Di Como, C. J., Gaiddon, C. & Prives, C. p73 function is inhibited by tumor-derived p53 mutants in mammalian cells. *Mol Cell Biol* 19, 1438-49 (1999).
51. Butler et al. *Biochemistry* 42: 2396-406 (2003).
52. Joerger A C, Fersht A R. Structure-function-rescue: the diverse nature of common p53 cancer mutants. *Oncogene* 26:2226-42 (2007).
53. Vassilev L T. Small-molecule antagonists of p53-MDM2 binding: research tools and potential therapeutics. *Cell Cycle* 3:419-21 (2004).
54. Vassilev L T, Vu B T, Graves B, Carvajal D, Podlaski F, Filipovic Z, Kong N, Kammlott U, Lukacs C, Klein C, Fotouhi N, Liu E A. In vivo activation of the p53 pathway by small-molecule antagonists of MDM2. *Science* 303: 844-8 (2004).
55. Böttger A, Böttger V, Sparks A, Liu W L, Howard S F, Lane D P. Design of a synthetic Mdm2-binding mini protein that activates the p53 response in vivo. *Curr Biol.* 7:860-9 (1997).
56. Duncan S J, Grüschow S, Williams D H, McNicholas C, Purewal R, Hajek M, Gerlitz M, Martin S, Wrigley S K, Moore M. Isolation and structure elucidation of Chlorofusin, a novel p53-MDM2 antagonist from a *Fusarium* sp. *J Am Chem. Soc.* 123:554-60 (2001).
57. Issaeva N, Friedler A, Bozko P, Wiman K G, Fersht A R, Selivanova G. Rescue of mutants of the tumor suppressor p53 in cancer cells by a designed peptide. *Proc Natl Acad Sci USA.* 100:13303-7 (2003).

58. Moll U M, Slade N. p63 and p73: roles in development and tumor formation. *Mol Cancer Res.* 2:371-86 (2004).
59. Rosenbluth J M, Pietenpol J A. The jury is in: p73 is a tumor suppressor after all. *Genes Dev.* 22:2591-5 (2008).
60. Gaiddon C, Lokshin M, Ahn J, Zhang T, Prives C. A subset of tumor-derived mutant forms of p53 down-regulate p63 and p73 through a direct interaction with the p53 core domain. *Mol Cell Biol.* 21:1874-87 (2001).
61. Di Agostino S, Cortese G, Monti O, Dell'Orso S, Sacchi A, Eisenstein M, Citro G, Strano S, Blandino G. The disruption of the protein complex mutantp53/p73 increases selectively the response of tumor cells to anticancer drugs. *Cell Cycle.* 7:3440-7 (2008).
62. Tyedmers J, Mogk A, Bukau B. Cellular strategies for controlling protein aggregation. *Nat Rev Mol Cell Biol.* 11:777-88 (2010).
63. Tsvetkov P, Reuven N, Shaul Y. Ubiquitin-independent p53 proteasomal degradation. *Cell Death Differ.* 17:103-8 (2010).
64. Cellarier, E., Durando, X., Vasson, M. P., Farges, M. C., Demiden, A., Maurizis, J. C., Madelmont, J. C., and Chollet, P. (2003). Methionine dependency and cancer treatment. Cancer treatment reviews 29, 489-499.
65. Chiti, F., and Dobson, C. M. (2006). Protein misfolding, functional amyloid, and human disease. Annu Rev Biochem 75, 333-366.
66. Fulda, S. (2009). Caspase-8 in cancer biology and therapy. Cancer Lett 281, 128-133.
67. Madden, S. L., Galella, E. A., Riley, D., Bertelsen, A. H., and Beaudry, G. A. (1996). Induction of cell growth regulatory genes by p53. Cancer research 56, 5384-5390.
68. Perestenko, P. V., Pooler, A. M., Noorbakhshnia, M., Gray, A., Bauccio, C., and Jeffrey McIlhinney, R. A. (2010). Copines-1, -2, -3, -6 and -7 show different calcium-dependent intracellular membrane translocation and targeting. The FEBS journal 277, 5174-5189.
69. Rohan, S., Tu, J. J., Kao, J., Mukherjee, P., Campagne, F., Zhou, X. K., Hyjek, E., Alonso, M. A., and Chen, Y. T. (2006). Gene expression profiling separates chromophobe renal cell carcinoma from oncocytoma and identifies vesicular transport and cell junction proteins as differentially expressed genes. Clin Cancer Res 12, 6937-6945.
70. Rousseau, F., Schymkowitz, J., and Serrano, L. (2006). Protein aggregation and amyloidosis: confusion of the kinds? Curr Opin Struct Biol 16, 118-126.
71. Sawaya, M. R., Sambashivan, S., Nelson, R., Ivanova, M. I., Sievers, S. A., Apostol, M. I., Thompson, M. J., Balbirnie, M., Wiltzius, J. J., McFarlane, H. T., et al. (2007). Atomic structures of amyloid cross-beta spines reveal varied steric zippers. Nature 447, 453-457.
72. Tomsig, J. L., Snyder, S. L., and Creutz, C. E. (2003). Identification of targets for calcium signaling through the copine family of proteins. Characterization of a coiled-coil copine-binding motif. The Journal of biological chemistry 278, 10048-10054.
73. Ventura, S., Zurdo, J., Narayanan, S., Parreno, M., Mangues, R., Reif, B., Chiti, F., Giannoni, E., Dobson, C. M., Aviles, F. X., et al. (2004). Short amino acid stretches can mediate amyloid formation in globular proteins: the Src homology 3 (SH3) case. Proc Natl Acad Sci USA 101, 7258-7263.
74. Pawar A P, Dubay K F, Zurdo J, Chiti F, Vendruscolo M, Dobson C M (2005). Prediction of "aggregation-prone" and "aggregation-susceptible" regions in proteins associated with neurodegenerative diseases. J. Mol. Biol. 350, 379-392
75. Li, W., Jaroszewski, L., and Godzik, A. (2001). Clustering of highly homologous sequences to reduce the size of large protein databases. Bioinformatics 17, 282-283.
76. Martinez-Rivera M, Siddik Z H (2012). Resistance and gain-of-resistance phenotypes in cancers harboring wild-type p53. Biochem Pharmacol. 2012 Apr. 15; 83(8):1049-62.
77. Lin, K. Y., Lu, D., Hung, C. F., Peng, S., Huang, L., Jie, C., Murillo, F., Rowley, J., Tsai, Y. C., He, L., et al. (2007). Ectopic expression of vascular cell adhesion molecule-1 as a new mechanism for tumor immune evasion. Cancer research 67, 1832-1841.
78. Dobson, C. M. Principles of protein folding, misfolding and aggregation. Semin Cell Dev 6/0/15, 3-16 (2004).
79. Nelson, R. et al. Structure of the cross-beta spine of amyloid-like fibrils. Nature 435, 773-8 (2005).
80. Makin, O. S., Atkins, E., Sikorski, P., Johansson, J. & Serpell, L. C. Molecular basis for amyloid fibril formation and stability. Proc Natl Acad Sci USA 102, 315-20 (2005).

The invention claimed is:

1. A method of screening for a candidate compound, wherein said method comprises:
   contacting the candidate compound with a cell expressing both an aggregation-prone engineered member protein and one or more wild-type member proteins of a tumor suppressor protein aggregome, wherein the tumor suppressor protein aggregome comprises member proteins that form aggregation-specific interactions; and
   measuring co-aggregation of one or more member proteins of said tumor suppressor protein aggregome and/or the activity of one or more wild-type member proteins of said tumor suppressor protein aggregome expressed by the cell; and
   screening for a candidate compound that inhibited or disrupted co-aggregation of one or more member proteins of the tumor suppressorrm expressed by the cell,
   wherein said co-aggregation is mediated by the exposure of a beta-aggregating region present in said member proteins, said beta-aggregating region comprising a peptide that comprises: a stretch of 4 to 16 contiguous amino acids, at least 50% of which are hydrophobic amino acids, and in which at least one aliphatic residue or F is present, and if only one aliphatic residue or F is present, at least one residue selected from the group consisting of Y, W, A, M and T; and in which no more than one P, R, K, D or E residue is present.

2. The method of claim 1, further comprising:
   measuring the degree of degradation of the one or more wild-type member proteins and aggregation-prone engineered member protein of said tumor suppressor protein aggregome; or
   measuring cell survival of the cell; and/or
   measuring sensitivity of the cell to a chemotherapeutic agent.

3. The method of claim 1, wherein said tumor suppressor aggregome is selected from the group consisting of a p53 aggregome, a PTEN aggregome, a p16 aggregome, and a pRb aggregome, and wherein member proteins of a p53 aggregome are selected from the group consisting of p53, p63, p73, copine-2, and caspase-8;

member proteins of a first PTEN aggregome are selected from the group consisting of PTEN, and tensin-3;

member proteins of a second PTEN aggregome are selected from the group consisting of PTEN, and oxidative stress-induced growth inhibitor 1; and member proteins of a p16 aggregome are selected from the group consisting of p16 and p15.

4. The method of claim 3, wherein said aggregation-prone engineered member protein is a mutated tumor-suppressor protein.

5. The method of claim 4, wherein said aggregation-prone engineered member protein is a fusion protein of a wild-type member protein fused to a detectable protein.

6. A method of screening for a compound that inhibits or disrupts co-aggregation of at least one member protein of a tumor-associated protein aggregome, the method comprising:

contacting a cell with a candidate compound, wherein the cell is either:

a cell expressing both an aggregation-prone engineered member protein and one or more wild-type member proteins of the tumor-associated protein aggregome; or a cell expressing one or more wild-type member proteins of the tumor-associated protein aggregome in the presence of a chemotherapeutic agent; and measuring co-aggregation of one or more member proteins of the tumor-associated protein aggregome and/or the activity of one or more wild-type member proteins of the tumor-associated protein aggregome; and screening for a candidate compound that inhibited or disrupted co-aggregation of one or more member proteins of the tumor-associated protein aggregome expressed by the cell, wherein the co-aggregation is mediated by exposing a beta-aggregating region present in the member proteins, the beta-aggregating region comprising a peptide having a stretch of 4 to 16 contiguous amino acids, at least 50% of which are hydrophobic amino acids, and in which at least one aliphatic residue or F is present therein, and if only one aliphatic residue or F is present, at least two other residues selected from the group consisting of Y, W, A, M and T, and in which no P, R, K, D, or E residue is present.

7. The method according to claim 4, wherein the mutated tumor-suppressor protein is:

a mutated p53 carrying a mutation selected from the group consisting of R110P, R110L, R175H, Y220C, G245S, R248Q R249S, P250L, E258V, and R282W;

a mutated p16 carrying a mutation; or a mutated PTEN carrying a mutation selected from the group consisting of PTEN 800 del A, R173C, and R173P.

8. The method according to claim 5, wherein the detectable protein is a fluorescent protein.

9. A method of screening a candidate compound from a library of candidate compounds, the method comprising:

contacting a candidate compound with a cell that expresses at least one wild-type member protein of a tumor suppressor protein aggregome in the presence of a chemotherapeutic agent, wherein the tumor suppressor protein aggregome comprises member proteins that form aggregation-specific interactions;

interacting the cell and candidate compound with a chemotherapeutic agent selected from the group consisting of cisplatin, carboplatin, oxaliplatin, mechlorethamine, cyclophosphamide, chlorambucil, ifosfamide, vinorelbine, vindesine, docetaxel, topoisomerase inhibitors, irinotecan, topotecan, amsacrine, etoposide, etoposide phosphate, teniposide, doxorubicin, valrubicin, idarubicin, epirubicin, and fluorouracil so as to express the at least one wild-type member protein of a tumor suppressor protein aggregome;

measuring co-aggregation and/or activity of at least one member protein of the wild-type tumor suppressor protein aggregome expressed by the cell; and screening for a candidate compound that inhibited or disrupted co-aggregation of the at least one member protein of the tumor suppressor protein aggregome expressed by the cell, wherein co-aggregation is mediated by exposure of a beta-aggregating region present in the member proteins, wherein the beta-aggregating region comprises:

a stretch of 4 to 16 contiguous amino acids, at least 50% of which are hydrophobic amino acids, and in which at least one aliphatic residue or F is present, and if only one aliphatic residue or F is present, at least one residue selected from the group consisting of Y, W, A, M and T; and in which no more than one P, R, K, D or E residue is present.

10. The method according to claim 9, further comprising:

measuring the degree of degradation of the one or more wild-type member proteins and aggregation-prone engineered member protein of the tumor suppressor protein aggregome;

measuring cell survival of the cell; and/or measuring sensitivity of the cell to a chemotherapeutic agent.

11. The method according to claim 9, wherein the tumor suppressor aggregome is selected from the group consisting of a p53 aggregome, a PTEN aggregome, a p16 aggregome, and a pRb aggregome, and wherein member proteins of a p53 aggregome are selected from the group consisting of p53, p63, p73, copine-2, and caspase-8;

member proteins of a first PTEN aggregome are selected from the group consisting of PTEN, and tensin-3;

member proteins of a second PTEN aggregome are selected from the group consisting of PTEN, and oxidative stress-induced growth inhibitor 1; and member proteins of a p16 aggregome are selected from the group consisting of p16 and p15.

12. The method according to claim 11, wherein the aggregation-prone engineered member protein is a mutated tumor suppressor protein.

13. The method according to claim 11, wherein the aggregation-prone engineered member protein is a fusion protein of a wild-type member protein fused to a detectable protein.

14. The method according to claim 13, wherein the detectable protein is a fluorescent protein.

15. The method according to claim 12, wherein the mutated tumor suppressor protein is:

a mutated p53 carrying a mutation selected from the group consisting of R110P, R110L, R175H, Y220C, G245S, R248Q R249S, P250L, E258V, and R282W;

a mutated p16 carrying a mutation; or a mutated PTEN carrying a mutation selected from the group consisting of PTEN 800 del A, R173C, and R173P.

* * * * *